United States Patent [19]

Albertsen et al.

[11] Patent Number: 5,783,666
[45] Date of Patent: Jul. 21, 1998

[54] **APC (ADENOMATOUS *POLYOSIS COLI*) PROTEIN**

[75] Inventors: Hans Albertsen, Salt Lake City, Utah; Rakesh Anand, Sandbach, England; Mary Carlson; Joanna Groden, both of Salt Lake City, Utah; Philip John Hedge, Winsford, England; Geoff Joslyn, Salt Lake City, Utah; Kenneth Kinzler, Baltimore, Md.; Alexander Fred Markham, Crewe, England; Yusuke Nakamura, Tokyo, Japan; Andrew Thliveris, Salt Lake City, Utah; Bert Vogelstein, Baltimore, Md.; Raymond L. White, Salt Lake City, Utah

[73] Assignees: The Johns Hopkins University, Baltimore, Md.; The University of Utah, Salt Lake City, Utah; Zeneca Pharmaceuticals, England; The Cancer Institute, Tokyo, Japan

[21] Appl. No.: 452,655

[22] Filed: May 25, 1995

Related U.S. Application Data

[62] Division of Ser. No. 289,548, Aug. 12, 1994, which is a division of Ser. No. 741,940, Aug. 8, 1991, Pat. No. 5,352,775.

[30] Foreign Application Priority Data

| Jan. 16, 1991 | [GB] | United Kingdom | 9100962 |
| Jan. 16, 1991 | [GB] | United Kingdom | 9100963 |
| Jan. 16, 1991 | [GB] | United Kingdom | 9100975 |
| Jan. 16, 1994 | [GB] | United Kingdom | 9100974 |

[51] Int. Cl.⁶ ............................................. C07K 14/47
[52] U.S. Cl. .............................. 530/350; 530/828; 930/10
[58] Field of Search ................................. 530/350, 828, 530/843, 844; 930/10

[56] References Cited

U.S. PATENT DOCUMENTS

5,098,823  3/1992  Bodner et al.
5,137,806  8/1992  LeMaistie et al.

FOREIGN PATENT DOCUMENTS

WO 89/01481  8/1988  WIPO.

OTHER PUBLICATIONS

Groden, et al., "Identification and Characterization of the Familial Adenomatous *Polyposis Coli* Gene", *Cell*, 66:589–600 (1991).

Joslyn, et al., "Identification of Deletion Mutations and Three New Genes at the Familial Polyposis Locus", *Cell*, 66:601–613 (1991).

Kinzler, et al., "Identification of FAP Locus Genes From Chromsome 5q21", *Science*, 253:665–669 (1991).

Nishisho, et al., "Mutations of Chromosome 5q21 Genes in FAP and Colorectal Cancer Patients", *Science*, 253:665–669 (1991).

Orita, et al., *Genomics*, vol. 5, pp. 874–879, 1989.

Stanbridge, et al., "Identifying Tumor Suppressor Genes in Human Colorectal Cancer", *Science*, 247:12–13 (1990).

Fearon et al., "Identification of a Chromosome 18q Gene That is Altered in Colorectal Cancer", *Science*, 247:49–56 (1990).

Baker et al., "Chromosome 17 Deletions and p. 53 Gene Mutations in Colorectal Carcinomas", *Science*, 244:217–221 (1989).

Bodmer et al., "Localization of the Gene for Familial Adenomatous Polyposis on Chromosome 5", *Nature*, 328:614–616 (1987).

*Primary Examiner*—John Ulm
*Assistant Examiner*—Christine Saoud
*Attorney, Agent, or Firm*—Banner & Witcoff, Ltd.

[57] ABSTRACT

A human gene termed APC is disclosed. Methods and kits are provided for assessing mutations of the APC gene in human tissues and body samples. APC mutations are found in familial adenomatous polyposis patients as well as in sporadic colorectal cancer patients. APC is expressed in most normal tissues. These results suggest that APC is a tumor suppressor.

5 Claims, 40 Drawing Sheets

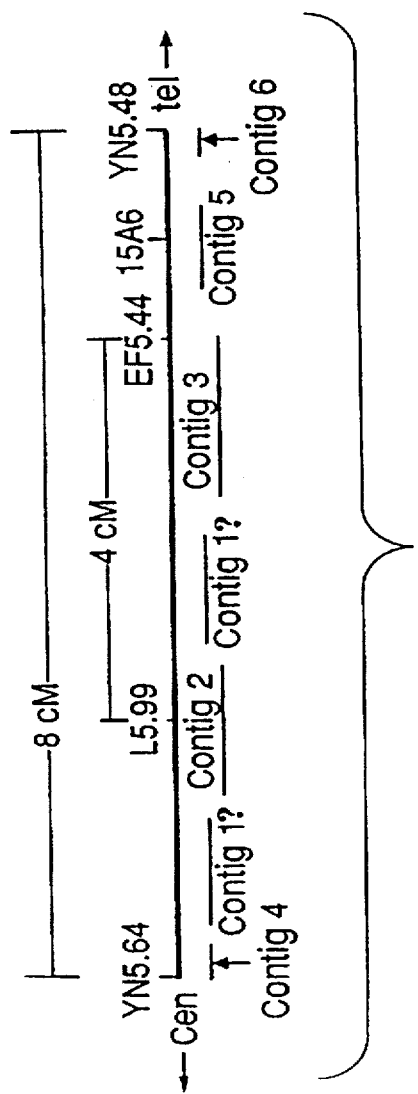
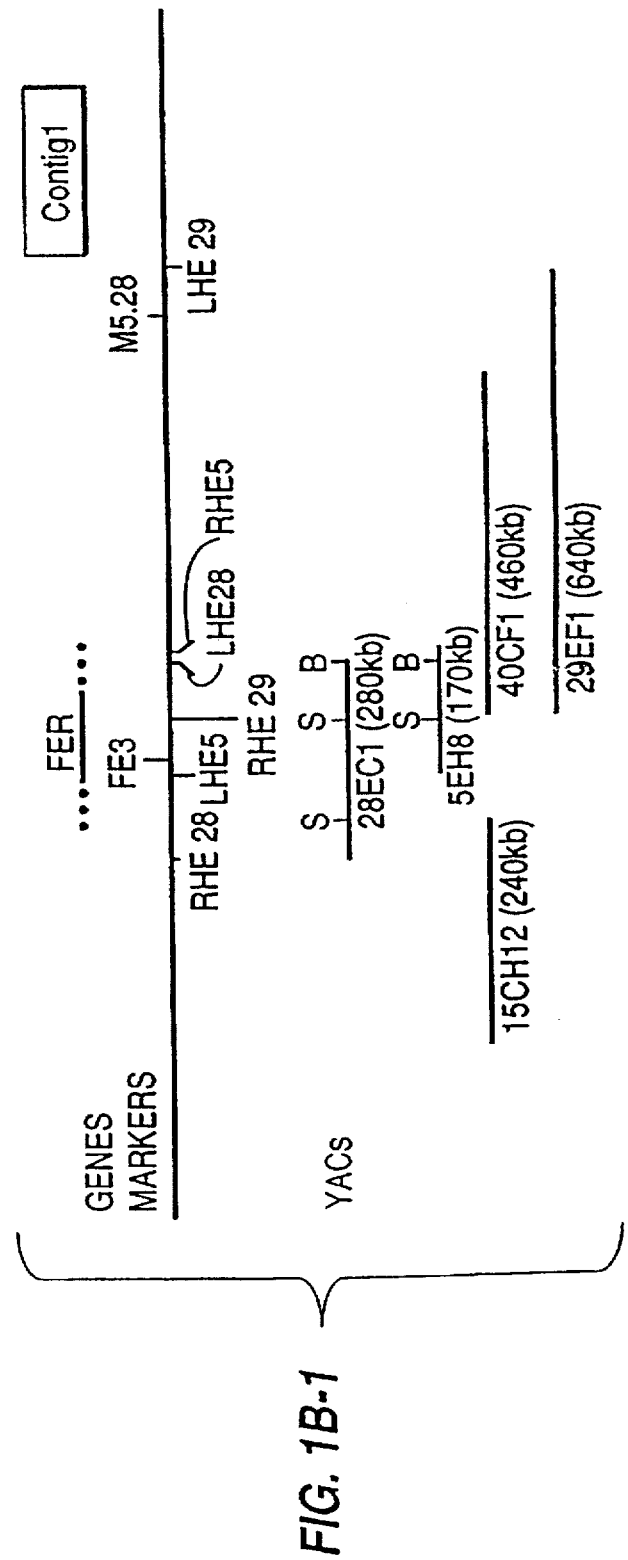
FIG. 1A
FIG. 1B-1

FIG. 2A

TB1 Amino Acid Sequence

| | |
|---|---|
| VAPVVVGSGR APRHPAPAAM HPRRPDGFDG LGYRGGARDE QGFGGAFPAR SFSTGSDLGH | 60 |
| WVTPPPDIPG SRNLHWGEKS PPYGVPTTST PYEGPTEEPF SSGGGGSVQG QSSEQLNRFA | 120 |
| GFGIGLASLF TENVLAHPCI VLRRQCQVNY HAQHYHLTPF TVINIMYSFN KTQGPRALWK | 180 |
| GMGSTFIVQG VTLGAEGIIS EFTPLPREVL HKWSPKQIGE HLLLKSLTYV VAMPFYSASL | 240 |
| IETVQSEIIR DNTGILECVK EGIGRVIGMG VPHSKRLLPL LSLIFPTVLH GVLHYIISSV | 300 |
| IQKFVLLILK RKTYNSHLAE STSPVQSMLD AYFPELIANF AASLCSDVIL YPLETVLHRL | 360 |
| HIQGIRTIID NTDLGYEVLP INTQYEGMRD CINTIRQEEG VEGFYKGFGA VIIQYTLHAA | 420 |
| VLQITKIIYS TLLQ | 434 |

FIG. 2B

TB2 Amino Acid Sequence

```
ELRRFDRFLH EKNCHTDLLA KLEAKTGVNR SFIALGVIGL VALYLVFGYG ASLLCNLIGF  60
GYPAYISIKA IESPNKEDDT QWLTYWVYG VFSIAEFFSD IFLSWFPFYY ILKCGFLLWC  120
MAPSPSNGAE LLYKRIIRPF FLKHESQMDS VVKDLKDKAK ETADAITKEA KKATVNLLGE  180
EKKST                                                              185
```

Figure 3A

```
         10         20         30         40         50         60
  MAAASYDQLL KQVEALKMEN SNLRQELEDN SNHLTKLETE ASNMKEVLKQ LQGSIEDEAM
         70         80         90        100        110        120
  ASSGQIDLLE RLKELNLDSS NFPGVKLRSK MSLRSYGSRE GSVSSRSGEC SPVPMGSFPR
        130        140        150        160        170        180
  RGFVNGSRES TGYLEELEKE RSLLLADLDK EEKEKDWYYA QLQNLTKRID SLPLTENFSL
        190        200        210        220        230        240
  QTDMTRRQLE YEARQIRVAM EEQLGTCQDM EKRAQRRIAR IQQIEKDILR IRQLLQSQAT
        250        260        270        280        290        300
  EAERSSQNKH ETGSHDAERQ NEGQGVGEIN MATSGNGQGS TTRMDHETAS VLSSSSTHSA
        310        320        330        340        350        360
  PRRLTSHLGT KVEMVYSLLS MLGTHDKDDM SRTLLAMSSS QDSCISMRQS GCLPLLIQLL
        370        380        390        400        410        420
  HGNDKDSVLL GNSRGSKEAR ARASAALHNI IHSQPDDKRG RREIRVLHLL EQIRAYCETC
        430        440        450        460        470        480
  WEWQEAHEPG MDQDKNPMPA PVEHQICPAV CVLMKLSFDE EHRHAMNELG GLQAIAELLQ
        490        500        510        520        530        540
  VDCEMYGLTN DHYSITLRRY AGMALTNLTF GDVANKATLC SMKGCMRALV AQLKSESEDL
        550        560        570        580        590        600
  QQVIASVLRN LSWRADVNSK KTLREVGSVK ALMECALEVK KESTLKSVLS ALWNLSAHCT
        610        620        630        640        650        660
  ENKADICAVD GALAFLVGTL TYRSQTNTLA IIESGGGILR NVSSLIATNE DHRQILRENN
        670        680        690        700        710        720
  CLQTLLQHLK SHSLTIVSNA CGTLWNLSAR NPKDQEALWD MGAVSMLKNL IHSKHKMIAM
        730        740        750        760        770        780
  GSAAALRNLM ANRPAKYKDA NIMSPGSSLP SLHVRKQKAL EAELDAQHLS ETFDNIDNLS
        790        800        810        820        830        840
  PKASHRSKQR HKQSLYGDYV FDTNRHDDNR SDNFNTGNMT VLSPYLNTTV LPSSSSSRGS
        850        860        870        880        890        900
  LDSSRSEKDR SLERERGIGL GNYHPATENP GTSSKRGLQI STTAAQIAKV MEEVSAIHTS
        910        920        930        940        950        960
  QEDRSSGSTT ELHCVTDERN ALRRSSAAHT HSNTYNFTKS ENSNRTCSMP YAKLEYKRSS
        970        980        990       1000       1010       1020
  NDSLNSVSSS DGYGKRGQMK PSIESYSEDD ESKFCSYGQY PADLAHKIHS ANHMDDNDGE
       1030       1040       1050       1060       1070       1080
  LDTPINYSLK YSDEQLNSGR QSPSQNERWA RPKHIIEDEI KQSEQRQSRN QSTTYPVYTE
       1090       1100       1110       1120       1130       1140
  STDDKHLKFQ PHFGQQECVS PYRSRGANGS ETNRVGSNHG INQNVSQSLC QEDDYEDDKP
       1150       1160       1170       1180       1190       1200
  TNYSERYSEE EQHEEEERPT NYSIKYNEEK RHVDQPIDYS LKYATDIPSS QKQSFSFSKS
       1210       1220       1230       1240       1250       1260
  SSGQSSKTEH MSSSSENTST PSSNAKRQNQ LHPSSAQSRS GQPQKAATCK VSSINQETIQ
       1270       1280       1290       1300       1310       1320
  TYCVEDTPIC FSRCSSLSSL SSAEDEIGCN QTTQEADSAN TLQIAEIKEK IGTRSAEDPV
       1330       1340       1350       1360       1370       1380
  SEVPAVSQHP RTKSSRLQGS SLSSESARHK AVEFSSGAKS PSKSGAQTPK SPPEHYVQET
       1390       1400       1410       1420       1430       1440
```

Figure 3B

```
PLMFSRCTSV SSLDSFESRS IASSVQSEPC SGMVSGIISP SDLPDSPGQT MPPSRSKTPP
   1450       1460       1470       1480       1490       1500
PPPQTAQTKR EVPKNKAPTA EKRESGPKQA AVNAAVQRVQ VLPDADTLLH FATESTPDGF
   1510       1520       1530       1540       1550       1560
SCSSSLSALS LDEPFIQKDV ELRIMPPVQE NDNGNETESE QPKESNENQE KEAEKTIDSE
   1570       1580       1590       1600       1610       1620
KDLLDDSDDD DIEILEECII SAMPTKSSRK AKKPAQTASK LPPPVARKPS QLPVYKLLPS
   1630       1640       1650       1660       1670       1680
QNRLQPQKHV SFTPGDDMPR VYCVEGTPIN FSTATSLSDL TIESPPNELA AGEGVRGGAQ
   1690       1700       1710       1720       1730       1740
SGEFEKRDTI PTEGRSTDEA QGGKTSSVTI PELDDNKAEE GDILAECINS AMPKGKSHKP
   1750       1760       1770       1780       1790       1800
FRVKKIMDQV QQASASSSAP NKNQLDGKKK KPTSPVKPIP QNTEYRTRVR KNADSKNNLN
   1810       1820       1830       1840       1850       1860
AERVFSDNKD SKKQNLKNNS KDFNDKLPNN EDRVRGSFAF DSPHHYTPIE GTPYCFSRND
   1870       1880       1890       1900       1910       1920
SLSSLDFDDD DVDLSREKAE LRKAKENKES EAKVTSHTEL TSNQQSANKT QAIAKQPINR
   1930       1940       1950       1960       1970       1980
GQPKPILQKQ STFPQSSKDI PDRGAATDEK LQNFAIENTP VCFSHNSSLS SLSDIDQENN
   1990       2000       2010       2020       2030       2040
NKENEPIKET EPPDSQGEPS KPQASGYAPK SFHVEDTPVC FSRNSSLSSL SIDSEDDLLQ
   2050       2060       2070       2080       2090       2100
ECISSAMPKK KKPSRLKGDN EKHSPRNMGG ILGEDLTLDL KDIQRPDSEH GLSPDSENFD
   2110       2120       2130       2140       2150       2160
WKAIQEGANS IVSSLHQAAA AACLSRQASS DSDSILSLKS GISLGSPFHL TPDQEEKPFT
   2170       2180       2190       2200       2210       2220
SNKGPRILKP GEKSTLETKK IESESKGIKG GKKVYKSLIT GKVRSNSEIS GQMKQPLQAN
   2230       2240       2250       2260       2270       2280
MPSISRGRTM IHIPGVRNSS SSTSPVSKKG PPLKTPASKS PSEGQTATTS PRGAKPSVKS
   2290       2300       2310       2320       2330       2340
ELSPVARQTS QIGGSSKAPS RSGSRDSTPS RPAQQPLSRP IQSPGRNSIS PGRNGISPPN
   2350       2360       2370       2380       2390       2400
KLSQLPRTSS PSTASTKSSG SGKMSYTSPG RQMSQQNLTK QTGLSKNASS IPRSESASKG
   2410       2420       2430       2440       2450       2460
LNQMNNGNGA NKKVELSRMS STKSSGSESD RSERPVLVRQ STFIKEAPSP TLRRKLEESA
   2470       2480       2490       2500       2510       2520
SFESLSPSSR PASPTRSQAQ TPVLSPSLPD MSLSTHSSVQ AGGWRKLPPN LSPTIEYNDG
   2530       2540       2550       2560       2570       2580
RPAKRHDIAR SHSESPSRLP INRSGTWKRE HSKHSSSLPR VSTWRRTGSS SSILSASSES
   2590       2600       2610       2620       2630       2640
SEKAKSEDEK HVNSISGTKQ SKENQVSAKG TWRKIKENEF SPTNSTSQTV SSGATNGAES
   2650       2660       2670       2680       2690       2700
KTLIYQMAPA VSKTEDVWVR IEDCPINNPR SGRSPTGNTP PVIDSVSEKA NPNIKDSKDN
   2710       2720       2730       2740       2750       2760
QAKQNVGNGS VPMRTVGLEN RLNSFIQVDA PDQKGTEIKP GQNNPVPVSE TNESSIVERT
   2770       2780       2790       2800       2810       2820
PFSSSSSSKH SSPSGTVAAR VTPFNYNPSP RKSSADSTSA RPSQIPTPVN NNTKKRDSKT
```

Figure 3C

```
        2830       2840
DSTESSGTQS PKRHSGSYLV TSV*
```

FIG. 4A

```
APC    203  LGTCQDMEKRAQRRIARIQQIEKDILRIRQL  233
                 ::  ||  ||||||:|         |  |
RAL2   576  LTGAKGLQLRALRRIARIEQGGTAISPTSPL  606
```

FIG. 4B

```
APC       453  MKLSFDEEHRHAMNELGGLQAIAELLQVD  481
                :    ::||||| ::  :: :
M3 MAChR  249  LYWRIYKETEKRTKELAGLQASGTEAETE  277
                 | : | |   ::     |||||
MCC       220  LYPNLAEERSRWEKELAGLREENESLTAM  248
                ||:: ||:||     |
APC       453  MKLSFDEEHRHAMNELGGLQAIAELLQVD  481
```

FIG. 6A

```
GCA GTC GCC GCT CCA GTC TAT CCG GCA CTA GGA ACA GCC CCG GGN GGC GAG ACG      55
Ala Val Ala Ala Pro Val Tyr Pro Ala Leu Gly Thr Ala Pro Gly Gly Glu Thr     109

GTC CCC GCC ATG TCT GCG ATG GCC ATG AGG GAG AGG TTC GAC CGG TTC CAC GAG
Val Pro Ala MET Ser Ala MET Ala MET Arg Glu Arg Phe Asp Arg Phe His Glu     163

AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn     217

AGG AGC TTC ATC GCT CTT GGT GTC GGA CTG GCC TTG TAC CTG TAC CTG GTG TTC
Arg Ser Phe Ile Ala Leu Gly Val Gly Leu Ala Leu Tyr Leu Tyr Leu Val Phe     271

GGT TAT GGA GCC TCT CTC TGC AAC CTG ATA GGA TTT GGC TAC CCA GCC TAC
Gly Tyr Gly Ala Ser Leu Cys Asn Leu Ile Gly Phe Gly Tyr Pro Ala Tyr         325

ATC TCA ATT AAA GCT ATA GAG AGT CCC AAC AAA GAA GAT ACC CAG TGG CTG
Ile Ser Ile Lys Ala Ile Glu Ser Pro Asn Lys Glu Asp Thr Gln Trp Leu         379

ACC TAC TGG GTA GTG TAT GGT GTG TTC AGC ATT GCT GAA TTC TCT GAT ATC
Thr Tyr Trp Val Val Tyr Gly Val Phe Ser Ile Ala Glu Phe Ser Asp Ile         433

TTC CTG TCA TGG TTC CCC TAC TAC ATG CTG AAG TGT GGC TTG TTG TGG
Phe Leu Ser Trp Phe Pro Tyr Tyr MET Leu Lys Cys Gly Phe Leu Leu Trp         487

TGC ATG GCC CCG AGC CCT TCT AAT GGG GCT GAA CTG CTC TAC AAG CGC ATC ATC
Cys MET Ala Pro Ser Pro Ser Asn Gly Ala Glu Leu Leu Tyr Lys Arg Ile Ile     541

CGT CCT TTC TTC CTG AAG CAC GAG TCC CAG ATG GAC AGT GTG GTC AAG GAC CTT
Arg Pro Phe Phe Leu Lys His Glu Ser Gln MET Asp Ser Val Val Lys Asp Leu
```

FIG. 6B

```
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                568                                                595
                                                                   622

ACC GTG AAT TTA CTG GGT GAA GAA AAG AGC ACC TAA ACC AGA
Thr Val Asn Leu Leu Gly Glu Glu Lys Ser Thr
                                        622

CTAAACCAGA CTGGATGGAA ACTTCCTGCC CTCTCTGTAC CTTCCTACTG GAGCTTGATG TTATATTAGG
    640        650        660        670        680        690        700
GACTGTGGTA TAATTATTTT AATAATGTTG CCTTGGAAAC ATTTTTGAGA TATTAAAGAT TGGAATGTGT
    710        720        730        740        750        760        770
TGTAAGTTTC TTTGCTTACT TTTACTGTCT ATATATATAG GGAGCACTTT AAACTTAATG CAGTGGGCAG
    780        790        800        810        820        830        840
TGTCCACGTT TTTGGAAAAT GTATTTTGCC TCTGGGTAGG AAAAGATGTA TGTTGCTATC CTGCAGGAAA
    850        860        870        880        890        900        910
TATAAACTTA AAATAAAATT ATATACCCCA CAGGCTGTGT ACTTTACTGG GCTCTCCCTG CACGSATTTT
    920        930        940        950        960        970        980
CTCTGTAGTT ACATTAGGR TAATCTTTAT GGTTCTACTT CCTRTAATGT ACAATTTTAT ATAATTCNGR
    990       1000       1010       1020       1030       1040       1050
AATGTTTTTA ATGTATTTGT GCACATGTAC ATATGGAAAT GTTACTGTCT GACTACANCA TGCATCATGC
   1060       1070       1080       1090       1100       1110       1120
TCATGGGGAG GGAGCAGGGG AAGGTTGTAT GTGTCATTTA TAACTTCTGT ACAGTAAGAC CACCTGCCAA
   1130       1140       1150       1160       1170       1180       1190
AAGCTGGAGG AACCATTGTG CTGGTGTGGT CTACTAAATA ATACTTAGG AAATACGTGA TTAATATGCA
   1200       1210       1220       1230       1240       1250       1260
AGTGAACAAA GTGAGAAATG AAATCGAATG GAGATTGGCC TGGTTGTTTC CGTAGTATAT GGCATATGAA
   1270       1280       1290       1300       1310       1320       1330
   1340       1350       1360       1370       1380       1390       1400
```

FIG. 6C

| | | | | | |
|---|---|---|---|---|---|
| TACCAGGATA | GCTTTATAAA | GCAGTTAGTT | AGTTAGTTAC | TCACTCTAGT | GATAAATCGG | GAAATTTACA |
| 1410 | 1420 | 1430 | 1440 | 1450 | 1460 | 1470 |
| CACACACACA | CACACACACA | CACACACACA | CACACACACA | CACACACACA | GAGTACCCTG | TAACTCTCAA |
| 1480 | 1490 | 1500 | 1510 | 1520 | 1530 | 1540 |
| TTCCCTGAAA | AACTAGTAAT | ACTGTCTTAT | CTGCTATAAA | CTTTACATAT | TTGTCTATTG | TCAAGATGCT |
| 1550 | 1560 | 1570 | 1580 | 1590 | 1600 | 1610 |
| ACANTGGAMN | CCATTTCTGG | TTTTATCTTC | ANAGSGGAGA | NACATGTTGA | TTTAGTCTTC | TTTCCCAATC |
| 1620 | 1630 | 1640 | 1650 | 1660 | 1670 | 1680 |
| TTCTTTTTA | AMCCAGTTTN | AGGMNCTTCT | GRAGATTTGY | CCACCTCTGA | TTACATGTAT | GTTCTYGTTT |
| 1690 | 1700 | 1710 | 1720 | 1730 | 1740 | 1750 |
| GTATCATKAG | CAACAACATG | CTAATGRCGA | CACCTAGCTC | TRAGMGCAAT | TCTGGGAGAN | TGARAGGNWG |
| 1760 | 1770 | 1780 | 1790 | 1800 | 1810 | 1820 |
| TATARAGTMN | CCCATAATCT | GCTTGGCAAT | AGTTAAGTCA | ATCTATCTTC | AGTTTTTCTC | TGGCCTTTAA |
| 1830 | 1840 | 1850 | 1860 | 1870 | 1880 | 1890 |
| GGTCAAACAC | AAGAGGCTTC | CCTAGTTTAC | AAGTCAGAGT | CACTTGTAGT | CCATTTAAAT | GCCCTCATCC |
| 1900 | 1910 | 1920 | 1930 | 1940 | 1950 | 1960 |
| GTATTCTTTG | TGTTGATAAG | CTGCACAKGA | AGTACAGANC | AGTACAGTA | AGTAAAGTTA | ANNCGGATGT |
| 1970 | 1980 | 1990 | 2000 | 2010 | 2020 | 2030 |
| CTCCATTGAT | CTGCCAANTC | GNTATAGAGA | GCAATTGTC | TGGACTAGAA | AATCTGAGTT | TTACACCATA |
| 2040 | 2050 | 2060 | 2070 | 2080 | 2090 | 2100 |
| CTGTTAAGAG | TCCTTTTGAA | TTAAACTAGA | CTAAAACAAG | TGTATAACTA | AACTAACAAG | ATTAAATATC |
| 2110 | 2120 | 2130 | 2140 | 2150 | 2160 | 2170 |
| CAGCCAGTAC | AGTATTTTT | AAGGCAAATA | AAGATGATTA | GCTCACCTTG | AGNTAACAAT | CAGGTAAGAT |
| 2180 | 2190 | 2200 | 2210 | 2220 | 2230 | 2240 |
| CATNACAATG | TCTCATGATG | TNAANAATAT | TAAAGATATC | AATACTAAGT | GACAGTATCA | CNNCTAATAT |

FIG. 6D

```
2250        2260        2270        2280        2290        2300        2310
AATATGGATC  AGAGCATTTA  TTTGGGGAG   GAAAACAGTG  GTGATTACCG  GCATTTTATT  AAACTTAAAA
      2320        2330        2340        2350        2360        2370        2380
CTTTGTAGAA  AGCAAACAAA  ATTGTTCTTG  GGAGAAAATC  AACTTTTAGA  TTAAAAAAT   TTTAAGTAWC
      2390        2400        2410        2420        2430        2440        2450
TAGGAGTATT  TAAATCCTTT  TCCCATAAAT  AAAAGTACAG  TTTTCTTGGT  GGCAGAATGA  AAATCAGCAA
      2460        2470        2480        2490        2500        2510        2520
CNTCTAGCAT  ATAGACTATA  TAATCAGATT  GACAGCATAT  AGAATATATT  ATCAGACAAG  ATGAGGAGGT
      2530        2540        2550        2560        2570        2580        2590
ACAAAAGTTA  CTATTGCTCA  TAATGACTTA  CAGGCTAAAA  NTAGNTNTAA  AATACTATAT  TAAATTCTGA
      2600        2610        2620        2630        2640        2650        2660
ATGCAATTTT  TTTTGTTCC   CTTGAGACCA  AAATTTAAGT  TAACTGTTGC  TGGCAGTCTA  AGTGTAAATG
      2670        2680        2690        2700        2710        2720        2730
TTAACAGCAG  GAGAAGTTAA  GAATTGAGCA  GTTCTGTTGC  ATGATTCCC   AAATGAAATA  CTGCCTTGGC
      2740        2750        2760        2770        2780        2790        2800
TAGAGTTTGA  AAAACTAATT  GAGCCTGTGC  CTGGCTAGAA  AACAAGCGTT  TATTTGAATG  TGAATAGTGT
      2810        2820        2830        2840        2850        2860        2870
TTCAAAGGTA  TGTAGTTACA  GAATTCCTAC  CAAACAGCTT  AAATTCTTCA  AGAAAGAATT  CCTGCAGCAG
      2880        2890        2900        2910        2920        2930        2940
TTATTCCCTT  ACCTGAAGGC  TTCAATCATT  TGGATCAACA  ACTGCTACTC  TCGGGAAGAC  TCCTCTACTC
      2950        2960        2970        2980        2990        3000        3010
ACAGCTGAAG  AAAATGAGCA  CACCCTTCAC  ACTGTTATCA  CCTATCCTGA  AGATGTGATA  CACTGAATGG
      3020        3030        3040        3050        3060        3070        3080
AAATAAATAG  ATGTAAATAA  AATTGAGWTC  TCATTTAAAA  AAAACCATGT  GCCCAATGGG  AAAATGACCT
      3090        3100        3110        3120        3130        3140        3150
CATGTTGTGG  TTTAAACAGC  AACTGCACCC  ACTAGCACAG  CCCATTGAGC  TANCCTATAT  ATACATCTCT
      3160
GTCAGTGCCC  CTC
```

Figure 7A

```
 23  ATGGCTGCAGCTTCATATGATCAGTTGTTAAAGCAAGTTGAGGCACTGAAGATGGAGAAC    82

1   M  A  A  A  S  Y  D  Q  L  L  K  Q  V  E  A  L  K  M  E  N    20

83  TCAAATCTTCGACAAGAGCTAGAAGATAATTCCAATCATCTTACAAAACTGGAAACTGAG   142

21   S  N  L  R  Q  E  L  E  D  N  S  N  H  L  T  K  L  E  T  E    40

143  GCATCTAATATGAAGGAAGTACTTAAACAACTACAAGGAAGTATTGAAGATGAAGCTATG   202

41   A  S  N  M  K  E  V  L  K  Q  L  Q  G  S  I  E  D  E  A  M    60

203  GCTTCTTCTGGACAGATTGATTTATTAGAGCGTCTTAAAGAGCTTAACTTAGATAGCAGT   262

61   A  S  S  G  Q  I  D  L  L  E  R  L  K  E  L  N  L  D  S  S    80

263  AATTTCCCTGGAGTAAAACTGCGGTCAAAAATGTCCCTCCGTTCTTATGGAAGCCGGGAA   322

81   N  F  P  G  V  K  L  R  S  K  M  S  L  R  S  Y  G  S  R  E   100

323  GGATCTGTATCAAGCCGTTCTGGAGAGTGCAGTCCTGTTCCTATGGGTTCATTTCCAAGA   382

101   G  S  V  S  S  R  S  G  E  C  S  P  V  P  M  G  S  F  P  R   120

383  AGAGGGTTTGTAAATGGAAGCAGAGAAAGTACTGGATATTTAGAAGAACTTGAGAAAGAG   442
```

443  AGGTCATTGCTTCTTGCTGATCTTGACAAAGAAGAAAAGGAAAAAGACTGGTATTACGCT   502

141  R  S  L  L  A  D  L  D  K  E  E  K  E  D  W  Y  Y  A   160

503  CAACTTCAGAATCTCACTAAAAGAATAGATAGTCTTCCTTTAACTGAAAATTTTTCCTTA   562

161  Q  L  Q  N  L  T  K  R  I  D  S  L  P  L  T  E  N  F  S  L   180

563  CAAACAGATATGACCAGAAGGCAATTGGAATATGAAGCAAGGCAAATCAGAGTTGCGATG   622

181  Q  T  D  M  T  R  R  Q  L  E  Y  E  A  R  Q  I  R  V  A  M   200

623  GAAGAACAACTAGGTACCTGCCAGGATATGGAAAAACGAGCACAGCGAAGAATAGCCAGA   682

201  E  E  Q  L  G  T  C  Q  D  M  E  K  R  A  Q  R  R  I  A  R   220

683  ATTCAGCAAATCGAAAAGGACATACTTCGTATACGACAGCTTTTACAGTCCCAAGCAACA   742

221  I  Q  Q  I  E  K  D  I  L  R  I  R  Q  L  L  Q  S  Q  A  T   240

743  GAAGCAGAGAGGTCATCTCAGAACAAGCATGAAACCGGCTCACATGATGCTGAGCGGCAG   802

```
803   AATGAAGGTCAAGGAGTGGGAGAAATCAACATGGCAACTTCTGGTAATGGTCAGGGTTCA   862

261    N   E   G   Q   G   V   G   E   I   N   M   A   T   S   G   N   G   Q   G   S    280

863   ACTACACGAATGGACCATGAAACAGCCAGTGTTTTGAGTTCTAGTAGCACACACTCTGCA   922

281    T   T   R   M   D   H   E   T   A   S   V   L   S   S   S   T   H   S   A        300

923   CCTCGAAGGCTGACAAGTCATCTGGGAACCAAGgtggaaatggtgtattcattgttgtca   982

301    p   r   r   l   t   s   h   l   g   t   k   v   e   m   v   y   s   l   l   s    320

983   atgcttggtactcatgataaggatgatatgtcgcgaactttgctagctatgtctagctcc   1042

321    m   l   g   t   h   d   k   d   m   s   r   t   l   l   a   m   s   s            340

1043  caagacagctgtatatccatgcgacagtctggatgtcttcctctcctcatccagctttta  1102

341    q   d   s   c   i   s   m   r   q   s   g   c   l   p   l   l   i   q   l   l    360

1103  catggcaatgacaaagactctgtattgttgggaaattcccggggcagtaaagaggctcgg  1162

361    h   g   n   d   k   d   s   v   l   l   g   n   s   r   g   s   k   e   a   r    380

1163  gccagggccagtgcagcactccacaacatcattcactcacagcctgatgacaagagaggc  1222
```

1223  aggcgtgaaatccgagtccttcatcttttggaacagATACGCGCTTACTGTGAAACCTGT                          1282

401   r   r   e   i   r   v   l   h   l   l   e   q   I   R   A   Y   C   E   T   C      420

1283  TGGGAGTGGCAGGAAGCTCATGAACCAGGCATGGACCAGGACAAAAATCCAATGCCAGCT                          1342

421   W   E   W   Q   E   A   H   E   P   G   M   D   Q   D   K   N   P   M   P   A      440

1343  CCTGTTGAACATCAGATCTGTCCTGCTGTGTGTGTTCTAATGAAACTTTCATTTGATGAA                          1402

441   P   V   E   H   Q   I   C   P   A   V   C   V   L   M   K   L   S   F   D   E      460

1403  GAGCATAGACATGCAATGAATGAACTAGGGGGACTACAGGCCATTGCAGAATTATTGCAA                          1462

461   E   H   R   H   A   M   N   E   L   G   G   L   Q   A   I   A   E   L   L   Q      480

1463  GTGGACTGTGAAATGTACGGGCTTACTAATGACCACTACAGTATTACACTAAGACGATAT                          1522

481   V   D   C   E   M   Y   G   L   T   N   D   H   Y   S   I   T   L   R   R   Y      500

1523  GCTGGAATGGCTTTGACAAACTTGACTTTTGGAGATGTAGCCAACAAGGCTACGCTATGC                          1582

```
1583  TCTATGAAAGGCTGCATGAGAGCACTTGTGGCCCAACTAAAATCTGAAAGTGAAGACTTA  1642
 521   S   M   K   G   C   M   R   A   L   V   A   Q   L   K   S   E   S   E   D   L    540

1643  CAGCAGGTTATTGCAAGTGTTTTGAGGAATTTGTCTTGGCGAGCAGATGTAAATAGTAAA  1702
 541   Q   Q   V   I   A   S   V   L   R   N   L   S   W   R   A   D   V   N   S   K    560

1703  AAGACGTTGCGAGAAGTTGGAAGTGTGAAAGCATTGATGGAATGTGCTTTAGAAGTTAAA  1762
 561   K   T   L   R   E   V   G   S   V   K   A   L   M   E   C   A   L   E   V   K    580

1763  AAGGAATCAACCCTCAAAAGCGTATTGAGTGCCTTATGGAATTTGTCAGCACATTGCACT  1822
 581   K   E   S   T   L   K   S   V   L   S   A   L   W   N   L   S   A   H   C   T    600

1823  GAGAATAAAGCTGATATATGTGCTGTAGATGGTGCACTTGCATTTTTGGTTGGCACTCTT  1882
 601   E   N   K   A   D   I   C   A   V   D   G   A   L   A   F   L   V   G   T   L    620

1883  ACTTACCGGAGCCAGACAAACACTTTAGCCATTATTGAAAGTGGAGGTGGGATATTACGG  1942
 621   T   Y   R   S   Q   T   N   T   L   A   I   I   E   S   G   G   G   I   L   R    640
```

Figure 7F

```
1943  AATGTGTCCAGCTTGATAGCTACAAATGAGGACCACAGGCAAATCCTAAGAGAGAACAAC  2002

641   N  V  S  S  L  I  A  T  N  E  D  H  R  Q  I  L  R  E  N  N    660

2003  TGTCTACAAACTTTATTACAACACTTAAAATCTCATAGTTTGACAATAGTCAGTAATGCA  2062

661   C  L  Q  T  L  L  Q  H  L  K  S  H  S  L  T  I  V  S  N  A    680

2063  TGTGGAACTTTGTGGAATCTCTCAGCAAGAAATCCTAAAGACCAGGAAGCATTATGGGAC  2122

681   C  G  T  L  W  N  L  S  A  R  N  P  K  D  Q  E  A  L  W  D    700

2123  ATGGGGGCAGTTAGCATGCTCAAGAACCTCATTCATTCAAAGCACAAAATGATTGCTATG  2182

701   M  G  A  V  S  M  L  K  N  L  I  H  S  K  H  K  M  I  A  M    720

2183  GGAAGTGCTGCAGCTTTAAGGAATCTCATGGCAAATAGGCCTGCGAAGTACAAGGATGCC  2242

721   G  S  A  A  A  L  R  N  L  M  A  N  R  P  A  K  Y  K  D  A    740

2243  AATATTATGTCTCCTGGCTCAAGCTTGCCATCTCTTCATGTTAGGAAACAAAAAGCCCTA  2302

741   N  I  M  S  P  G  S  S  L  P  S  L  H  V  R  K  Q  K  A  L    760

2303  GAAGCAGAATTAGATGCTCAGCACTTATCAGAAACTTTTGACAATATAGACAATTTAAGT  2362
```

2363 CCCAAGGCATCTCATCGTAGTAAGCAGAGACACAAGCAAAGTCTCTATGGTGATTATGTT  2422

781  P  K  A  S  H  R  S  K  Q  R  H  K  Q  S  L  Y  G  D  Y  V   800

2423 TTTGACACCAATCGACATGATGATAATAGGTCAGACAATTTTAATACTGGCAACATGACT  2482

801  F  D  T  N  R  H  D  D  N  R  S  D  N  F  N  T  G  N  M  T   820

2483 GTCCTTTCACCATATTTGAATACTACAGTGTTACCCAGCTCCTCTTCATCAAGAGGAAGC  2542

821  V  L  S  P  Y  L  N  T  T  V  L  P  S  S  S  S  R  G  S      840

2543 TTAGATAGTTCTCGTTCTGAAAAAGATAGAAGTTTGGAGAGAGAACGCGGAATTGGTCTA  2602

841  L  D  S  S  R  S  E  K  D  R  S  L  E  R  E  R  G  I  G  L   860

2603 GGCAACTACCATCCAGCAACAGAAAATCCAGGAACTTCTTCAAAGCGAGGTTTGCAGATC  2662

861  G  N  Y  H  P  A  T  E  N  P  G  T  S  S  K  R  G  L  Q  I   880

2663 TCCACCACTGCAGCCCAGATTGCCAAAGTCATGGAAGAAGTGTCAGCCATTCATACCTCT  2722

```
2723 CAGGAAGACAGAAGTTCTGGGTCTACCACTGAATTACATTGTGTGACAGATGAGAGAAAT 2782

901  Q   E   D   R   S   S   G   S   T   T   E   L   H   C   V   T   D   E   R   N    920

2783 GCACTTAGAAGAAGCTCTGCTGCCCATACACATTCAAACACTTACAATTTCACTAAGTCG 2842

921  A   L   R   R   S   S   A   A   H   T   H   S   N   T   Y   N   F   T   K   S    940

2843 GAAAATTCAAATAGGACATGTTCTATGCCTTATGCCAAATTAGAATACAAGAGATCTTCA 2902

941  E   N   S   N   R   T   C   S   M   P   Y   A   K   L   E   Y   K   R   S   S    960

2903 AATGATAGTTTAAATAGTGTCAGTAGTAGTGATGGTTATGGTAAAAGAGGTCAAATGAAA 2962

961  N   D   S   L   N   S   V   S   S   D   G   Y   G   K   R   G   Q   M   K    980

2963 CCCTCGATTGAATCCTATTCTGAAGATGATGAAAGTAAGTTTTGCAGTTATGGTCAATAC 3022

981  P   S   I   E   S   Y   S   E   D   D   E   S   K   F   C   S   Y   G   Q   Y   1000

3023 CCAGCCGACCTAGCCCATAAAATACATAGTGCAAATCATATGGATGATAATGATGGAGAA 3082

1001  P   A   D   L   A   H   K   I   H   S   A   N   H   M   D   D   N   D   G   E   1020

3083 CTAGATACACCAATAAATTATAGTCTTAAATATTCAGATGAGCAGTTGAACTCTGGAAGG 3142
```

3143  CAAAGTCCTTCACAGAATGAAAGATGGGCAAGACCCAAACACATAATAGAAGATGAAATA  3202

1041  Q  S  P  S  Q  N  E  R  W  A  R  P  K  H  I  I  E  D  E  I  1060

3203  AAACAAAGTGAGCAAAGACAATCAAGGAATCAAAGTACAACTTATCCTGTTTATACTGAG  3262

1061  K  Q  S  E  Q  R  Q  S  R  N  Q  S  T  T  Y  P  V  Y  T  E  1080

3263  AGCACTGATGATAAACACCTCAAGTTCCAACCACATTTTGGACAGCAGGAATGTGTTTCT  3322

1081  S  T  D  D  K  H  L  K  F  Q  P  H  F  G  Q  Q  E  C  V  S  1100

3323  CCATACAGGTCACGGGGAGCCAATGGTTCAGAAACAAATCGAGTGGGTTCTAATCATGGA  3382

1101  P  Y  R  S  R  G  A  N  G  S  E  T  N  R  V  G  S  N  H  G  1120

3383  ATTAATCAAAATGTAAGCCAGTCTTTGTGTCAAGAAGATGACTATGAAGATGATAAGCCT  3442

1121  I  N  Q  N  V  S  Q  S  L  C  Q  E  D  D  Y  E  D  D  K  P  1140

3443  ACCAATTATAGTGAACGTTACTCTGAAGAAGAACAGCATGAAGAAGAAGAGAGACCAACA  3502

```
3503  AATTATAGCATAAAATATAATGAAGAGAAACGTCATGTGGATCAGCCTATTGATTATAGT  3562

1161   N  Y  S  I  K  Y  N  E  E  K  R  H  V  D  Q  P  I  D  Y  S   1180

3563  TTAAAATATGCCACAGATATTCCTTCATCACAGAAACAGTCATTTTCATTCTCAAAGAGT  3622

1181   L  K  Y  A  T  D  I  P  S  S  Q  K  Q  S  F  S  F  S  K  S   1200

3623  TCATCTGGACAAAGCAGTAAAACCGAACATATGTCTTCAAGCAGTGAGAATACGTCCACA  3682

1201   S  S  G  Q  S  S  K  T  E  H  M  S  S  S  E  N  T  S  T      1220

3683  CCTTCATCTAATGCCAAGAGGCAGAATCAGCTCCATCCAAGTTCTGCACAGAGTAGAAGT  3742

1221   P  S  S  N  A  K  R  Q  N  Q  L  H  P  S  S  A  Q  S  R  S   1240

3743  GGTCAGCCTCAAAAGGCTGCCACTTGCAAAGTTTCTTCTATTAACCAAGAAACAATACAG  3802

1241   G  Q  P  Q  K  A  A  T  C  K  V  S  S  I  N  Q  E  T  I  Q   1260

3803  ACTTATTGTGTAGAAGATACTCCAATATGTTTTTCAAGATGTAGTTCATTATCATCTTTG  3862

1261   T  Y  C  V  E  D  T  P  I  C  F  S  R  C  S  S  L  S  S  L   1280

3863  TCATCAGCTGAAGATGAAATAGGATGTAATCAGACGACACAGGAAGCAGATTCTGCTAAT  3922
```

3923  ACCCTGCAAATAGCAGAAATAAAAGAAAAGATTGGAACTAGGTCAGCTGAAGATCCTGTG  3982

1301  T  L  Q  I  A  E  I  K  E  K  I  G  T  R  S  A  E  D  P  V  1320

3983  AGCGAAGTTCCAGCAGTGTCACAGCACCCTAGAACCAAATCCAGCAGACTGCAGGGTTCT  4042

1321  S  E  V  P  A  V  S  Q  H  P  R  T  K  S  S  R  L  Q  G  S  1340

4043  AGTTTATCTTCAGAATCAGCCAGGCACAAAGCTGTTGAATTTTCTTCAGGAGCGAAATCT  4102

1341  S  L  S  S  E  S  A  R  H  K  A  V  E  F  S  S  G  A  K  S  1360

4103  CCCTCCAAAAGTGGTGCTCAGACACCCAAAAGTCCACCTGAACACTATGTTCAGGAGACC  4162

1361  P  S  K  S  G  A  Q  T  P  K  S  P  P  E  H  Y  V  Q  E  T  1380

4163  CCACTCATGTTTAGCAGATGTACTTCTGTCAGTTCACTTGATAGTTTTGAGAGTCGTTCG  4222

1381  P  L  M  F  S  R  C  T  S  V  S  S  L  D  S  F  E  S  R  S  1400

4223  ATTGCCAGCTCCGTTCAGAGTGAACCATGCAGTGGAATGGTAAGTGGCATTATAAGCCCC  4282

```
4283 AGTGATCTTCCAGATAGCCCTGGACAAACCATGCCACCAAGCAGAAGTAAAACACCTCCA 4342

1421   S  D  L  P  D  S  P  G  Q  T  M  P  P  S  R  S  K  T  P  P   1440

4343 CCACCTCCTCAAACAGCTCAAACCAAGCGAGAAGTACCTAAAAATAAAGCACCTACTGCT 4402

1441   P  P  P  Q  T  A  Q  T  K  R  E  V  P  K  N  K  A  P  T  A   1460

4403 GAAAAGAGAGAGAGTGGACCTAAGCAAGCTGCAGTAAATGCTGCAGTTCAGAGGGTCCAG 4462

1461   E  K  R  E  S  G  P  K  Q  A  A  V  N  A  A  V  Q  R  V  Q   1480

4463 GTTCTTCCAGATGCTGATACTTTATTACATTTTGCCACGGAAAGTACTCCAGATGGATTT 4522

1481   V  L  P  D  A  D  T  L  L  H  F  A  T  E  S  T  P  D  G  F   1500

4523 TCTTGTTCATCCAGCCTGAGTGCTCTGAGCCTCGATGAGCCATTTATACAGAAAGATGTG 4582

1501   S  C  S  S  S  L  S  A  L  S  L  D  E  P  F  I  Q  K  D  V   1520

4583 GAATTAAGAATAATGCCTCCAGTTCAGGAAAATGACAATGGGAATGAAACAGAATCAGAG 4642

1521   E  L  R  I  M  P  P  V  Q  E  N  D  N  G  N  E  T  E  S  E   1540

4643 CAGCCTAAAGAATCAAATGAAAACCAAGAGAAAGAGGCAGAAAAAACTATTGATTCTGAA 4702
```

4703  AAGGACCTATTAGATGATTCAGATGATGATGATATTGAAATACTAGAAGAATGTATTATT   4762

1561  K  D  L  L  D  D  S  D  D  D  D  I  E  I  L  E  E  C  I  I   1580

4763  TCTGCCATGCCAACAAAGTCATCACGTAAAGCAAAAAAGCCAGCCCAGACTGCTTCAAAA   4822

1581  S  A  M  P  T  K  S  S  R  K  A  K  K  P  A  Q  T  A  S  K   1600

4823  TTACCTCCACCTGTGGCAAGGAAACCAAGTCAGCTGCCTGTGTACAAACTTCTACCATCA   4882

1601  L  P  P  P  V  A  R  K  P  S  Q  L  P  V  Y  K  L  L  P  S   1620

4883  CAAAACAGGTTGCAACCCCAAAAGCATGTTAGTTTTACACCGGGGGATGATATGCCACGG   4942

1621  Q  N  R  L  Q  P  Q  K  H  V  S  F  T  P  G  D  D  M  P  R   1640

4943  GTGTATTGTGTTGAAGGGACACCTATAAACTTTTCCACAGCTACATCTCTAAGTGATCTA   5002

1641  V  Y  C  V  E  G  T  P  I  N  F  S  T  A  T  S  L  S  D  L   1660

5003  ACAATCGAATCCCCTCCAAATGAGTTAGCTGCTGGAGAAGGAGTTAGAGGAGGAGCACAG   5062

```
5063  TCAGGTGAATTTGAAAAACGAGATACCATTCCTACAGAAGGCAGAAGTACAGATGAGGCT  5122

1681   S   G   E   F   E   K   R   D   T   I   P   T   E   G   R   S   T   D   E   A   1700

5123  CAAGGAGGAAAAACCTCATCTGTAACCATACCTGAATTGGATGACAATAAAGCAGAGGAA  5182

1701   Q   G   G   K   T   S   S   V   T   I   P   E   L   D   D   N   K   A   E   E   1720

5183  GGTGATATTCTTGCAGAATGCATTAATTCTGCTATGCCCAAAGGGAAAAGTCACAAGCCT  5242

1721   G   D   I   L   A   E   C   I   N   S   A   M   P   K   G   K   S   H   K   P   1740

5243  TTCCGTGTGAAAAAGATAATGGACCAGGTCCAGCAAGCATCTGCGTCGTCTTCTGCACCC  5302

1741   F   R   V   K   K   I   M   D   Q   V   Q   Q   A   S   A   S   S   S   A   P   1760

5303  AACAAAAATCAGTTAGATGGTAAGAAAAAGAAACCAACTTCACCAGTAAAACCTATACCA  5362

1761   N   K   N   Q   L   D   G   K   K   K   P   T   S   P   V   K   P   I   P   1780

5363  CAAAATACTGAATATAGGACACGTGTAAGAAAAAATGCAGACTCAAAAAATAATTTAAAT  5422

1781   Q   N   T   E   Y   R   T   R   V   R   K   N   A   D   S   K   N   N   L   N   1800

5423  GCTGAGAGAGTTTTCTCAGACAACAAAGATTCAAAGAAACAGAATTTGAAAAATAATTCC  5482
```

5483  AAGGACTTCAATGATAAGCTCCCAAATAATGAAGATAGAGTCAGAGGAAGTTTTGCTTTT  5542

1821  K  D  F  N  D  K  L  P  N  N  E  D  R  V  R  G  S  F  A  F  1840

5543  GATTCACCTCATCATTACACGCCTATTGAAGGAACTCCTTACTGTTTTTCACGAAATGAT  5602

1841  D  S  P  H  H  Y  T  P  I  E  G  T  P  Y  C  F  S  R  N  D  1860

5603  TCTTTGAGTTCTCTAGATTTTGATGATGATGATGTTGACCTTTCCAGGGAAAAGGCTGAA  5662

1861  S  L  S  S  L  D  F  D  D  D  D  V  D  L  S  R  E  K  A  E  1880

5663  TTAAGAAAGGCAAAAGAAAATAAGGAATCAGAGGCTAAAGTTACCAGCCACACAGAACTA  5722

1881  L  R  K  A  K  E  N  K  E  S  E  A  K  V  T  S  H  T  E  L  1900

5723  ACCTCCAACCAACAATCAGCTAATAAGACACAAGCTATTGCAAAGCAGCCAATAAATCGA  5782

1901  T  S  N  Q  Q  S  A  N  K  T  Q  A  I  A  K  Q  P  I  N  R  1920

5783  GGTCAGCCTAAACCCATACTTCAGAAACAATCCACTTTTCCCCAGTCATCCAAAGACATA  5842

```
5843  CCAGACAGAGGGGCAGCAACTGATGAAAAGTTACAGAATTTTGCTATTGAAAATACTCCA  5902

1941   P   D   R   G   A   A   T   D   E   K   L   Q   N   F   A   I   E   N   T   P   1960

5903  GTTTGCTTTTCTCATAATTCCTCTCTGAGTTCTCTCAGTGACATTGACCAAGAAAACAAC  5962

1961   V   C   F   S   H   N   S   S   L   S   S   L   S   D   I   D   Q   E   N   N   1980

5963  AATAAAGAAAATGAACCTATCAAAGAGACTGAGCCCCCTGACTCACAGGGAGAACCAAGT  6022

1981   N   K   E   N   E   P   I   K   E   T   E   P   P   D   S   Q   G   E   P   S   2000

6023  AAACCTCAAGCATCAGGCTATGCTCCTAAATCATTTCATGTTGAAGATACCCCAGTTTGT  6082

2001   K   P   Q   A   S   G   Y   A   P   K   S   F   H   V   E   D   T   P   V   C   2020

6083  TTCTCAAGAAACAGTTCTCTCAGTTCTCTTAGTATTGACTCTGAAGATGACCTGTTGCAG  6142

2021   F   S   R   N   S   S   L   S   S   L   S   I   D   S   E   D   D   L   L   Q   2040

6143  GAATGTATAAGCTCCGCAATGCCAAAAAAGAAAAAGCCTTCAAGACTCAAGGGTGATAAT  6202

2041   E   C   I   S   S   A   M   P   K   K   K   P   S   R   L   K   G   D   N   2060

6203  GAAAAACATAGTCCCAGAAATATGGGTGGCATATTAGGTGAAGATCTGACACTTGATTTG  6262
```

6263  AAAGATATACAGAGACCAGATTCAGAACATGGTCTATCCCCTGATTCAGAAAATTTTGAT   6322

2081  K  D  I  Q  R  P  D  S  E  H  G  L  S  P  D  S  E  N  F  D   2100

6323  TGGAAAGCTATTCAGGAAGGTGCAAATTCCATAGTAAGTAGTTTACATCAAGCTGCTGCT   6382

2101  W  K  A  I  Q  E  G  A  N  S  I  V  S  S  L  H  Q  A  A  A   2120

6383  GCTGCATGTTTATCTAGACAAGCTTCGTCTGATTCAGATTCCATCCTTTCCCTGAAATCA   6442

2121  A  A  C  L  S  R  Q  A  S  S  D  S  D  S  I  L  S  L  K  S   2140

6443  GGAATCTCTCTGGGATCACCATTTCATCTTACACCTGATCAAGAAGAAAAACCCTTTACA   6502

2141  G  I  S  L  G  S  P  F  H  L  T  P  D  Q  E  E  K  P  F  T   2160

6503  AGTAATAAAGGCCCACGAATTCTAAAACCAGGGGAGAAAAGTACATTGGAAACTAAAAAG   6562

2161  S  N  K  G  P  R  I  L  K  P  G  E  K  S  T  L  E  T  K  K   2180

6563  ATAGAATCTGAAAGTAAAGGAATCAAAGGAGGAAAAAAAGTTTATAAAAGTTTGATTACT   6622

```
6623  GGAAAAGTTCGATCTAATTCAGAAATTTCAGGCCAAATGAAACAGCCCCTTCAAGCAAAC  6682

2201   G   K   V   R   S   N   S   E   I   S   G   Q   M   K   Q   P   L   Q   A   N   2220

6683  ATGCCTTCAATCTCTCGAGGCAGGACAATGATTCATATTCCAGGAGTTCGAAATAGCTCC  6742

2221   M   P   S   I   S   R   G   R   T   M   I   H   I   P   G   V   R   N   S   S   2240

6743  TCAAGTACAAGTCCTGTTTCTAAAAAAGGCCCACCCCTTAAGACTCCAGCCTCCAAAAGC  6802

2241   S   S   T   S   P   V   S   K   K   G   P   P   L   K   T   P   A   S   K   S   2260

6803  CCTAGTGAAGGTCAAACAGCCACCACTTCTCCTAGAGGAGCCAAGCCATCTGTGAAATCA  6862

2261   P   S   E   G   Q   T   A   T   T   S   P   R   G   A   K   P   S   V   K   S   2280

6863  GAATTAAGCCCTGTTGCCAGGCAGACATCCCAAATAGGTGGGTCAAGTAAAGCACCTTCT  6922

2281   E   L   S   P   V   A   R   Q   T   S   Q   I   G   G   S   S   K   A   P   S   2300

6923  AGATCAGGATCTAGAGATTCGACCCCTTCAAGACCTGCCCAGCAACCATTAAGTAGACCT  6982

2301   R   S   G   S   R   D   S   T   P   S   R   P   A   Q   Q   P   L   S   R   P   2320

6983  ATACAGTCTCCTGGCCGAAACTCAATTTCCCCTGGTAGAAATGGAATAAGTCCTCCTAAC  7042
```

7043  AAATTATCTCAACTTCCAAGGACATCATCCCCTAGTACTGCTTCAACTAAGTCCTCAGGT  7102

2341  K  L  S  Q  L  P  R  T  S  S  P  S  T  A  S  T  K  S  S  G  2360

7103  TCTGGAAAAATGTCATATACATCTCCAGGTAGACAGATGAGCCAACAGAACCTTACCAAA  7162

2361  S  G  K  M  S  Y  T  S  P  G  R  Q  M  S  Q  Q  N  L  T  K  2380

7163  CAAACAGGTTTATCCAAGAATGCCAGTAGTATTCCAAGAAGTGAGTCTGCCTCCAAAGGA  7222

2381  Q  T  G  L  S  K  N  A  S  S  I  P  R  S  E  S  A  S  K  G  2400

7223  CTAAATCAGATGAATAATGGTAATGGAGCCAATAAAAAGGTAGAACTTTCTAGAATGTCT  7282

2401  L  N  Q  M  N  N  G  N  G  A  N  K  K  V  E  L  S  R  M  S  2420

7283  TCAACTAAATCAAGTGGAAGTGAATCTGATAGATCAGAAAGACCTGTATTAGTACGCCAG  7342

2421  S  T  K  S  S  G  S  E  S  D  R  S  E  R  P  V  L  V  R  Q  2440

7343  TCAACTTTCATCAAAGAAGCTCCAAGCCCAACCTTAAGAAGAAAATTGGAGGAATCTGCT  7402

```
7403  TCATTTGAATCTCTTTCTCCATCATCTAGACCAGCTTCTCCCACTAGGTCCCAGGCACAA  7462

2461   S   F   E   S   L   S   P   S   S   R   P   A   S   P   T   R   S   Q   A   Q   2480

7463  ACTCCAGTTTTAAGTCCTTCCCTTCCTGATATGTCTCTATCCACACATTCGTCTGTTCAG  7522

2481   T   P   V   L   S   P   S   L   P   D   M   S   L   S   T   H   S   S   V   Q   2500

7523  GCTGGTGGATGGCGAAAACTCCCACCTAATCTCAGTCCCACTATAGAGTATAATGATGGA  7582

2501   A   G   G   W   R   K   L   P   P   N   L   S   P   T   I   E   Y   N   D   G   2520

7583  AGACCAGCAAAGCGCCATGATATTGCACGGTCTCATTCTGAAAGTCCTTCTAGACTTCCA  7642

2521   R   P   A   K   R   H   D   I   A   R   S   H   S   E   S   P   S   R   L   P   2540

7643  ATCAATAGGTCAGGAACCTGGAAACGTGAGCACAGCAAACATTCATCATCCCTTCCTCGA  7702

2541   I   N   R   S   G   T   W   K   R   E   H   S   K   H   S   S   L   P   R   2560

7703  GTAAGCACTTGGAGAAGAACTGGAAGTTCATCTTCAATTCTTTCTGCTTCATCAGAATCC  7762

2561   V   S   T   W   R   R   T   G   S   S   S   S   I   L   S   A   S   S   E   S   2580

7763  AGTGAAAAAGCAAAAAGTGAGGATGAAAAACATGTGAACTCTATTTCAGGAACCAAACAA  7822
```

7823  AGTAAAGAAAACCAAGTATCCGCAAAAGGAACATGGAGAAAAATAAAAGAAAATGAATTT   7882

2601  S K E N Q V S A K G T W R K I K E N E F   2620

7883  TCTCCCACAAATAGTACTTCTCAGACCGTTTCCTCAGGTGCTACAAATGGTGCTGAATCA   7942

2621  S P T N S T S Q T V S S G A T N G A E S   2640

7943  AAGACTCTAATTTATCAAATGGCACCTGCTGTTTCTAAAACAGAGGATGTTTGGGTGAGA   8002

2641  K T L I Y Q M A P A V S K T E D V W V R   2660

8003  ATTGAGGACTGTCCCATTAACAATCCTAGATCTGGAAGATCTCCCACAGGTAATACTCCC   8062

2661  I E D C P I N N P R S G R S P T G N T P   2680

8063  CCGGTGATTGACAGTGTTTCAGAAAAGGCAAATCCAAACATTAAAGATTCAAAAGATAAT   8122

2681  P V I D S V S E K A N P N I K D S K D N   2700

8123  CAGGCAAAACAAAATGTGGGTAATGGCAGTGTTCCCATGCGTACCGTGGGTTTGGAAAAT   8182

```
8183  CGCCTGAACTCCTTTATTCAGGTGGATGCCCCTGACCAAAAAGGAACTGAGATAAAACCA  8242

2721   R   L   N   S   F   I   Q   V   D   A   P   D   Q   K   G   T   E   I   K   P   2740

8243  GGACAAAATAATCCTGTCCCTGTATCAGAGACTAATGAAAGTTCTATAGTGGAACGTACC  8302

2741   G   Q   N   N   P   V   P   V   S   E   T   N   E   S   S   I   V   E   R   T   2760

8303  CCATTCAGTTCTAGCAGCTCAAGCAAACACAGTTCACCTAGTGGGACTGTTGCTGCCAGA  8362

2761   P   F   S   S   S   S   S   K   H   S   S   P   S   G   T   V   A   A   R   2780

8363  GTGACTCCTTTTAATTACAACCCAAGCCCTAGGAAAAGCAGCGCAGATAGCACTTCAGCT  8422

2781   V   T   P   F   N   Y   N   P   S   P   R   K   S   S   A   D   S   T   S   A   2800

8423  CGGCCATCTCAGATCCCAACTCCAGTGAATAACAACACAAAGAAGCGAGATTCCAAAACT  8482

2801   R   P   S   Q   I   P   T   P   V   N   N   N   T   K   K   R   D   S   K   T   2820

8483  GACAGCACAGAATCCAGTGGAACCCAAAGTCCTAAGCGCCATTCTGGGTCTTACCTTGTG  8542

2821   D   S   T   E   S   S   G   T   Q   S   P   K   R   H   S   G   S   Y   L   V   2840

8543  ACATCTGTTTAA                                                  8554
```

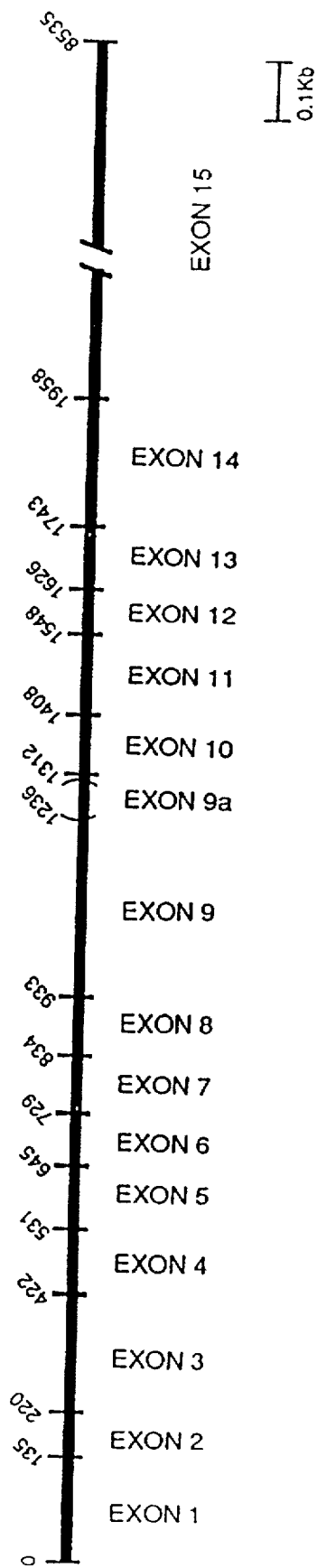

FIG. 8B-2

| Left flanking sequence | Exon | Right flanking sequence |
|---|---|---|
| TAGTCTAAATTATACCATCTATAATGTGCTTAATTTTTAG | EXON 8   99 nt. | GTAACAGAAGATTACAAACCCTGGTCACTAATGCCATGAC |
| TAAAGTCGTAATTTGTTTCTAAACTCATTGGCCCACAG | EXON 9   379 nt. | GTATGTTCTCTATAGTGTACATCGTAGTGCATGTTTCAAA |
| ATAACAAAGCATTATGGTTTATGTTGATTTTATTTTCAG | EXON 10  96 nt. | GTAAGACAAAAATGTTTTTAAATGACATAGACAATTACTG |
| TTAGATGATTGTCTTTTTCCCTCTTGCCCTTTTAAATTAG | EXON 11  140 nt. | GTATGTTTTTATAACATGTATTTCTTAAGATAGCTCAGGT |
| TGNCTTTTAAATGATCCCTCTATTCTGTATTAATTTACAG | EXON 12  78 nt. | GTACTATTAGAATTTCACCTGTTTTCTTTTTTCTCTTT |
| ATTTTATGTATAAATTAATCTAAAATTGATTAATTTCCAG | EXON 13  117 nt. | GTACCTTTGAAAACATTAGTACTATATATGAATTTCAT |
| CCAACTCNAATTAGATGACCCATATTCTGTTTCTTACTAG | EXON 14  215 nt. | GTATATATAGAGTTTTATATTACTTTTAAAGTACAGAATT |
| ATTGTGACCTTAATTTTGTGATCTCTCTTGATTTATTTCAG | EXON 15 | |

APC (ADENOMATOUS *POLYOSIS COLI*) PROTEIN

This application is a division of application Ser. No. 08/289,548, filed Aug. 12, 1994, which is a division of application Ser. No. 07/741,940 filed Aug. 8, 1991 U.S. Pat. No. 5,352,775.

The U.S. Government has a paid-up license in this invention and the right in limited circumstances to require the patent owner to license others on reasonable terms as provided for by the terms of grants awarded by the National Institutes of Health.

TECHNICAL AREA OF THE INVENTION

The invention relates to the area of cancer diagnostics and therapeutics. More particularly, the invention relates to detection of the germline and somatic alterations of wild-type APC genes. In addition, it relates to therapeutic intervention to restore the function of APC gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB (retinalbastoma), p53, (53 KD protoi) DCC (deleted in colarectal cancer) and MCC (mutated in colarectal cancer), were found to be deleted or altered in many cases of the tumors studied. Baker et al., Science, Vol. 244, p. 217 (1989); Fearon et al., Science, Vol. 247, p. 49 (1990); Kinzler et al. Science Vol. 251, p. 1366 (1991).)

In order to fully understand the pathogenesis of tumors, it will be necessary to identify the other suppressor genes that play a role in the tumorigenesis process. Prominent among these is the one(s) presumptively located at 5q21. Cytogenetic (Herrera et al., *Am J. Med. Genet.*, Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmoid tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research, Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in both sporadic and familial tumors.

Although the MCC gene has been identified on 5q21 as a candidate suppressor gene, it does not appear to be altered in FAP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lost said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object of the invention to provide a preparation of the human APC protein.

It is another object of the invention to provide a method of screening for genetic predisposition to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products from the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provided for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene coding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in FIG. 3A–3C or 7A–7W (SEQ ID NOS:7 and 2.

In yet another embodiment of the invention a method is provided for screening for genetic predisposition to cancer, including familial adenomatous polyposis (FAP) and Gardner's Syndrome (GS), in a human. The method comprises: detecting among kindred persons the presence of a DNA polymorphism which is linked to a mutant APC allele in an individual having a genetic predisposition to cancer, said kindred being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenic animals are provided. The animals carry a mutant APC allele from a second animal species or have been genetically engineered to contain an insertion mutation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colorectal cancers, Gardner's Syndrome, as well as the less severe familial polyposis discusses above.

BRIEF DESCRIPTION OF THE DRAWINGS

FIGS. 2A and 2B show the sequence of TB1 (SEQ ID NO:5) and TB2 (SEQ ID NO:6) genes, respectively. The cDNA sequence of the TB1 gene was determined from the analysis of 11 cDNA clones derived from normal colon and liver, as described in the text. A total of 2314 bp were contained within the overlapping cDNA clones, defining an ORF (open reading from) of 424 amino acids beginning at nucleotide 1. Only the predicted amino acids from the ORF are shown. The carboxy-terminal end of the ORF has apparently been identified, but the 5' end of the TB1 transcript has not yet been precisely determined.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

Figure 3C:
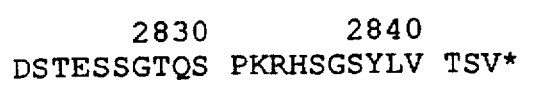

FIG. 3A–3C shows the sequence of the APC gene product (SEQ ID NO:7). The cDNA sequence was determined through the analysis of 87 cDNA clones derived from normal colon, liver, and brain. A total of 8973 bp were contained within overlapping cDNA ciones, defining an ORF of 2843 amino acids. In frame stop codons surrounded this ORF, as described in the text, suggesting that the entire APC gene product was represented in the ORF illustrated. Only the predicted amino acids are shown.

FIG. 4A shows the local similarity between human APC (SEQ ID NO:2) and ral2 (SEQ ID NO:8) of yeast. Local similarity among the APC (SEQ ID NO:2) and MCC genes (SEQ ID NO:10) and the m3 muscarinic acetylcholine receptor (SEQ ID NO:9) is shown in FIG. 4B. The region of the mAChR shown corresponds to that responsible for coupling the receptor to G proteins. The connecting lines indicate identities; dots indicate related amino acids residues.

Figure 5:
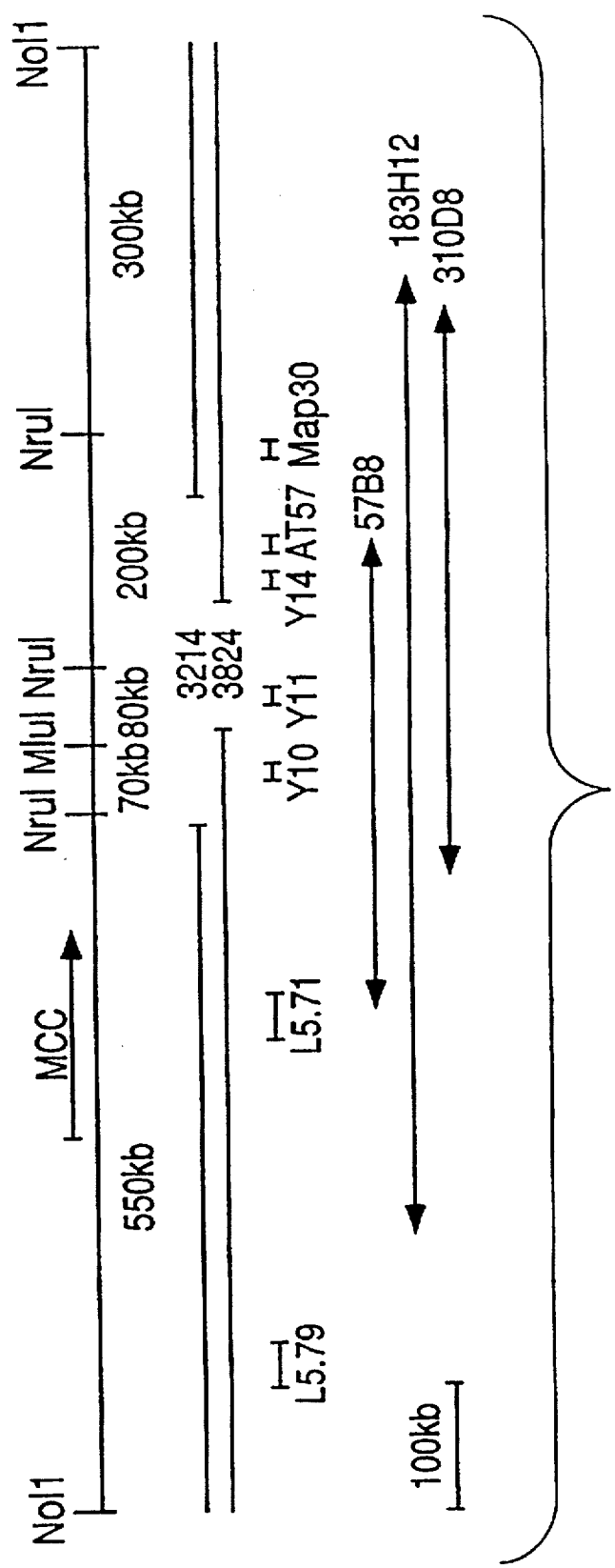

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are indicated above the map.

FIG. 6 shows the DNA sequence (SEQ ID NO:3) and predicted amino acid sequence of DPI (TB2) (SEQ ID NO:4). The nucleotide numbering begins at the most 5' nucleotide isolated. A proposed initiation methionine (base 77) is indicated in bold type. The entire coding sequence is presented.

FIG. 7A–7W shows the cDNA (SEQ ID NO:1) and predicted amino acid sequence of DP2.5 (APC) (SEQ ID NO:2). The nucleotide numbering begins at the proposed initiation methionine. The nucleotides and amino acids of the alternatively spliced exon (exon 9; nucleotide positions 937–1259) are presented in lower case letters. At the 3' end, a poly(A) addition signal occurs at 9530, and one cDNA clone has a poly(A) at 9563. Other cDNA clones extend beyond 9563, however, and their consensus sequence is included here.

Figures 1, 8B:
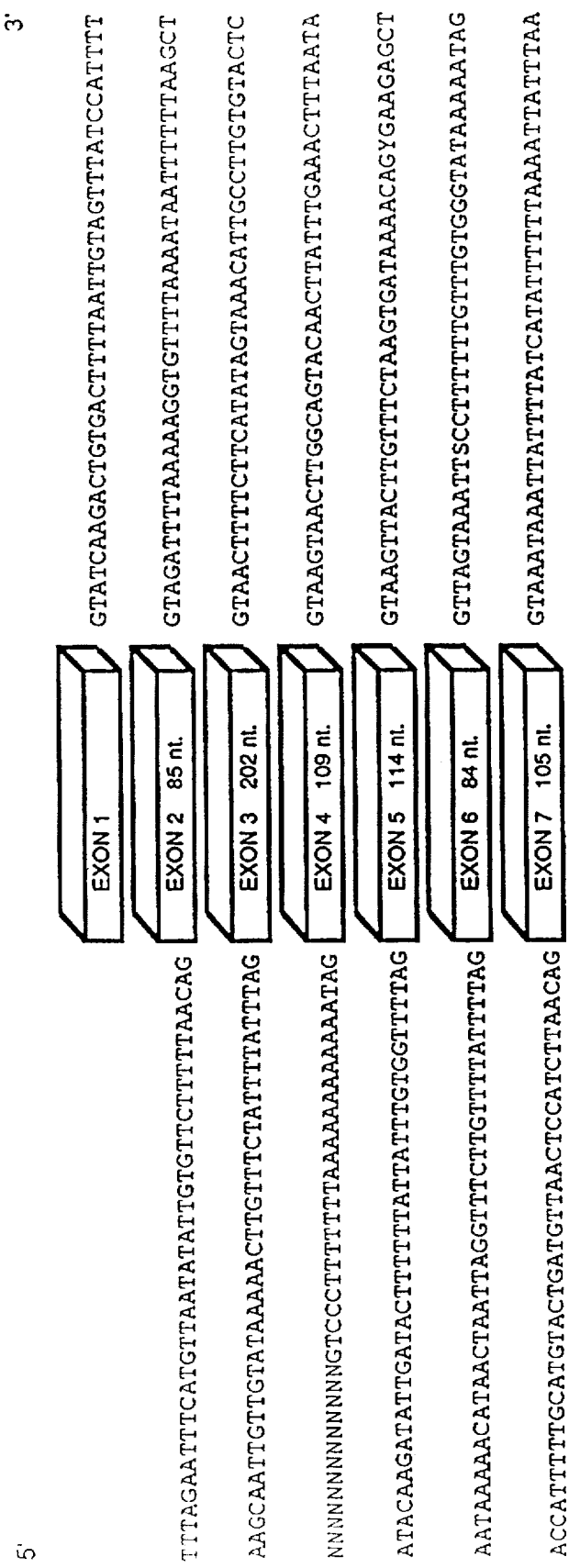
FIG. 1A shows an overview of yeast artificial chromosome (YAC) contigs (contigeous DNA segment). Genetic distances between selected RFLP markers from within the contigs are shown in centiMorgans.

FIG. 8A–8B shows the arrangement of exons in DP2.5 (APC). Exon 9 corresponds to nucleotides 933–1312; exon 9a corresponds to nucleotides 1236–1312. The stop codon in the cDNA is at nucleotide 8535. FIG. 8B Partial intronic sequence surrounding each exon is shows (SEQ ID NOS: 11–38). 5' intron sequences of exons 2, 3, 4, 5, 6, 7, 8, 9, 10, 11, 12, 13, 14, and 15 are shown in SEQ ID NOS: 12, 14, 16, 18, 20, 22, 24, 26, 28, 30, 32, 34, 36, 38, respectively. 3' intron sequences of exons 1, 2, 3, 4, 5, 6, 7, 8, 9, 10, 11, 12, 13, and 14 are shown in SEQ ID NOS: 11, 13, 15, 17, 19, 21, 23, 25, 27, 29, 31, 33, 35, 37, respectively.

DETAILED DESCRIPTION

It is a discovery of the present invention that mutational events associated with tumorigenesis occur in a previously unknown gene on chromosome 5q named here the APC (Adenomatous Polyposis Coli) gene. Although it was previously known that deletion of alleles on chromosome 5q were common in certain types of cancers, it was not known that a target gene of these deletions was the APC gene. Further it was not known that other types of mutational events in the APC gene are also associated with cancers. The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations— including deletions. The alteration may be due to either rearrangements such as insertions, inversions, and deletions, or to point mutations. Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatically mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. No. 4,683,203; and U.S. Pat. No. 4,683,195. Specific primers which can be used in order to amplify the gene will be discussed in more detail below. The ligase chain reaction, which is known in the art, can also be used to amplify APC sequences. See Wu et al., Genomics, Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ARMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindred persons of an affected individual for the presence of the APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Alteration of wild-type genes can also be detected on the basis of the alteration of a wild-type expression product of the gene. Such expression products include both the APC mRNA as well as the APC protein product. The sequences of these products are shown in FIGS. 3A–3C and 7A–7C. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type APC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the APC mRNA or gene but can be a segment of either. If the riboprobe comprises only a segment of the APC mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the APC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the APC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the tumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gene.

Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC genes or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene on chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the APC open reading frame shown in FIG. 7A–7W (SEQ ID NO:1), design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the APC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nucleic acid probes is used to compose a kit for detecting alteration of wild-type APC genes. The kit allows for hybridization to the entire APC gene. The probes may overlap with each other or be contiguous.

If a riboprobe is used to detect mismatches with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, calorimetric, or fluorometric material, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the APC gene. These are useful to detect similar mutations in other patients on the basis of hybridization rather than mismatches. These are discussed above and referred to as allele-specific probes. As mentioned above, the APC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes. Provided with the APC coding sequence shown in FIG. 7A-7B (SEQ ID NO:1), design of particular probes is well within the skill of the ordinary artisan.

According to the present invention a method is also provided of supplying wild-type APC function to a cell which carries mutant APC alleles. Supplying such function should suppress neoplastic growth of the recipient cells. The wild-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes both for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type APC gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed phenotype of the cell will be determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant APC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in FIG. 3A-3C and 7A-7B (SEQ ID NO:207). Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or in vitro.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells, or amniotic fluid for mutations of the APC gene. Alteration of a wildtype APC allele, whether for example, by point mutation or by deletion, can be detected by any of the means discussed above.

Molecules of cDNA according to the present invention are intron-free, APC gene coding molecules. They can be made by reverse transcriptase using the APC mRNA as a template. These molecules can be propagated in vectors and cell lines as is known in the art. Such molecules have the sequence shown in SEQ ID NO: 7. The cDNA can also be made using the techniques of synthetic chemistry given the sequence disclosed herein.

A short region of homology has been identified between APC and the human m3 muscarinic acetylcholine receptor (mAChR). This homology was largely confined to 29 residues in which 6 out of 7 amino acids (EL(GorA)GLQA) were identical (See FIG. 4 (SEQ ID NO:9)). Initially, it was not known whether this homology was significant, because many other proteins had higher levels of global homology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mAChR at the analogous protein position. These 21 residues overlap the 19 amino acid homology between APC and m3 mAChR.

This connection between APC and the G protein activating region of mAChR is intriguing in light of previous investigations relating G proteins to cancer. For example, the RAS oncogenes, which are often mutated in colorectal cancers (Vogelstein, et al., N. Engl. J. Med., Vol. 319, p. 525 (1988); Bos et al., Nature Vol. 327, p. 293 (1987)), are members of the G protein family (Bourne, et al., Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, Vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindac. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg., 157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in normal colon cells and in colorectal, lung, ad bladder tumors.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Figures 1, 1B, 2:
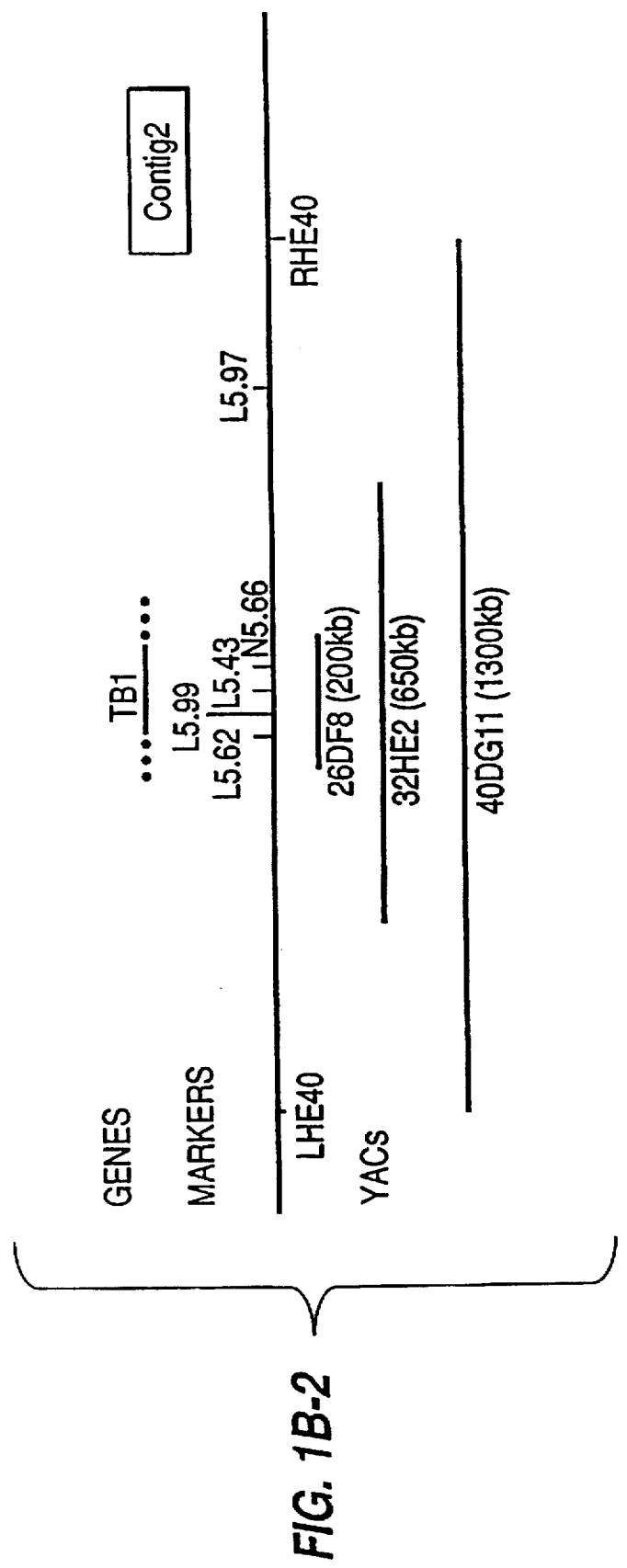
FIG. 1B shows a detailed map of the three central contigs. The position of the six identified genes from within the FAP region is shown; the 5' and 3' ends of the transcripts from these genes have in general not yet been isolated, as indicated by the string of dots surrounding the bars denoting the genes, positions. Selected restriction endonuclease recognition sites are indicated. B. BssH2; S. SstII; M. MluI; N. NruI.
Figures 1, 1B, 2, 3:
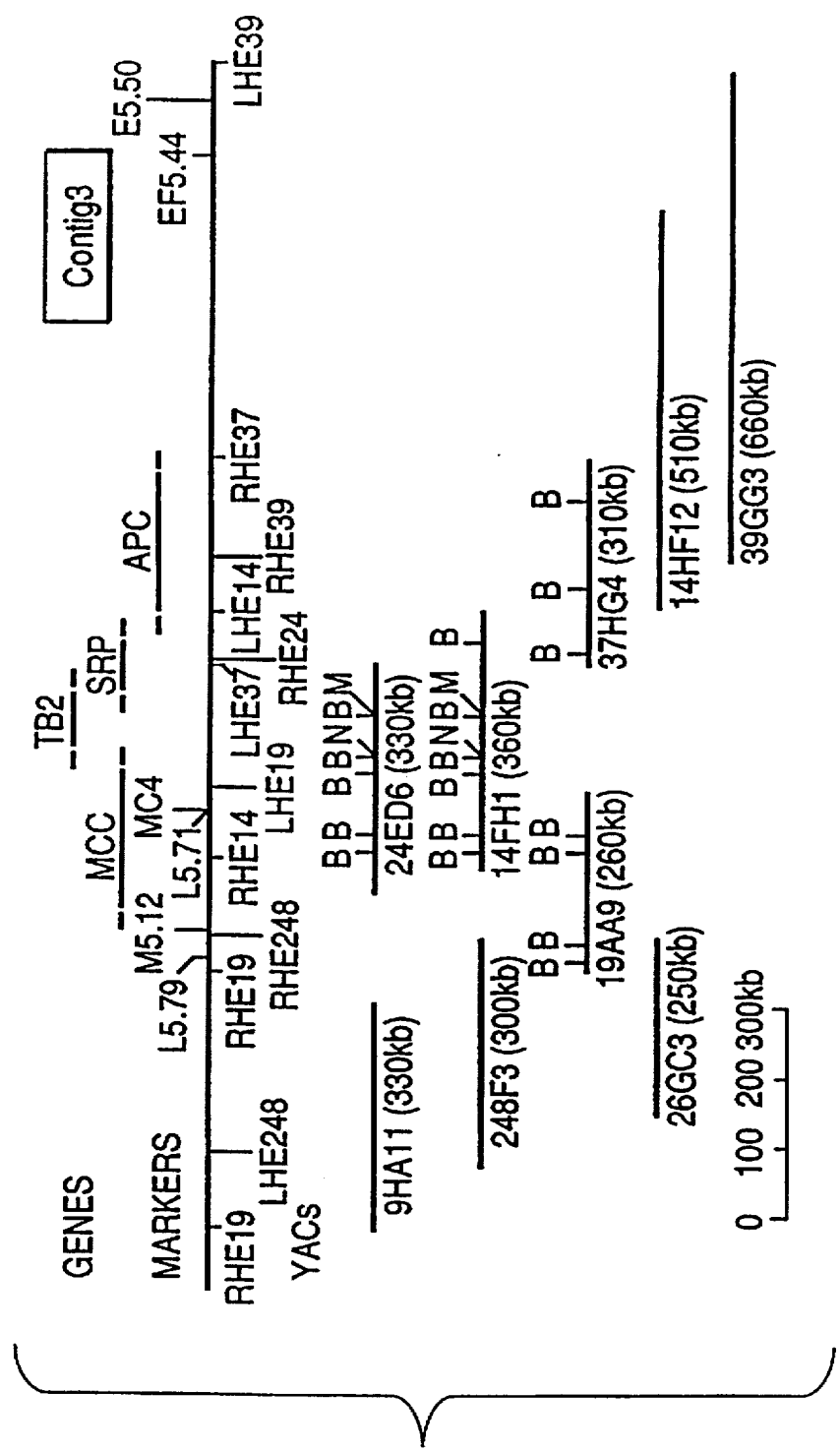

Three contigs encompassing approximately 4 Mb were contained within the central portion of this region. The YAC's constituting these contigs, together with the markers used for their isolation and orientations, are shown in FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in microtiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleic Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACS. The termini of the 28EC1 YAC were sequenced to derive markers RHE28 and LHE28, respectively. The sequences of these two markers were then used to isolate YAC clones 15CH12 (from RHE28) and 40CFI and 29EF1 (from LHE28). These five YAC's formed a contig encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC 39GQ3 allowed connection of the initial contig 3 clones through YAC 37HG4 (FIG. 1B). YAC37HG4 was deposited at the National Collection of Industrial and Marine Bacteria (NCIMB), P.O. Box 31, 23 St. Machar Drive, Aberdeen AB2 1RY, Scotland, under Accession No. 4035A, FB3 on Dec. 17, 1990.

Multipoint linkage analysis with the various markers used to define the contigs, combined with PFGE analysis, showed that contigs 1 and 2 were centromeric to contig 3. These contigs were used as tools to orient and/or identify genes which might be responsible for FAP. Six genes were found to lie within this cluster of YAC's, as follows:

Contig #1: FER—The FER gene was discovered through its homology to the viral oncogene ABL (Hao et al., supra). It has an intrinsic tyrosine kinase activity, and in situ hybridization with an FER probe showed that the gene was located at 5q11-23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human genomic DNA. Thus, the YAC mapping results were consistent with the FER linkage data and PFGE analyses.

Contig 2: TB1—TB1 was identified through a cross-hybridization approach. Exons of genes are often evolutionarily conserved while introns and intergenic regions are much less conserved. Thus, if a human probe cross-hybridizes strongly to the DNA from non-primate species, there is a reasonable chance that it contains exon sequences. Subclones of the cosmids shown in FIG. 1 were used to screen Southern blots containing rodent DNA samples. A subclone of cosmid N5.66 (p 5.66–4) was shown to strongly hybridize to rodent DNA, and this clone was used to screen cDNA libraries derived from normal adult colon and fetal liver. The ends of the initial cDNA clones obtained in this screen were then used to extend the cDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids (SEQ ID NO:5). The product of this gene was not globally homologous to any other sequence in the current database but showed two significant local similarities to a family of ADP, ATP carrier/translocator proteins and mitochondrial brown fat uncoupling proteins which are widely distributed from yeast to mammals. These conserved regions of TB1 (underlined in FIG. 2A) may define a predictive motif for this sequence family. In addition, TB1 appeared to contain a signal peptide (or mitochondrial targeting sequence) as well as at least 7 transmembrane domains.

Contig 3: MCC, TB2, SRP and APC—The MCC gene was also discovered through a cross-hybridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the coding region of MCC was approximately 50 kb proximal to the centromeric end of a 200 kb deletion found in an FAP patient. MCC cDNA probes detected a 10 kb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a CDNA library from normal colon. One of the cDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (SEQ ID NO:6) (FIG. 2B). The gene detected by YS39 was named TB2. Searches of nucleotide and protein databases revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. Five of these clones were deposited at the American Type Culture Collection, 1230 Parklawn Drive, Rockville Md., 20852, on Jun. 25, 1997. These clones bear the laboratory designations: FB9A, FB97A, FB70B, FB64A, and FB54D. The gene corresponding to this transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14FH1. However, the 3' end of the APC gene was found in 14FH1 as well as 37HG4. Analogously, the 5' end of the MCC coding region was found in YAC clones 19AA9 and 26GC3 but not 24ED6 or 14FH1, while the 3' end displayed the opposite pattern. Thus, MCC and APC transcription units pointed in opposite directions, with the direction of transcription going from centromeric to telomeric in the case of MCC, and telomeric to centromeric in the case of APC. PFGE analysis of YAC DNA digested with various restriction endonucleases showed that TB2 and SRP were between MCC and APC, and that the 3' ends of the coding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain 2,843 amino acids FIGS. 3A–3C (SEQ ID NO:7). The results of database searching with the APC gene product were quite complex due to the presence of large segments with locally biased amino acid compositions. In spite of this, APC could be roughly divided into two domains. The N-terminal 25% of the protein had a high content of leucine residues (12%) and showed local sequence similarities to myosins, various intermediate filament proteins (e.g., desmin, vimentin, neurofilaments) and Drosophila armadillo/human plakoglobin. The latter protein is a component of adhesive junctions (desmosomes) joining epithelial cells (Franke et al., Proc. Natl. Acad. Sci. U.S.A., Vol. 86, p. 4027 (1989); Perfer et al., Cell, Vol. 63, p. 1167 (1990)) The C-terminal 75% of APC (residues 731–2832) is 17% serine by composition with serine residues more or less uniformly distributed. This large domain also contains local concentrations of charged (mostly acidic) and proline residues. There was no indication of potential signal peptides, transmembrane regions, or nuclear targeting signals in APC, suggesting a cytoplasmic localization.

To detect short similarities to APC, a database search was performed using the PAM-40 matrix (Altschul, J. Mol. Bio., Vol. 219, p. 555 (1991). Potentially interesting matches to several proteins were found. The most suggestive of these involved the ral2 gene product of yeast, which is implicated in the regulation of ras activity (Fukul et al., Mol. Cell. Biol., Vol. 9, p. 5617 (1989)). Little is known about how ral2 might interact with ras but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both are implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "spacer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of APC. The potential for both APC and MCC to form coiled coils is interesting in that such structures often mediate homo- and hetero-oligomerization.

Finally, it had previously been noted that MCC shared a short similarity with the region of the m3 muscarinic acetylcholine receptor (mAChR) known to regulate specificity of G-protein coupling. The APC gene also contained a local similarity to the region of the m3 mAChR FIG. (SEQ ID NO:9) that overlapped with the MCC similarity (SEQ ID NO:10) (FIG. 4B). Although the similarities to ra12 (SEQ ID NO:8) (FIG. 4A) and m3 mAChR (SEQ ID NO:9) (FIG. 4B) were not statistically significant, they were intriguing in light of previous observations relating G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER, TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-AGAAGGATCCCTTGTGCAGTGTGGA-3' (SEQ ID NO:95) and 5'-GACAGGATCCTGAAGCTGAGTTTG-3' (SEQ ID NO:96). The underlined nucleotides were altered from the true FER sequence to create BamHI sites. The cell lines used were JW and Difi, both derived from colorectal cancers of FAP patients. (C. Paraskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequenced in their entirety. The PCR products were cloned in the BamHI site of Bluescript SK (Stratagene) and pools of at least 50 clones were sequenced en masse using T7 polymerase, as described in Nigro et al., Nature 342, 705 (1989).

Only a single conservative amino acid change (GTG→CTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' (SEQ ID NO:97) and 5'-GGAATAATTAGGTCTCCAA-3' (SEQ ID NO:98). PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and APC in FAP and sporadic colorectal tumors. Each of these genes is linked and encompassed by contig 3 (see FIG. 1).

Several lines of evidence suggested that this contig was of particular interest. First, at least three of the four genes in this contig were within the deleted region identified in two FAP patients. (See Example 5 infra.) Second, allelic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with sporadic CRC. Only two examples of somatic changes were observed in over 200 tumors studied: a rearrangement/deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of contig 3 genes in patients with FAP. We chose to examine MCC and APC, rather than TB2 or SRP, because of the somatic mutations in MCC and APC noted above. To facilitate the identification of subtle alterations, the genomic sequences of MCC and APC exons were determined (see Table I SEQ ID NO:24–38). These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions, approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the APC gene. The three exons examined included those containing nt 822–930, 931–1309, and the first 300 nt of the most distal exon (nt 1956–2256). PCR and RNase protection analysis were performed as described in Kinzler et al. supra, using the primers underlined in Table I (SEQ ID NO:24–38). The primers for nt 1956–2256 were 5'-GCAAATCCTAAGAGAGAACAA-3' (SEQ ID NO:99) and 5'-GATGGCAAGCTTGAGCCAG-3'(SEQ ID NO:100).

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nucleic Acids Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demonstrated the same abnormal RNase protection pattern indicated that both had a C to T transition at codon 301 that resulted in a change from arginine (CGA) to a stop codon (TGA). This change was not present in 200 individuals without FAP. As this point mutation resulted in the predicted loss of the recognition site for the enzyme Taq I, appropriate PCR products could be digested with Taq I to detect the mutation. This allowed us to determine that the stop codon co-segregated with disease phenotype in members of the family of P24. The inheritance of this change in affected members of the pedigree provides additional evidence for the importance of the mutation.

Cloning and sequencing of the PCR product from FAP patient P93 indicated a C to G transversion at codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9. In addition to these germline mutations, we identified several somatic mutations of MCC and APC in sporadic CRC'S. Seventeen MCC exons were examined in 90 sporadic colorectal cancers by RNase protection analysis. In each case where an abnormal RNase protection pattern was observed, the corresponding PCR products were cloned and sequenced. This led to the identification of six point mutations (two described previously) (Kinzler et al., supra), each of which was not found in the germline of these patients (Table IIB). Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822–930, 931–1309, and 1406–1545 (Table I). A total of three mutations were identified, each of which proved to be somatic. Tumor T27 contained a somatic mutation of CGA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codon (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Biochem. Biophys. Res. Comm. 130, 118 (1985). PCR was performed as described previously using the primers 5'-GTTCCAGCAGTGTCACAG-3' (SEQ ID NO:101) and 5'-GGGAGATTTCGCTCCTGA-3' (SEQ ID NO:102). A PCR product containing codon 1338 was amplified from the archival DNA and used to show that the stop codon represented a somatic mutation present in the original primary tumor and in cell lines derived from the primary and metastatic tumor sites, but not from normal tissue of the patient.

The ten point mutations in the MCC and APC genes so far discovered in sporadic CRCs are summarized in Table IIB.

Analysis of the number of mutant and wild-type PCR clones obtained from each of these tumors showed that in eight of the ten cases, the wild-type sequence was present in approximately equal proportions to the mutant. This was confirmed by RFLP analysis using flanking markers from chromosome 5q which demonstrated that only two of the ten tumors (T135 and T201) exhibited an allelic deletion on chromosome 5q. These results are consistent with previous observations showing that 20–40% of sporadic colorectal tumors had allelic deletions of chromosome 5q. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that has been mapped into a region near the APC locus to identify small deletions or rearrangements. Two of these cosmids, L5.71 and L5.79, hybridized with a 1200 kb NotI fragment in DNAs from most of the FAP patients screened.

The DNA of one FAP patient, 3214, showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb NotI fragment that was transmitted to her two unaffected offspring. These observations indicated that the mutant polyposis allele is on the same chromosome as the 940 kb NotI fragment. A simple interpretation is that APC patients 3214 and 4711 each carry a 260 kb deletion within the APC locus.

If a deletion were present, then other enzymes might also be expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, MluI fragments in patients 3214 and 4711 also showed an increase in size consistent with the deletion of an MluI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 3214 showed only a 940 kb Noti fragment, she had not inherited the 1200 kb fragment present in the unaffected father's DNA. This observation suggests that he must be heterozygous for, and have transmitted, either a deletion of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were both found to lie on a 550 kb NotI-NruI fragment and, therefore, on the same side of an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHWI41, which contains about 40% of chromosome 5, was digested with NotI and electrophoresed under pulsed-field gel (PFG) conditions; EcoRI fragments from the 1200 kb region of this gel were cloned into a phage vector. Probe Map30 was isolated from this library. In normal individuals probe Map30 hybridizes to the 1200 kb Noti fragment and to a 200 kb NruI fragment. This latter hybridization places Map30 distal, with respect to the locations of L5.71 and L5.79, to the NruI site of the 550 kb NotI-NruI fragment.

Because Map30 hybridized to the abnormal, 1300 kb NruI fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes, is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and MluI did not reveal abnormal bands, indicating that if a deletion were present, its boundaries must lie distal to the NruI and MluI sites of the fragments identified by L5.79. Consistent with this expectation, hybridization of Map30 to DNA from patient 3824 identified a 760 kb MluI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb MluI fragment identified by Map30 is distinct from the 830 kb MluI fragment identified previously by L5.79 was demonstrated by hybridization of Map30 and L5.79 to a NotI-MluI double digest of DNA from the hybrid cell (HHw1159) containing the nondeleted chromosome 5 homolog of patient 3214. As previously indicated, this hybrid is interpreted as missing one of the NotI sites that define the 1200 kb fragment. A 620 kb NotI-MluI fragment was seen with probe L5.79, and an 860 kb fragment was seen with Map30. Therefore, the 830 kb MluI fragment recognized by probe L5.79 must contain a NotI site in HHW1159 DNA; because the 860 kb MluI fragment remains intact, it does not carry this NotI site and must be distinct from the 830 kb MluI fragment.

EXAMPLE 5

This example demonstrates the isolation of human sequences which span the region deleted in the two unrelated FAP patients characterized in Example 4.

A strong prediction of the hypothesis that patients 3214 and 3824 carry deletions is that some sequences present on normal chromosome 5 homologs would be missing from the hypothesized deletion homologs. Therefore, to develop genomic probes that might confirm the deletions, as well as to identify genes from the region, YAC clones from a contig seeded by cosmid L5.79 were localized from a library containing seven haploid human genome equivalents (Albertsen et al., Proc. Natl. Acad. Sci. U.S.A., Vol. 87, pp.

4256–4260 (1990)) with respect to the hypothesized deletions. Three clones, YACs 57B8, 310D8, and 183H12, were found to overlap the deleted region.

Importantly, one end of YAC 57B8 (clone AT57) was found to lie within the patient 3214 deletion. Inverse polymerase chain reaction (PCR) defined the end sequences of the insert of YAC 57B8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHWI159) carrying the normal chromosome 5 homolog. This result supported the interpretation that the abnormal restriction fragments found in the DNA of patient 3214 result from a deletion.

Additional support for the hypothesis of deletion in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoRI fragments from YAC 183H12, Y10 and Y14, were localized within the patient 3214 deletion by their failure to hybridizie to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-MluI fragment seen with probe L5.79 in normal DNA, indicating its location as L5.79-proximal to the deleted MluI site and placing it between the MluI site and the L5.79-proximal NruI site. The MluI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 kb NotI-MluI fragment, placing it L5.79-distal to the MluI site, but proximal to the second NruI site. Hybridization to the same (860 kb) MluI fragment as Map30 confirmed the localization of probe Y11 L5.79-distal to the MluI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and deleted in patient 3214, with respect to L5.79 and Map30, is L5.79-Y10-Y11-Y14-Map30.

The 100 kb deletion of patient 3824 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the MluI digest, probe Y14 hybridized to the 860 kb and 760 kb fragments of patient 3824 DNA, but probe Y11 hybridized only to the 860 kb fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations, therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (Kinzler et al., supra). It was therefore of interest to map this gene with respect to the deletions in APC patients. Hybridization of MCC probes with an overlapping series of YAC clones extending in either direction from L5.71 showed that the 3' end of MCC must be oriented toward the region of the two APC deletions.

Therefore, two 3' cDNA clones from MCC were mapped with respect to the deletions: clone 1CI (bp 2378–4181) and clone 7 (bp 2890–3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the cDNA clones consists of a single 2.5 kb exon. These two clones were hybridized to DNAs from the YACs spanning the FAP region. Clone 7 fails to hybridize to YAC 310D8, although it does hybridize to YACs 183H12 and 57B8; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone contig is likely to be located more than 45 kb from the deletion of patient 3214 and, therefore, more than 100 kb from the deletion of patient 3824.

EXAMPLE 7

This example identifies three genes within the deleted region of chromosome 5 in the two unrelated FAP patients characterized in Example 4.

Genomic clones were used to screen cDNA libraries in three separate experiments. One screening was done with a phage clone derived from YAC 310D8 known to span the 260 kb deletion of patient 3214. A large-insert phage library was constructed from this YAC; screening with Y11 identified λ205, which mapped within both deletions. When clone X205 was used to probe a random-, plus oligo(dT)-, primed fetal brain cDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above. cDNA walks yielded a cDNA contig of 3.0–3.5 kb, and included two clones containing terminal poly(A) sequences. This size corresponds to the 3.5 kb band seen by Northern analysis. Sequencing of the first 3163 bp of the cDNA contig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the $NH_2$-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle, SRP19 (Lingelbach et al., supra). Hybridization experiments mapped YS-11 within both deletions. The sequence of this clone, however, was found to be complex. Although 454 bp of the 1032 bp sequence of YS-11 were identical to the GenBank entry for the SRP19 gene, another 578 bp appended 5' to the SRP19 sequence was found to consist of previously unreported sequence containing no extended open reading frames. This suggested that YS-11 was either a chimeric clone containing two independent inserts or a clone of an incompletely processed or aberrant message. If YS-11 were a conventional chimeric clone, the independent segments would not be expected to map to the same physical region. The segments resulting from anomalous processing of a continuous transcript, however, would map to a single chromosomal region.

Inverse PCR with primers specific to the two ends of YS-11, the SRP19 end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomic sequence was also seen after these 78 bp, suggesting the presence of a splice junction, and supporting the view that YS-11 represents an irregular message.

Starting with V5, successive 5' and 3' walks were performed; the resulting cDNA contig consisted of more than 100 clones, which defined a new transcript, DP2. Clones walking in the 5' direction crossed the 3824 deletion breakpoint farthest from L5.71; since its 3'end is closer to this cosmid than its 5' end, the transcriptional orientation of DP2 is opposite to that of MCC and DPL The third screening approach relied on hybridization with a 120 kb MluI fragment from YAC 57B8. This fragment hybridizes with probe Y11 and completely spans the 100 kb deletion in patient 3824. The fragment was purified on two preparative PFGs, labeled, and used to screen a fetal brain cDNA library. A number of cDNA clones previously identified in the development of the DP1 and DP2 contigs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 9.

The consensus cDNA sequence of DP2.5 suggests that the entire coding sequence of DP2.5 has been obtained and is 8532 bp long. The most 5' ATG codon occurs two codons from an in-frame stop and conforms to the Kozak initiation consensus (Kozak, Nucl. Acids. Res., Vol. 12, p. 857–872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to that identified as APC above.

An alternatively spliced exon at nucleotide 934 of the DP2.5 transcript is of potential interest. it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP25.

To obtain DNA sequence adjacent to the exons of the genes DP1, DP2.5, and SRP19, sequencing substrate was obtained by inverse PCR amplification of DNAs from two YACs, 310D8 and 183H12, that span the deletions. Ligation at low concentration cyclized the restriction enzyme-digested YAC DNAs. Oligonucleotides with sequencing tails, designed in inverse orientation at intervals along the cDNAs, primed PCR amplification from the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table III (SEQ ID NO:39–94). With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences. The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250–400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766–70 (1989) and Genomics, Vol. 5, pp. 874–879 (1989) as applied to DP1, SRP19 and DP2.5.

SSCP analysis identifies most single- or multiple-base changes in DNA fragments up to 400 bases in length. Sequence alterations are detected as shifts in electrophoretic mobility of single-stranded DNA on nondenaturing acrylamide gels; the two complementary strands of a DNA segment usually resolve as two SSCP conformers of distinct mobilities. However, if the sample is from an individual heterozygous for a base-pair variant within the amplified segment, often three or more bands are seen. In some cases, even the sample from a homozygous individual will show multiple bands. Base-pair-change variants are identified by differences in pattern among the DNAs of the sample set.

Exons of the candidate genes were amplified by PCR from the DNAs of 61 unrelated FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15 of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobilities. The normal conformers from the host individuals were sequenced also. Bands were cut from the dried acrylamide gels, and the DNA was eluted. PCR amplification of these DNAs provided template for sequencing.

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain a deletion of two adjacent nucleotides, at positions 730 and 731 in the cDNA sequence (FIG. 7A–7B (SEQ ID NO:1)). The normal sequence at this splice junction is CAGGGTCA (intronic sequence underlined), with the intron-exon boundary between the two repetitions of AG. The mutant allele in this patient has the sequence CAGGTCA. Although this change is at the 5' splice site, comparison with known consensus sequences of splice junctions would suggest that a functional splice junction is maintained. If this new splice junction were functional, the mutation would introduce a frameshift that creates a stop codon 15 nucleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient 3746 is heterozygous for a 2 bp deletion.

The unique conformer found in exon 8 of patient 3460 was found to carry a C-T transition, at position 904 in the cDNA sequence of DP2.5 (shown in FIG. 7), which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleotide (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an acrylamide-urea denaturing gel, along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position 1500, changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the patient's parents displayed the normal pattern of conformers for exon 7, as did DNA from the patients's wife and one of his offspring. The two other children, however, displayed the same new conformers as their affected father. Testing of the patient and his parents with highly polymorphic VNTR (variable number of tandem repeat) markers showed a 99.98% likelihood that they are his biological parents.

These observations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene: first, in exon 11, at position 1458, a substitution of T to C creating an RsaI restriction site but no amino acid change; and second, in exon 15, at positions 5037 and 5271, substitutions of A to G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated (SEQ ID NO:11–38).

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomic template. Two forms of exon 9 were found in DP2.5: one is the complete exon; and the other, labeled exon 9A, is the result of a splice into the interior of the exon that deletes bases 934 to 1236 in the mRNA and removes 101 amino acids from the predicted protein (see SEQ ID NO:182).

EXAMPLE 13

This example demonstrates the mapping of the FAP deletions with respect to the APC exons.

Somatic cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomic DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatic cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be assessed. All tissue types tested (brain, lung, aorta, spleen, heart, kidney, liver, stomach, placenta, and colonic mucosa) and cultured cell lines (lymphoblasts, HL60, and choriocarcinoma) expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistent with the size of the sequenced cDNA.

EXAMPLE 15

This example discusses structural features of the APC protein predicted from the sequence.

The cDNA consensus sequence of APC predicts that the longer, more abundant form of the message codes for a 2843 amino acid peptide with a mass of 311.8 kd. This predicted APC peptide was compared with the current data bases of protein and DNA sequences using both Intelligenetics and GCG software packages. No genes with a high degree of amino acid sequence similarity were found. Although many short (approximately 20 amino acid) regions of sequence similarity were uncovered, none was sufficiently strong to reveal which, if any, might represent functional homology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132 (1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem. Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table 4). The intervening sequences between the seven repeat regions contained 114, 116, 151, 205, 107, and 58 amino acids, respectively. Finally, residues 2200–24000 contain a 200 amino acid basic domain.

TABLE I

APC EXONS

| EXON NUCLEOTIDES[1] | EXON BOUNDARY SEQUENCE[2] |
|---|---|
| 822 to 930 | catgatgttatctgtatttacctatagtctaaattataccatctataatgtgcttaatttttat/GGTTCA ... <br> ... ACCAAG/gtaacagaagattacaaaccctggtcactaatgccatgactactttgctaag(SEQ ID NO: 24) |
| 931 to 1309 | ggatattaaagtcgtaattttgtttctaaactcatttggcccacag/GTGGAA ... <br> ... ATCCAA/gtatgttctctatagtgtacatcgtagtgcatg (SEQ ID NO: 26) |
| 1310 to 1405 | catcattgctcttcaaataacaaagcattatggtttatgttgatttatttttcag/TGCCAG ... <br> ... AACTAG/gtaagacaaaaatgttttttaatgacatagacaattactggta (SEQ ID NO: 28) |
| 1406 to 1545 | tagatgattgtcttttttcctcttgcccttttttaaattag/GGGGAC ... <br> ... AACAAG/gtatgtttttataacatgtatttcttaagatagctcaggtatga (SEQ ID NO: 30) |
| 1546 to 1623 | gcttggcttcaagttgtcttttttaatgatcctctattctgtatttaatttacag/GCTACG ... <br> ... CAGCAG/gtactatttagaatttcacctgttttctttttctcttttttctttgaggcagggtctcactctg (SEQ ID NO: 32) |
| 1624 to 1740 | gcaactagtatgattttatgtataaattaatctaaaattgattaatttgcag/GTTATT ... <br> ... AAAAAG/gtacctttgaaaacatttagtactataatatgaatttcatgt (SEQ ID NO: 34) |
| 1741 to 1955 | caactctaattagatgacccatattcagaaacttactag/GAATCA ... <br> ... CCACAG/gtatatatagagttttatattactttttaaagtacagaattcatactctcaaaaa (SEQ ID NO: 36) |
| 1956 to 8973 | tcttgattttatttcag/GCAAAT ... <br> ... GGTATTTATGCAAAAAAAAATGTTTTTGT (SEQ ID NO: 38) |
| (SEQ ID NO: 1) | |

[1]Relative to predicted translation initiation site
[2]Small case letters represent introns, large case letters represent exons
The entire 3' end of the cloned APC cDNA (nt 1956–8973) appeared to be encoded in this exon, as indicated by restriction endonuclease mapping and sequencing of cloned genomic DNA. The ORF ended at nt 8535. The extreme 3' end of the APC transcript has not yet been identified.

TABLE IIA

Germline mutations of the APC gene in FAP and GS Patients

| PATIENT DISEASE | CO-DON | NUCLEOTIDE CHANGE | AMINO ACID CHANGE | AGE | EXTRA-COLONIC |
|---|---|---|---|---|---|
| 93 Osteoma | 279 | TCA→TGA | Ser→Stop | 39 | Mandibular |
| 24 | 301 | CGA→TGA | Arg→Stop | 46 | Mone |
| 34 Tumor | 301 | CGA→TGA | Arg→Stop | 27 | Desmold |
| 21 Osteoma | 413 | CGC→TGC | Arg→Cys | 24 | Mandibular |
| 60 Osteoma | 712 | TCA→TGA | Ser→Stop | 37 | Mandibular |
| 3746 | 243 | CAGAG→CAG | splice-junction | | |
| 3460 | 301 | CGA→TGA | Arg→stop | | |
| 3827 | 456 | CTTTCA→CTTCA | frameshift | | |
| 3712 | 500 | T→G | Tyr→Stop | | |

\* The mutated nucleotides are underlined.

TABLE IIB

Somatic Mutations in Sporadic CRC Patients

| PATIENT | CODON[1] | NUCLEOTIDE CHANGE | AMINO ACID CHANGE |
|---|---|---|---|
| r35 | MCC 12 | GAG/gtaaga→ GAG/gtaaga | (Splice Donor) |
| T16 | MCC 145 | ctcag/GGA→ itcag/GGA | (Splice Acceptor) |
| T47 | MCC 267 | CGG→CTG | Arg→Leu |
| T81 | MCC 490 | TCG→TTG | Ser→Leu |
| T35 | MCC 506 | CGG→CAG | Arg→Gln |
| T91 | MCC 698 | GCT→GTT | Ala→Val |
| T34 | APC 288 | CCAGT→CCCAGCCAGT | (Insertion) |
| T27 | APC 331 | CGA→TGA | Arg→Stop |
| T135 | APC 437 | CAA/gtaa→CAA/gcaa | (Splice Donor) |
| 7201 | APC 1338 | CAG→TAG | Gln→Stop |

For splice site mutations, the codon nearest to the mutation is listed
The underlined nucleotides were mutant; small case letter: represent introns, large case letter: represent exons

TABLE III

Sequences of Primers Used for SSCP Analyses

| Exon | Primer 1 | Primer 2 |
|---|---|---|
| DP1 | | |
| | UP-TCCCCGCCTGCCGGTCTC | RP-GCAGCGGCGGCTCCCGTG |
| | UP-GTGAACGGCTCTCATGCTGC | RP-ACGTGCGGGGAGGAATGGA |
| | UP-ATGATATCTTACCAAATGATATAC | RP-TTATTCCTACTTCTTCTATACAG |

TABLE III-continued

Sequences of Primers Used for SSCP Analyses

| Exon | Primer 1 | Primer 2 |
|---|---|---|
| | UP-TACCCATGCTGGCTCTTTTTC | RP-TGGGGCCATCTTGTTCCTGA |
| | UP-ACATTAGGCACAAAGCTTGCAA | RP-ATCAAGCTCCAGTAAGAAGGTA |
| | SRP19 | |
| | UP-TGCGGCTCCTGGGTTGTTG | RP-GCCCCTTCCTTTCTGAGGAC |
| | UP-TTTTCTCCTGCCTCTTACTGC | RP-ATGACACCCCCCATTCCCTC |
| | UP-CCACTTAAAGCACATATATTTAGT | RP-GTATGGAAAATAGTGAAGAACC |
| | UP-TTCTTAAGTCCTGTTCTTTTG | RP-TTTAGAACCTTTTTTGTGTTGTG |
| | UP-CTCAGATTATACACTAAGCCCTAAC | RP-CATGTCTCTTACAGTAGTACCA |
| | DP2.5 | |
| | UP-AGGTCCAAGGGTAGCCAAGG* | RP-TAAAAATGGATAAACTACAATTAAAAG |
| | UP-AAATACAGAATCATGTCTTGAAGT | RP-ACACCTAAAGATGACAATTTGAG |
| | UP-TAACTTAGATAGCAGTAATTTCCC* | RP-ACAATAAACTGGAGTACACAAGG |
| | UP-ATAGGTCATTGCCTCTTGCTGAT* | RP-TGAATTTTAATGGATTACCTAGGT |
| | UP-CTTTTTTGCTTTTACTGATTAACG | RP-TGTAATTCATTTTATTCCTAATACCTC |
| | UP-GTAGCCATAGTATGATTATTTCT | RP-CTACCTATTTTTATACCCACAAAC |
| | UP-AAGAAAGCCTACACCATTTTTGC | RP-GATCATTCTTAGAACCATCTTGC |
| | UP-ACCTATAGTCTAAATTATACCATC | RP-GTCATGGCATTACTGACCAG |
| | UP-AGTCGTAATTTTGTTTCTAAACTC | RP-TGAAGGACTCCGATTTCACCC* |
| | UP-TCATTCACTCACAGCCTGATGAC* | RP-GCTTTGAAACATGCACTACGAT |
| | UP-AAACATCATTGCTCTTCAAATAAC | RP-TACCATGATTTAAAAATCCACCAG |
| | UP-GATGATTGTCTTTCCTCTTGC | RP-CTGAGCTATCTTAAGAAATACATG |
| | UP-TTTTAAATGATCCTCTATTCTGTAT | RP-ACAGAGTCAGACCCTCCCTCAAAG |
| | UP-TTTCTATTCTTACTGCTAGCATT | RP-ATACACAGGTAAGAAATTAGGA |
| | UP-TAGATGACCCATATTCTCTTTC | RP-CAATTAGGTCTTTTTGAGAGTA |
| 3-A | UP-GTTACTGCATACACATTGTGAC | RP-GCTTGTTTCGTAACATGAAG* |
| -B | UP-AGTACAAGGATGCCAATATTATG* | RP-ACTTCTATCTTTTTCAGAACGAG* |
| -C | UP-ATTTGAATACTACAGTGTTACCC* | RP-CTTGTATTCTAATTTGGCATAAGG* |
| -D | UP-CTGCCCATACACATTCAAACAC* | RP-TGTTTGCGTCTTGCCCATCTT* |
| -E | UP-AGTCTTAAATATTCAGATGAGCAG* | RP-GTTTCTCTTCATTATATTTTATGCTA* |
| -F | UP-AAGCCTACCAATTATAGTGAACG* | RP-AGCTGATGACAAAGATGATAATC* |
| -G | UP-AAGAAACAATACAGACTTATTGTG* | RP-ATGAGTGGGGTCTCCTGAAC* |
| -H | UP-ATCTCCCTCCAAAAGTGGTGC* | RP-TCCATCTGGAGTACTTTCTGTG* |
| -I | UP-AGTAAATGCTGCAGTTCAGAGG* | RP-CCGTGGCATATCATCCCCC* |
| -J | UP-CCCAGACTGCTTCAAAATTACC* | RP-GAGCCTCATCTGTACTTCTGC* |
| -K | UP-CCCTCCAAATGAGTTAGCTGC* | RP-TTGTGGTATAGGTTTTACTGGTG* |
| -L | UP-ACCCAACAAAAATCAGTTAGATG* | RP-GTGGCTGGTAACTTTAGCCTC* |
| -N | UP-ATGATGTTGACCTTTCCAGGG* | RP-ATTGTGTAACTTTCATCAGTTGC* |
| -M | UP-AAAGACATACCAGACAGAGGG* | RP-CTTTTTTGGCATTGCGGAGCT* |
| -O | UP-AAGATGACCTGTTGCAGGAATG* | RP-GAATCAGACCAAGCTTGTCTAGAT* |
| -P | UP-CAATAGTAAGTAGTTTACATCAAG* | RP-AAACAGGACTTGTACTGTAGGA* |
| -Q | UP-CAGCCCCTTCAAGCAAACATC* | RP-GAGGACTTATTCCATTTCTACC* |
| -R | UP-CAGTCTCCTGGCCGAAACTC* | RP-GTTGACTGGCGTACTAATACAG* |
| -S | UP-TGGTAATGGAGCCAATAAAAAGG* | RP-TGGGACTTTTCGCCATCCAC* |
| -T | UP-TGTCTCTATCCACACATTCGTC* | RP-ATGTTTTTCATCCTCACTTTTTGC* |
| -U | UP-GGAGAAGAACTGGAAGTTCATC* | RP-TTGAATCTTTAATGTTTGGATTTGC* |
| -V | UP-TCTCCCACAGGTAATACTCCC | RP-GCTACAACTGAATGGGGTACG |
| -W | UP-CAGGACAAAATAATCCTGTCCC | RP-ATTTTCTTACTTTCATTCTTCCTC |

All primers are read in the 5' to 3' direction. the first primer in each pair lies 5' of the exon it amplifies: the second primer lies 3' or the exon it amplifies. Primers that lie within the exon are identified by an asterisk. UP represents the - 21M13 universal primer sequence: RP represents the M13 reverse primer sequence.

TABLE IV

Seven Different Versions of the 20-Amino Acid Repeat

| Consensus: | F | • | V | E | • | T | P | • | C | F | S | R | • | S | S | L | S | S | L | S |
|---|---|---|---|---|---|---|---|---|---|---|---|---|---|---|---|---|---|---|---|---|
| 1262: | Y | C | V | E | D | T | P | I | C | F | S | R | C | S | S | L | S | S | L | S |
| 1376: | H | Y | V | Q | E | T | P | L | M | F | S | R | C | T | S | V | S | S | L | D |
| 1492: | F | A | T | E | S | T | P | D | G | F | S | C | S | S | L | S | A | L | S |
| 1643: | Y | C | V | E | G | T | P | I | N | F | S | T | A | T | S | L | S | D | L | T |
| 1848: | T | P | I | E | G | T | P | Y | C | F | S | R | N | O | S | L | S | S | L | D |
| 1953: | F | A | I | E | N | T | P | V | C | P | S | H | N | S | S | L | S | S | L | S |
| 2013: | F | H | V | E | D | T | P | V | C | F | S | R | N | S | S | L | S | S | L | S |

Numbers dencie the first amino acid of each repeat. The consensus sequence at the top reflects a majority amino acid at a given position.

We claim:

1. A preparation of the human APC (adenomatous polyposis colorectal cancer) protein substantially free of other human proteins, the amino acid sequence of said protein corresponding to that shown in FIG. 3 or 7 (SEQ ID NOS:7 or 2).

2. A preparation of human APC protein substantially free of other human proteins, wherein said protein is encoded by overlapping cDNA clones FB9A, FB97A, FB70B, FB64A, and FB54D, which were deposited at the American Type Culture Collection.

3. A preparation of human APC protein substantially free of other human proteins, said protein encoded by YAC 37HG4, deposited at the National Collection of Industrial and Marine Bacteria as accession no. NCIMB 40353.

4. A preparation of human APC protein substantially free of other human proteins, said protein encoded at human chromosome 5q21.

5. The preparation of claim 4 wherein 12% of the N-terminal 25% of the protein consists of leucine residues and 17% of the C-terminal 75% of the protein consists of serine residues.

* * * * *

SEQUENCE LISTING ( 1 ) GENERAL INFORMATION:

( i i i ) NUMBER OF SEQUENCES: 102

( 2 ) INFORMATION FOR SEQ ID NO:1:

( i ) SEQUENCE CHARACTERISTICS:
        ( A ) LENGTH: 8532 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP2.5(APC)

( v i i i ) SEQUENCE DESCRIPTION: SEQ ID NO:1:

```
ATGGCTGCAG  CTTCATATGA  TCAGTTGTTA  AAGCAAGTTG  AGGCACTGAA  GATGGAGAAC     60
TCAAATCTTC  GACAAGAGCT  AGAAGATAAT  TCCAATCATC  TTACAAAACT  GGAAACTGAG    120
GCATCTAATA  TGAAGGAAGT  ACTTAAACAA  CTACAAGGAA  GTATTGAAGA  TGAAGCTATG    180
GCTTCTTCTG  GACAGATTGA  TTTATTAGAG  CGTCTTAAAG  AGCTTAACTT  AGATAGCAGT    240
AATTTCCCTG  GAGTAAAACT  GCGGTCAAAA  ATGTCCCTCC  GTTCTTATGG  AAGCCGGGAA    300
GGATCTGTAT  CAAGCCGTTC  TGGAGAGTGC  AGTCCTGTTC  CTATGGGTTC  ATTTCCAAGA    360
AGAGGGTTTG  TAAATGGAAG  CAGAGAAAGT  ACTGGATATT  TAGAAGAACT  TGAGAAAGAG    420
AGGTCATTGC  TTCTTGCTGA  TCTTGACAAA  GAAGAAAAGG  AAAAAGACTG  GTATTACGCT    480
CAACTTCAGA  ATCTCACTAA  AAGAATAGAT  AGTCTTCCTT  TAACTGAAAA  TTTTTCCTTA    540
CAAACAGATA  TGACCAGAAG  GCAATTGGAA  TATGAAGCAA  GGCAAATCAG  AGTTGCGATG    600
GAAGAACAAC  TAGGTACCTG  CCAGGATATG  GAAAAACGAG  CACAGCGAAG  AATAGCCAGA    660
ATTCAGCAAA  TCGAAAAGGA  CATACTTCGT  ATACGACAGC  TTTTACAGTC  CCAAGCAACA    720
GAAGCAGAGA  GGTCATCTCA  GAACAAGCAT  GAAACCGGCT  CACATGATGC  TGAGCGGCAG    780
AATGAAGGTC  AAGGAGTGGG  AGAAATCAAC  ATGGCAACTT  CTGGTAATGG  TCAGGGTTCA    840
ACTACACGAA  TGGACCATGA  AACAGCCAGT  GTTTTGAGTT  CTAGTAGCAC  ACACTCTGCA    900
CCTCGAAGGC  TGACAAGTCA  TCTGGGAACC  AAGGTGGAAA  TGGTGTATTC  ATTGTTGTCA    960
ATGCTTGGTA  CTCATGATAA  GGATGATATG  TCGCGAACTT  TGCTAGCTAT  GTCTAGCTCC   1020
CAAGACAGCT  GTATATCCAT  GCGACAGTCT  GGATGTCTTC  CTCTCCTCAT  CCAGCTTTTA   1080
CATGGCAATG  ACAAAGACTC  TGTATTGTTG  GGAAATTCCC  GGGGCAGTAA  AGAGGCTCGG   1140
GCCAGGGCCA  GTGCAGCACT  CCACAACATC  ATTCACTCAC  AGCCTGATGA  CAAGAGAGGC   1200
AGGCGTGAAA  TCCGAGTCCT  TCATCTTTTG  GAACAGATAC  GCGCTTACTG  TGAAACCTGT   1260
TGGGAGTGGC  AGGAAGCTCA  TGAACCAGGC  ATGGACCAGG  ACAAAAATCC  AATGCCAGCT   1320
CCTGTTGAAC  ATCAGATCTG  TCCTGCTGTG  TGTGTTCTAA  TGAAACTTTC  ATTTGATGAA   1380
GAGCATAGAC  ATGCAATGAA  TGAACTAGGG  GGACTACAGG  CCATTGCAGA  ATTATTGCAA   1440
GTGGACTGTG  AAATGTACGG  GCTTACTAAT  GACCACTACA  GTATTACACT  AAGACGATAT   1500
GCTGGAATGG  CTTTGACAAA  CTTGACTTTT  GGAGATGTAG  CCAACAAGGC  TACGCTATGC   1560
TCTATGAAAG  GCTGCATGAG  AGCACTTGTG  GCCCAACTAA  AATCTGAAAG  TGAAGACTTA   1620
```

| | | | | | |
|---|---|---|---|---|---|
| CAGCAGGTTA | TTGCAAGTGT | TTTGAGGAAT | TTGTCTTGGC | GAGCAGATGT | AAATAGTAAA | 1680 |
| AAGACGTTGC | GAGAAGTTGG | AAGTGTGAAA | GCATTGATGG | AATGTGCTTT | AGAAGTTAAA | 1740 |
| AAGGAATCAA | CCCTCAAAAG | CGTATTGAGT | GCCTTATGGA | ATTTGTCAGC | ACATTGCACT | 1800 |
| GAGAATAAAG | CTGATATATG | TGCTGTAGAT | GGTGCACTTG | CATTTTTGGT | TGGCACTCTT | 1860 |
| ACTTACCGGA | GCCAGACAAA | CACTTTAGCC | ATTATTGAAA | GTGGAGGTGG | GATATTACGG | 1920 |
| AATGTGTCCA | GCTTGATAGC | TACAAATGAG | GACCACAGGC | AAATCCTAAG | AGAGAACAAC | 1980 |
| TGTCTACAAA | CTTTATTACA | ACACTTAAAA | TCTCATAGTT | TGACAATAGT | CAGTAATGCA | 2040 |
| TGTGGAACTT | TGTGGAATCT | CTCAGCAAGA | AATCCTAAAG | ACCAGGAAGC | ATTATGGGAC | 2100 |
| ATGGGGCAG | TTAGCATGCT | CAAGAACCTC | ATTCATTCAA | AGCACAAAAT | GATTGCTATG | 2160 |
| GGAAGTGCTG | CAGCTTTAAG | GAATCTCATG | GCAAATAGGC | CTGCGAAGTA | CAAGGATGCC | 2220 |
| AATATTATGT | CTCCTGGCTC | AAGCTTGCCA | TCTCTTCATG | TTAGGAAACA | AAAAGCCCTA | 2280 |
| GAAGCAGAAT | TAGATGCTCA | GCACTTATCA | GAAACTTTTG | ACAATATAGA | CAATTTAAGT | 2340 |
| CCCAAGGCAT | CTCATCGTAG | TAAGCAGAGA | CACAAGCAAA | GTCTCTATGG | TGATTATGTT | 2400 |
| TTTGACACCA | ATCGACATGA | TGATAATAGG | TCAGACAATT | TTAATACTGG | CAACATGACT | 2460 |
| GTCCTTTCAC | CATATTTGAA | TACTACAGTG | TTACCCAGCT | CCTCTTCATC | AAGAGGAAGC | 2520 |
| TTAGATAGTT | CTCGTTCTGA | AAAAGATAGA | AGTTGGAGA | GAGAACGCGG | AATTGGTCTA | 2580 |
| GGCAACTACC | ATCCAGCAAC | AGAAAATCCA | GGAACTTCTT | CAAAGCGAGG | TTTGCAGATC | 2640 |
| TCCACCACTG | CAGCCCAGAT | TGCCAAAGTC | ATGGAAGAAG | TGTCAGCCAT | TCATACCTCT | 2700 |
| CAGGAAGACA | GAAGTTCTGG | GTCTACCACT | GAATTACATT | GTGTGACAGA | TGAGAGAAAT | 2760 |
| GCACTTAGAA | GAAGCTCTGC | TGCCCATACA | CATTCAAACA | CTTACAATTT | CACTAAGTCG | 2820 |
| GAAAATTCAA | ATAGGACATG | TTCTATGCCT | TATGCCAAAT | TAGAATACAA | GAGATCTTCA | 2880 |
| AATGATAGTT | TAAATAGTGT | CAGTAGTAGT | GATGGTTATG | GTAAAAGAGG | TCAAATGAAA | 2940 |
| CCCTCGATTG | AATCCTATTC | TGAAGATGAT | GAAAGTAAGT | TTTGCAGTTA | TGGTCAATAC | 3000 |
| CCAGCCGACC | TAGCCCATAA | AATACATAGT | GCAAATCATA | TGGATGATAA | TGATGGAGAA | 3060 |
| CTAGATACAC | CAATAAATTA | TAGTCTTAAA | TATTCAGATG | AGCAGTTGAA | CTCTGGAAGG | 3120 |
| CAAAGTCCTT | CACAGAATGA | AAGATGGGCA | AGACCCAAAC | ACATAATAGA | AGATGAAATA | 3180 |
| AAACAAAGTG | AGCAAAGACA | ATCAAGGAAT | CAAAGTACAA | CTTATCCTGT | TTATACTGAG | 3240 |
| AGCACTGATG | ATAAACACCT | CAAGTTCCAA | CCACATTTTG | GACAGCAGGA | ATGTGTTTCT | 3300 |
| CCATACAGGT | CACGGGGAGC | CAATGGTTCA | GAAACAAATC | GAGTGGGTTC | TAATCATGGA | 3360 |
| ATTAATCAAA | ATGTAAGCCA | GTCTTTGTGT | CAAGAAGATG | ACTATGAAGA | TGATAAGCCT | 3420 |
| ACCAATTATA | GTGAACGTTA | CTCTGAAGAA | GAACAGCATG | AAGAAGAAGA | GAGACCAACA | 3480 |
| AATTATAGCA | TAAAATATAA | TGAAGAGAAA | CGTCATGTGG | ATCAGCCTAT | TGATTATAGT | 3540 |
| TTAAAATATG | CCACAGATAT | TCCTTCATCA | CAGAAACAGT | CATTTTCATT | CTCAAAGAGT | 3600 |
| TCATCTGGAC | AAAGCAGTAA | AACCGAACAT | ATGTCTTCAA | GCAGTGAGAA | TACGTCCACA | 3660 |
| CCTTCATCTA | ATGCCAAGAG | GCAGAATCAG | CTCCATCCAA | GTTCTGCACA | GAGTAGAAGT | 3720 |
| GGTCAGCCTC | AAAAGGCTGC | CACTTGCAAA | GTTTCTTCTA | TTAACCAAGA | AACAATACAG | 3780 |
| ACTTATTGTG | TAGAAGATAC | TCCAATATGT | TTTTCAAGAT | GTAGTTCATT | ATCATCTTTG | 3840 |
| TCATCAGCTG | AAGATGAAAT | AGGATGTAAT | CAGACGACAC | AGGAAGCAGA | TTCTGCTAAT | 3900 |
| ACCCTGCAAA | TAGCAGAAAT | AAAAGAAAAG | ATTGGAACTA | GGTCAGCTGA | AGATCCTGTG | 3960 |
| AGCGAAGTTC | CAGCAGTGTC | ACAGCACCCT | AGAACCAAAT | CCAGCAGACT | GCAGGGTTCT | 4020 |

| | | | | | |
|---|---|---|---|---|---|
| AGTTTATCTT | CAGAATCAGC | CAGGCACAAA | GCTGTTGAAT | TTTCTTCAGG | AGCGAAATCT | 4080 |
| CCCTCCAAAA | GTGGTGCTCA | GACACCCAAA | AGTCCACCTG | AACACTATGT | TCAGGAGACC | 4140 |
| CCACTCATGT | TTAGCAGATG | TACTTCTGTC | AGTTCACTTG | ATAGTTTGA | GAGTCGTTCG | 4200 |
| ATTGCCAGCT | CCGTTCAGAG | TGAACCATGC | AGTGGAATGG | TAAGTGGCAT | TATAAGCCCC | 4260 |
| AGTGATCTTC | CAGATAGCCC | TGGACAAACC | ATGCCACCAA | GCAGAAGTAA | AACACCTCCA | 4320 |
| CCACCTCCTC | AAACAGCTCA | AACCAAGCGA | GAAGTACCTA | AAAATAAAGC | ACCTACTGCT | 4380 |
| GAAAAGAGAG | AGAGTGGACC | TAAGCAAGCT | GCAGTAAATG | CTGCAGTTCA | GAGGGTCCAG | 4440 |
| GTTCTTCCAG | ATGCTGATAC | TTTATTACAT | TTTGCCACGG | AAAGTACTCC | AGATGGATTT | 4500 |
| TCTTGTTCAT | CCAGCCTGAG | TGCTCTGAGC | CTCGATGAGC | CATTTATACA | GAAAGATGTG | 4560 |
| GAATTAAGAA | TAATGCCTCC | AGTTCAGGAA | AATGACAATG | GGAATGAAAC | AGAATCAGAG | 4620 |
| CAGCCTAAAG | AATCAAATGA | AAACCAAGAG | AAAGAGGCAG | AAAAAACTAT | TGATTCTGAA | 4680 |
| AAGGACCTAT | TAGATGATTC | AGATGATGAT | GATATTGAAA | TACTAGAAGA | ATGTATTATT | 4740 |
| TCTGCCATGC | CAACAAAGTC | ATCACGTAAA | GCAAAAAAGC | CAGCCCAGAC | TGCTTCAAAA | 4800 |
| TTACCTCCAC | CTGTGGCAAG | GAAACCAAGT | CAGCTGCCTG | TGTACAAACT | TCTACCATCA | 4860 |
| CAAAACAGGT | TGCAACCCCA | AAAGCATGTT | AGTTTTACAC | CGGGGGATGA | TATGCCACGG | 4920 |
| GTGTATTGTG | TTGAAGGGAC | ACCTATAAAC | TTTTCCACAG | CTACATCTCT | AAGTGATCTA | 4980 |
| ACAATCGAAT | CCCCTCCAAA | TGAGTTAGCT | GCTGGAGAAG | GAGTTAGAGG | AGGAGCACAG | 5040 |
| TCAGGTGAAT | TTGAAAAACG | AGATACCATT | CCTACAGAAG | GCAGAAGTAC | AGATGAGGCT | 5100 |
| CAAGGAGGAA | AAACCTCATC | TGTAACCATA | CCTGAATTGG | ATGACAATAA | AGCAGAGGAA | 5160 |
| GGTGATATTC | TTGCAGAATG | CATTAATTCT | GCTATGCCCA | AAGGGAAAAG | TCACAAGCCT | 5220 |
| TTCCGTGTGA | AAAAGATAAT | GGACCAGGTC | CAGCAAGCAT | CTGCGTCGTC | TTCTGCACCC | 5280 |
| AACAAAAATC | AGTTAGATGG | TAAGAAAAAG | AAACCAACTT | CACCAGTAAA | ACCTATACCA | 5340 |
| CAAAATACTG | AATATAGGAC | ACGTGTAAGA | AAAAATGCAG | ACTCAAAAAA | TAATTTAAAT | 5400 |
| GCTGAGAGAG | TTTTCTCAGA | CAACAAAGAT | TCAAAGAAAC | AGAATTTGAA | AAATAATTCC | 5460 |
| AAGGACTTCA | ATGATAAGCT | CCCAAATAAT | GAAGATAGAG | TCAGAGGAAG | TTTTGCTTTT | 5520 |
| GATTCACCTC | ATCATTACAC | GCCTATTGAA | GGAACTCCTT | ACTGTTTTTC | ACGAAATGAT | 5580 |
| TCTTTGAGTT | CTCTAGATTT | TGATGATGAT | GATGTTGACC | TTTCCAGGGA | AAAGGCTGAA | 5640 |
| TTAAGAAAGG | CAAAAGAAAA | TAAGGAATCA | GAGGCTAAAG | TTACCAGCCA | CACAGAACTA | 5700 |
| ACCTCCAACC | AACAATCAGC | TAATAAGACA | CAAGCTATTG | CAAAGCAGCC | AATAAATCGA | 5760 |
| GGTCAGCCTA | AACCCATACT | TCAGAAACAA | TCCACTTTTC | CCCAGTCATC | CAAAGACATA | 5820 |
| CCAGACAGAG | GGGCAGCAAC | TGATGAAAAG | TTACAGAATT | TTGCTATTGA | AAATACTCCA | 5880 |
| GTTTGCTTTT | CTCATAATTC | CTCTCTGAGT | TCTCTCAGTG | ACATTGACCA | AGAAAACAAC | 5940 |
| AATAAAGAAA | ATGAACCTAT | CAAAGAGACT | GAGCCCCCTG | ACTCACAGGG | AGAACCAAGT | 6000 |
| AAACCTCAAG | CATCAGGCTA | TGCTCCTAAA | TCATTTCATG | TTGAAGATAC | CCCAGTTTGT | 6060 |
| TTCTCAAGAA | ACAGTTCTCT | CAGTTCTCTT | AGTATTGACT | CTGAAGATGA | CCTGTTGCAG | 6120 |
| GAATGTATAA | GCTCCGCAAT | GCCAAAAAAG | AAAAGCCTT | CAAGACTCAA | GGGTGATAAT | 6180 |
| GAAAACATA | GTCCCAGAAA | TATGGGTGGC | ATATTAGGTG | AAGATCTGAC | ACTTGATTTG | 6240 |
| AAAGATATAC | AGAGACCAGA | TTCAGAACAT | GGTCTATCCC | CTGATTCAGA | AAATTTTGAT | 6300 |
| TGGAAAGCTA | TTCAGGAAGG | TGCAAATTCC | ATAGTAAGTA | GTTTACATCA | AGCTGCTGCT | 6360 |
| GCTGCATGTT | TATCTAGACA | AGCTTCGTCT | GATTCAGATT | CCATCCTTTC | CCTGAAATCA | 6420 |

-continued

```
GGAATCTCTC TGGGATCACC ATTTCATCTT ACACCTGATC AAGAAGAAAA ACCCTTTACA    6480
AGTAATAAAG GCCCACGAAT TCTAAAACCA GGGGAGAAAA GTACATTGGA AACTAAAAAG    6540
ATAGAATCTG AAAGTAAAGG AATCAAAGGA GGAAAAAAAG TTTATAAAAG TTTGATTACT    6600
GGAAAAGTTC GATCTAATTC AGAAATTTCA GGCCAAATGA ACAGCCCCT  TCAAGCAAAC    6660
ATGCCTTCAA TCTCTCGAGG CAGGACAATG ATTCATATTC CAGGAGTTCG AAATAGCTCC    6720
TCAAGTACAA GTCCTGTTTC TAAAAAGGC  CCACCCCTTA AGACTCCAGC CTCCAAAAGC    6780
CCTAGTGAAG GTCAAACAGC CACCACTTCT CCTAGAGGAG CCAAGCCATC TGTGAAATCA    6840
GAATTAAGCC CTGTTGCCAG GCAGACATCC CAAATAGGTG GGTCAAGTAA AGCACCTTCT    6900
AGATCAGGAT CTAGAGATTC GACCCCTTCA AGACCTGCCC AGCAACCATT AAGTAGACCT    6960
ATACAGTCTC CTGGCCGAAA CTCAATTTCC CCTGGTAGAA ATGGAATAAG TCCTCCTAAC    7020
AAATTATCTC AACTTCCAAG GACATCATCC CCTAGTACTG CTTCAACTAA GTCCTCAGGT    7080
TCTGGAAAAA TGTCATATAC ATCTCCAGGT AGACAGATGA GCCAACAGAA CCTTACCAAA    7140
CAAACAGGTT TATCCAAGAA TGCCAGTAGT ATTCCAAGAA GTGAGTCTGC CTCCAAAGGA    7200
CTAAATCAGA TGAATAATGG TAATGGAGCC AATAAAAAGG TAGAACTTTC TAGAATGTCT    7260
TCAACTAAAT CAAGTGGAAG TGAATCTGAT AGATCAGAAA GACCTGTATT AGTACGCCAG    7320
TCAACTTTCA TCAAAGAAGC TCCAAGCCCA ACCTTAAGAA GAAAATTGGA GGAATCTGCT    7380
TCATTTGAAT CTCTTTCTCC ATCATCTAGA CCAGCTTCTC CCACTAGGTC CCAGGCACAA    7440
ACTCCAGTTT TAAGTCCTTC CCTTCCTGAT ATGTCTCTAT CCACACATTC GTCTGTTCAG    7500
GCTGGTGGAT GGCGAAAACT CCCACCTAAT CTCAGTCCCA CTATAGAGTA TAATGATGGA    7560
AGACCAGCAA AGCGCCATGA TATTGCACGG TCTCATTCTG AAAGTCCTTC TAGACTTCCA    7620
ATCAATAGGT CAGGAACCTG GAAACGTGAG CACAGCAAAC ATTCATCATC CCTTCCTCGA    7680
GTAAGCACTT GGAGAAGAAC TGGAAGTTCA TCTTCAATTC TTTCTGCTTC ATCAGAATCC    7740
AGTGAAAAAG CAAAAAGTGA GGATGAAAAA CATGTGAACT CTATTTCAGG AACCAAACAA    7800
AGTAAAGAAA ACCAAGTATC CGCAAAAGGA ACATGGAGAA AAATAAAAGA AAATGAATTT    7860
TCTCCCACAA ATAGTACTTC TCAGACCGTT TCCTCAGGTG CTACAAATGG TGCTGAATCA    7920
AAGACTCTAA TTTATCAAAT GGCACCTGCT GTTTCTAAAA CAGAGGATGT TGGGTGAGA    7980
ATTGAGGACT GTCCCATTAA CAATCCTAGA TCTGGAAGAT CTCCCACAGG TAATACTCCC    8040
CCGGTGATTG ACAGTGTTTC AGAAAAGGCA AATCCAAACA TTAAAGATTC AAAAGATAAT    8100
CAGGCAAAAC AAAATGTGGG TAATGGCAGT GTTCCCATGC GTACCGTGGG TTTGGAAAAT    8160
CGCCTGAACT CCTTTATTCA GGTGGATGCC CCTGACCAAA AAGGAACTGA GATAAAACCA    8220
GGACAAAATA ATCCTGTCCC TGTATCAGAG ACTAATGAAA GTTCTATAGT GGAACGTACC    8280
CCATTCAGTT CTAGCAGCTC AAGCAAACAC AGTTCACCTA GTGGGACTGT TGCTGCCAGA    8340
GTGACTCCTT TTAATTACAA CCCAAGCCCT AGGAAAAGCA GCGCAGATAG CACTTCAGCT    8400
CGGCCATCTC AGATCCCAAC TCCAGTGAAT AACAACACAA AGAAGCGAGA TTCCAAAACT    8460
GACAGCACAG AATCCAGTGG AACCCAAAGT CCTAAGCGCC ATTCTGGGTC TTACCTTGTG    8520
ACATCTGTTT AA                                                        8532
```

( 2 ) INFORMATION FOR SEQ ID NO:2:

( i ) SEQUENCE CHARACTERISTICS:
( A ) LENGTH: 2843 amino acids
( B ) TYPE: amino acid
( D ) TOPOLOGY: linear (ii) MOLECULE TYPE: protein (xi) SEQUENCE DESCRIPTION: SEQ ID NO:2:

| Met | Ala | Ala | Ala | Ser | Tyr | Asp | Gln | Leu | Leu | Lys | Gln | Val | Glu | Ala | Leu |
|---|---|---|---|---|---|---|---|---|---|---|---|---|---|---|---|
| 1 | | | | 5 | | | | | 10 | | | | | 15 | |
| Lys | Met | Glu | Asn | Ser | Asn | Leu | Arg | Gln | Glu | Leu | Glu | Asp | Asn | Ser | Asn |
| | | | 20 | | | | | 25 | | | | | 30 | | |
| His | Leu | Thr | Lys | Leu | Glu | Thr | Glu | Ala | Ser | Asn | Met | Lys | Glu | Val | Leu |
| | | 35 | | | | | 40 | | | | | 45 | | | |
| Lys | Gln | Leu | Gln | Gly | Ser | Ile | Glu | Asp | Glu | Ala | Met | Ala | Ser | Ser | Gly |
| | 50 | | | | | 55 | | | | | 60 | | | | |
| Gln | Ile | Asp | Leu | Leu | Glu | Arg | Leu | Lys | Glu | Leu | Asn | Leu | Asp | Ser | Ser |
| 65 | | | | | 70 | | | | | 75 | | | | | 80 |
| Asn | Phe | Pro | Gly | Val | Lys | Leu | Arg | Ser | Lys | Met | Ser | Leu | Arg | Ser | Tyr |
| | | | | 85 | | | | | 90 | | | | | 95 | |
| Gly | Ser | Arg | Glu | Gly | Ser | Val | Ser | Ser | Arg | Ser | Gly | Glu | Cys | Ser | Pro |
| | | | 100 | | | | | 105 | | | | | 110 | | |
| Val | Pro | Met | Gly | Ser | Phe | Pro | Arg | Arg | Gly | Phe | Val | Asn | Gly | Ser | Arg |
| | | 115 | | | | | 120 | | | | | 125 | | | |
| Glu | Ser | Thr | Gly | Tyr | Leu | Glu | Leu | Glu | Lys | Glu | Arg | Ser | Leu | Leu |
| | 130 | | | | | 135 | | | | | 140 | | | | |
| Leu | Ala | Asp | Leu | Asp | Lys | Glu | Glu | Lys | Glu | Lys | Asp | Trp | Tyr | Tyr | Ala |
| 145 | | | | | 150 | | | | | 155 | | | | | 160 |
| Gln | Leu | Gln | Asn | Leu | Thr | Lys | Arg | Ile | Asp | Ser | Leu | Pro | Leu | Thr | Glu |
| | | | | 165 | | | | | 170 | | | | | 175 | |
| Asn | Phe | Ser | Leu | Gln | Thr | Asp | Met | Thr | Arg | Arg | Gln | Leu | Glu | Tyr | Glu |
| | | | 180 | | | | | 185 | | | | | 190 | | |
| Ala | Arg | Gln | Ile | Arg | Val | Ala | Met | Glu | Glu | Gln | Leu | Gly | Thr | Cys | Gln |
| | | 195 | | | | | 200 | | | | | 205 | | | |
| Asp | Met | Glu | Lys | Arg | Ala | Gln | Arg | Arg | Ile | Ala | Arg | Ile | Gln | Gln | Ile |
| | 210 | | | | | 215 | | | | | 220 | | | | |
| Glu | Lys | Asp | Ile | Leu | Arg | Ile | Arg | Gln | Leu | Leu | Gln | Ser | Gln | Ala | Thr |
| 225 | | | | | 230 | | | | | 235 | | | | | 240 |
| Glu | Ala | Glu | Arg | Ser | Ser | Gln | Asn | Lys | His | Glu | Thr | Gly | Ser | His | Asp |
| | | | | 245 | | | | | 250 | | | | | 255 | |
| Ala | Glu | Arg | Gln | Asn | Glu | Gly | Gln | Gly | Val | Gly | Glu | Ile | Asn | Met | Ala |
| | | | 260 | | | | | 265 | | | | | 270 | | |
| Thr | Ser | Gly | Asn | Gly | Gln | Gly | Ser | Thr | Thr | Arg | Met | Asp | His | Glu | Thr |
| | | 275 | | | | | 280 | | | | | 285 | | | |
| Ala | Ser | Val | Leu | Ser | Ser | Ser | Thr | His | Ser | Ala | Pro | Arg | Arg | Leu |
| | 290 | | | | | 295 | | | | | 300 | | | | |
| Thr | Ser | His | Leu | Gly | Thr | Lys | Val | Glu | Met | Val | Tyr | Ser | Leu | Leu | Ser |
| 305 | | | | | 310 | | | | | 315 | | | | | 320 |
| Met | Leu | Gly | Thr | His | Asp | Lys | Asp | Met | Ser | Arg | Thr | Leu | Leu | Ala |
| | | | | 325 | | | | | 330 | | | | | 335 | |
| Met | Ser | Ser | Ser | Gln | Asp | Ser | Cys | Ile | Ser | Met | Arg | Gln | Ser | Gly | Cys |
| | | | 340 | | | | | 345 | | | | | 350 | | |
| Leu | Pro | Leu | Leu | Ile | Gln | Leu | Leu | His | Gly | Asn | Asp | Lys | Asp | Ser | Val |
| | | 355 | | | | | 360 | | | | | 365 | | | |
| Leu | Leu | Gly | Asn | Ser | Arg | Gly | Ser | Lys | Glu | Ala | Arg | Ala | Arg | Ala | Ser |
| | 370 | | | | | 375 | | | | | 380 | | | | |
| Ala | Ala | Leu | His | Asn | Ile | Ile | His | Ser | Gln | Pro | Asp | Asp | Lys | Arg | Gly |
| 385 | | | | | 390 | | | | | 395 | | | | | 400 |
| Arg | Arg | Glu | Ile | Arg | Val | Leu | His | Leu | Leu | Glu | Gln | Ile | Arg | Ala | Tyr |

```
                          405                      410                      415
Cys  Glu  Thr  Cys  Trp  Glu  Trp  Gln  Glu  Ala  His  Glu  Pro  Gly  Met  Asp
               420                      425                      430

Gln  Asp  Lys  Asn  Pro  Met  Pro  Ala  Pro  Val  Glu  His  Gln  Ile  Cys  Pro
               435                      440                      445

Ala  Val  Cys  Val  Leu  Met  Lys  Leu  Ser  Phe  Asp  Glu  His  Arg  His
450                      455                      460

Ala  Met  Asn  Glu  Leu  Gly  Gly  Leu  Gln  Ala  Ile  Ala  Glu  Leu  Leu  Gln
465                      470                      475                      480

Val  Asp  Cys  Glu  Met  Tyr  Gly  Leu  Thr  Asn  Asp  His  Tyr  Ser  Ile  Thr
               485                      490                      495

Leu  Arg  Arg  Tyr  Ala  Gly  Met  Ala  Leu  Thr  Asn  Leu  Thr  Phe  Gly  Asp
               500                      505                      510

Val  Ala  Asn  Lys  Ala  Thr  Leu  Cys  Ser  Met  Lys  Gly  Cys  Met  Arg  Ala
               515                      520                      525

Leu  Val  Ala  Gln  Leu  Lys  Ser  Glu  Ser  Glu  Asp  Leu  Gln  Gln  Val  Ile
530                      535                      540

Ala  Ser  Val  Leu  Arg  Asn  Leu  Ser  Trp  Arg  Ala  Asp  Val  Asn  Ser  Lys
545                      550                      555                      560

Lys  Thr  Leu  Arg  Glu  Val  Gly  Ser  Val  Lys  Ala  Leu  Met  Glu  Cys  Ala
               565                      570                      575

Leu  Glu  Val  Lys  Lys  Glu  Ser  Thr  Leu  Lys  Ser  Val  Leu  Ser  Ala  Leu
               580                      585                      590

Trp  Asn  Leu  Ser  Ala  His  Cys  Thr  Glu  Asn  Lys  Ala  Asp  Ile  Cys  Ala
               595                      600                      605

Val  Asp  Gly  Ala  Leu  Ala  Phe  Leu  Val  Gly  Thr  Leu  Thr  Tyr  Arg  Ser
610                      615                      620

Gln  Thr  Asn  Thr  Leu  Ala  Ile  Ile  Glu  Ser  Gly  Gly  Ile  Leu  Arg
625                      630                      635                      640

Asn  Val  Ser  Ser  Leu  Ile  Ala  Thr  Asn  Glu  Asp  His  Arg  Gln  Ile  Leu
               645                      650                      655

Arg  Glu  Asn  Asn  Cys  Leu  Gln  Thr  Leu  Leu  Gln  His  Leu  Lys  Ser  His
               660                      665                      670

Ser  Leu  Thr  Ile  Val  Ser  Asn  Ala  Cys  Gly  Thr  Leu  Trp  Asn  Leu  Ser
               675                      680                      685

Ala  Arg  Asn  Pro  Lys  Asp  Gln  Glu  Ala  Leu  Trp  Asp  Met  Gly  Ala  Val
               690                      695                      700

Ser  Met  Leu  Lys  Asn  Leu  Ile  His  Ser  Lys  His  Lys  Met  Ile  Ala  Met
705                      710                      715                      720

Gly  Ser  Ala  Ala  Ala  Leu  Arg  Asn  Leu  Met  Ala  Asn  Arg  Pro  Ala  Lys
                         725                      730                      735

Tyr  Lys  Asp  Ala  Asn  Ile  Met  Ser  Pro  Gly  Ser  Ser  Leu  Pro  Ser  Leu
               740                      745                      750

His  Val  Arg  Lys  Gln  Lys  Ala  Leu  Glu  Ala  Glu  Leu  Asp  Ala  Gln  His
               755                      760                      765

Leu  Ser  Glu  Thr  Phe  Asp  Asn  Ile  Asp  Asn  Leu  Ser  Pro  Lys  Ala  Ser
     770                      775                      780

His  Arg  Ser  Lys  Gln  Arg  His  Lys  Gln  Ser  Leu  Tyr  Gly  Asp  Tyr  Val
785                      790                      795                      800

Phe  Asp  Thr  Asn  Arg  His  Asp  Asp  Asn  Arg  Ser  Asp  Asn  Phe  Asn  Thr
                    805                      810                      815

Gly  Asn  Met  Thr  Val  Leu  Ser  Pro  Tyr  Leu  Asn  Thr  Thr  Val  Leu  Pro
               820                      825                      830
```

| | | | | | | | | | | | | | |
|---|---|---|---|---|---|---|---|---|---|---|---|---|---|
|Ser|Ser|Ser 835|Ser|Ser|Arg|Gly|Ser 840|Leu|Asp|Ser|Ser 845|Arg|Ser|Glu|Lys

Asp Arg Ser Leu Glu Arg Glu Arg Gly Ile Gly Leu Gly Asn Tyr His
850 855 860

Pro Ala Thr Glu Asn Pro Gly Thr Ser Ser Lys Arg Gly Leu Gln Ile
865 870 875 880

Ser Thr Thr Ala Ala Gln Ile Ala Lys Val Met Glu Glu Val Ser Ala
885 890 895

Ile His Thr Ser Gln Glu Asp Arg Ser Ser Gly Ser Thr Thr Glu Leu
900 905 910

His Cys Val Thr Asp Glu Arg Asn Ala Leu Arg Arg Ser Ser Ala Ala
915 920 925

His Thr His Ser Asn Thr Tyr Asn Phe Thr Lys Ser Glu Asn Ser Asn
930 935 940

Arg Thr Cys Ser Met Pro Tyr Ala Lys Leu Glu Tyr Lys Arg Ser Ser
945 950 955 960

Asn Asp Ser Leu Asn Ser Val Ser Ser Asp Gly Tyr Gly Lys Arg
965 970 975

Gly Gln Met Lys Pro Ser Ile Glu Ser Tyr Ser Glu Asp Asp Glu Ser
980 985 990

Lys Phe Cys Ser Tyr Gly Gln Tyr Pro Ala Asp Leu Ala His Lys Ile
995 1000 1005

His Ser Ala Asn His Met Asp Asn Asp Gly Glu Leu Asp Thr Pro
1010 1015 1020

Ile Asn Tyr Ser Leu Lys Tyr Ser Asp Glu Gln Leu Asn Ser Gly Arg
025 1030 1035 1040

Gln Ser Pro Ser Gln Asn Glu Arg Trp Ala Arg Pro Lys His Ile Ile
1045 1050 1055

Glu Asp Glu Ile Lys Gln Ser Glu Gln Arg Gln Ser Arg Asn Gln Ser
1060 1065 1070

Thr Thr Tyr Pro Val Tyr Thr Glu Ser Thr Asp Asp Lys His Leu Lys
1075 1080 1085

Phe Gln Pro His Phe Gly Gln Gln Glu Cys Val Ser Pro Tyr Arg Ser
1090 1095 1100

Arg Gly Ala Asn Gly Ser Glu Thr Asn Arg Val Gly Ser Asn His Gly
105 1110 1115 1120

Ile Asn Gln Asn Val Ser Gln Ser Leu Cys Gln Glu Asp Asp Tyr Glu
1125 1130 1135

Asp Asp Lys Pro Thr Asn Tyr Ser Glu Arg Tyr Ser Glu Glu Glu Gln
1140 1145 1150

His Glu Glu Glu Glu Arg Pro Thr Asn Tyr Ser Ile Lys Tyr Asn Glu
1155 1160 1165

Glu Lys Arg His Val Asp Gln Pro Ile Asp Tyr Ser Leu Lys Tyr Ala
1170 1175 1180

Thr Asp Ile Pro Ser Ser Gln Lys Gln Ser Phe Ser Phe Ser Lys Ser
185 1190 1195 1200

Ser Ser Gly Gln Ser Ser Lys Thr Glu His Met Ser Ser Ser Ser Glu
1205 1210 1215

Asn Thr Ser Thr Pro Ser Ser Asn Ala Lys Arg Gln Asn Gln Leu His
1220 1225 1230

Pro Ser Ser Ala Gln Ser Arg Ser Gly Gln Pro Gln Lys Ala Ala Thr
1235 1240 1245

Cys Lys Val Ser Ser Ile Asn Gln Glu Thr Ile Gln Thr Tyr Cys Val
1250 1255 1260

```
Glu  Asp  Thr  Pro  Ile  Cys  Phe  Ser  Arg  Cys  Ser  Ser  Leu  Ser  Ser  Leu
265            1270                1275                     1280

Ser  Ser  Ala  Glu  Asp  Glu  Ile  Gly  Cys  Asn  Gln  Thr  Thr  Gln  Glu  Ala
               1285                1290                1295

Asp  Ser  Ala  Asn  Thr  Leu  Gln  Ile  Ala  Glu  Ile  Lys  Glu  Lys  Ile  Gly
               1300                1305                1310

Thr  Arg  Ser  Ala  Glu  Asp  Pro  Val  Ser  Glu  Val  Pro  Ala  Val  Ser  Gln
          1315                1320                1325

His  Pro  Arg  Thr  Lys  Ser  Ser  Arg  Leu  Gln  Gly  Ser  Ser  Leu  Ser  Ser
          1330                1335                1340

Glu  Ser  Ala  Arg  His  Lys  Ala  Val  Glu  Phe  Ser  Ser  Gly  Ala  Lys  Ser
345            1350                1355                     1360

Pro  Ser  Lys  Ser  Gly  Ala  Gln  Thr  Pro  Lys  Ser  Pro  Pro  Glu  His  Tyr
               1365                1370                1375

Val  Gln  Glu  Thr  Pro  Leu  Met  Phe  Ser  Arg  Cys  Thr  Ser  Val  Ser  Ser
               1380                1385                1390

Leu  Asp  Ser  Phe  Glu  Ser  Arg  Ser  Ile  Ala  Ser  Ser  Val  Gln  Ser  Glu
               1395                1400                1405

Pro  Cys  Ser  Gly  Met  Val  Ser  Gly  Ile  Ile  Ser  Pro  Ser  Asp  Leu  Pro
     1410                1415                1420

Asp  Ser  Pro  Gly  Gln  Thr  Met  Pro  Pro  Ser  Arg  Ser  Lys  Thr  Pro  Pro
425            1430                1435                     1440

Pro  Pro  Pro  Gln  Thr  Ala  Gln  Thr  Lys  Arg  Glu  Val  Pro  Lys  Asn  Lys
               1445                1450                1455

Ala  Pro  Thr  Ala  Glu  Lys  Arg  Glu  Ser  Gly  Pro  Lys  Gln  Ala  Ala  Val
          1460                1465                1470

Asn  Ala  Ala  Val  Gln  Arg  Val  Gln  Val  Leu  Pro  Asp  Ala  Asp  Thr  Leu
          1475                1480                1485

Leu  His  Phe  Ala  Thr  Glu  Ser  Thr  Pro  Asp  Gly  Phe  Ser  Cys  Ser  Ser
     1490                1495                1500

Ser  Leu  Ser  Ala  Leu  Ser  Leu  Asp  Glu  Pro  Phe  Ile  Gln  Lys  Asp  Val
505            1510                1515                     1520

Glu  Leu  Arg  Ile  Met  Pro  Pro  Val  Gln  Glu  Asn  Asp  Asn  Gly  Asn  Glu
               1525                1530                1535

Thr  Glu  Ser  Glu  Gln  Pro  Lys  Glu  Ser  Asn  Glu  Asn  Gln  Glu  Lys  Glu
               1540                1545                1550

Ala  Glu  Lys  Thr  Ile  Asp  Ser  Glu  Lys  Asp  Leu  Leu  Asp  Asp  Ser  Asp
          1555                1560                1565

Asp  Asp  Asp  Ile  Glu  Ile  Leu  Glu  Glu  Cys  Ile  Ile  Ser  Ala  Met  Pro
     1570                1575                1580

Thr  Lys  Ser  Ser  Arg  Lys  Ala  Lys  Lys  Pro  Ala  Gln  Thr  Ala  Ser  Lys
585            1590                1595                     1600

Leu  Pro  Pro  Pro  Val  Ala  Arg  Lys  Pro  Ser  Gln  Leu  Pro  Val  Tyr  Lys
               1605                1610                1615

Leu  Leu  Pro  Ser  Gln  Asn  Arg  Leu  Gln  Pro  Gln  Lys  His  Val  Ser  Phe
               1620                1625                1630

Thr  Pro  Gly  Asp  Asp  Met  Pro  Arg  Val  Tyr  Cys  Val  Glu  Gly  Thr  Pro
     1635                1640                1645

Ile  Asn  Phe  Ser  Thr  Ala  Thr  Ser  Leu  Ser  Asp  Leu  Thr  Ile  Glu  Ser
     1650                1655                1660

Pro  Pro  Asn  Glu  Leu  Ala  Ala  Gly  Glu  Gly  Val  Arg  Gly  Gly  Ala  Gln
665            1670                1675                     1680

Ser  Gly  Glu  Phe  Glu  Lys  Arg  Asp  Thr  Ile  Pro  Thr  Glu  Gly  Arg  Ser
```

|  | 1685 | 1690 | 1695 |
|---|---|---|---|

Thr Asp Glu Ala Gln Gly Gly Lys Thr Ser Ser Val Thr Ile Pro Glu
           1700                    1705                1710

Leu Asp Asp Asn Lys Ala Glu Gly Asp Ile Leu Ala Glu Cys Ile
       1715                1720                1725

Asn Ser Ala Met Pro Lys Gly Lys Ser His Lys Pro Phe Arg Val Lys
       1730                1735                1740

Lys Ile Met Asp Gln Val Gln Gln Ala Ser Ala Ser Ser Ser Ala Pro
745                1750                1755                1760

Asn Lys Asn Gln Leu Asp Gly Lys Lys Lys Pro Thr Ser Pro Val
               1765                1770                1775

Lys Pro Ile Pro Gln Asn Thr Glu Tyr Arg Thr Arg Val Arg Lys Asn
           1780                1785                1790

Ala Asp Ser Lys Asn Asn Leu Asn Ala Glu Arg Val Phe Ser Asp Asn
           1795                1800                1805

Lys Asp Ser Lys Lys Gln Asn Leu Lys Asn Asn Ser Lys Asp Phe Asn
       1810                1815                1820

Asp Lys Leu Pro Asn Asn Glu Asp Arg Val Arg Gly Ser Phe Ala Phe
825                1830                1835                1840

Asp Ser Pro His His Tyr Thr Pro Ile Glu Gly Thr Pro Tyr Cys Phe
               1845                1850                1855

Ser Arg Asn Asp Ser Leu Ser Ser Leu Asp Phe Asp Asp Asp Val
           1860                1865                1870

Asp Leu Ser Arg Glu Lys Ala Glu Leu Arg Lys Ala Lys Glu Asn Lys
           1875                1880                1885

Glu Ser Glu Ala Lys Val Thr Ser His Thr Glu Leu Thr Ser Asn Gln
       1890                1895                1900

Gln Ser Ala Asn Lys Thr Gln Ala Ile Ala Lys Gln Pro Ile Asn Arg
905                1910                1915                1920

Gly Gln Pro Lys Pro Ile Leu Gln Lys Gln Ser Thr Phe Pro Gln Ser
               1925                1930                1935

Ser Lys Asp Ile Pro Asp Arg Gly Ala Ala Thr Asp Glu Lys Leu Gln
           1940                1945                1950

Asn Phe Ala Ile Glu Asn Thr Pro Val Cys Phe Ser His Asn Ser Ser
       1955                1960                1965

Leu Ser Ser Leu Ser Asp Ile Asp Gln Glu Asn Asn Asn Lys Glu Asn
       1970                1975                1980

Glu Pro Ile Lys Glu Thr Glu Pro Pro Asp Ser Gln Gly Glu Pro Ser
985                1990                1995                2000

Lys Pro Gln Ala Ser Gly Tyr Ala Pro Lys Ser Phe His Val Glu Asp
               2005                2010                2015

Thr Pro Val Cys Phe Ser Arg Asn Ser Ser Leu Ser Ser Leu Ser Ile
               2020                2025                2030

Asp Ser Glu Asp Asp Leu Leu Gln Glu Cys Ile Ser Ser Ala Met Pro
       2035                2040                2045

Lys Lys Lys Lys Pro Ser Arg Leu Lys Gly Asp Asn Glu Lys His Ser
       2050                2055                2060

Pro Arg Asn Met Gly Gly Ile Leu Gly Glu Asp Leu Thr Leu Asp Leu
065                2070                2075                2080

Lys Asp Ile Gln Arg Pro Asp Ser Glu His Gly Leu Ser Pro Asp Ser
               2085                2090                2095

Glu Asn Phe Asp Trp Lys Ala Ile Gln Glu Gly Ala Asn Ser Ile Val
           2100                2105                2110

```
Ser  Ser  Leu  His  Gln  Ala  Ala  Ala  Ala  Ala  Cys  Leu  Ser  Arg  Gln  Ala
         2115                2120                          2125

Ser  Ser  Asp  Ser  Asp  Ser  Ile  Leu  Ser  Leu  Lys  Ser  Gly  Ile  Ser  Leu
         2130                2135                     2140

Gly  Ser  Pro  Phe  His  Leu  Thr  Pro  Asp  Gln  Glu  Glu  Lys  Pro  Phe  Thr
 145                     2150                2155                          2160

Ser  Asn  Lys  Gly  Pro  Arg  Ile  Leu  Lys  Pro  Gly  Glu  Lys  Ser  Thr  Leu
                    2165                2170                          2175

Glu  Thr  Lys  Lys  Ile  Glu  Ser  Glu  Ser  Lys  Gly  Ile  Lys  Gly  Gly  Lys
         2180                2185                          2190

Lys  Val  Tyr  Lys  Ser  Leu  Ile  Thr  Gly  Lys  Val  Arg  Ser  Asn  Ser  Glu
         2195                2200                          2205

Ile  Ser  Gly  Gln  Met  Lys  Gln  Pro  Leu  Gln  Ala  Asn  Met  Pro  Ser  Ile
         2210                2215                     2220

Ser  Arg  Gly  Arg  Thr  Met  Ile  His  Ile  Pro  Gly  Val  Arg  Asn  Ser  Ser
 225                     2230                2235                          2240

Ser  Ser  Thr  Ser  Pro  Val  Ser  Lys  Lys  Gly  Pro  Pro  Leu  Lys  Thr  Pro
                    2245                2250                          2255

Ala  Ser  Lys  Ser  Pro  Ser  Glu  Gly  Gln  Thr  Ala  Thr  Thr  Ser  Pro  Arg
         2260                2265                          2270

Gly  Ala  Lys  Pro  Ser  Val  Lys  Ser  Glu  Leu  Ser  Pro  Val  Ala  Arg  Gln
         2275                2280                          2285

Thr  Ser  Gln  Ile  Gly  Gly  Ser  Ser  Lys  Ala  Pro  Ser  Arg  Ser  Gly  Ser
         2290                2295                          2300

Arg  Asp  Ser  Thr  Pro  Ser  Arg  Pro  Ala  Gln  Gln  Pro  Leu  Ser  Arg  Pro
 305                     2310                2315                          2320

Ile  Gln  Ser  Pro  Gly  Arg  Asn  Ser  Ile  Ser  Pro  Gly  Arg  Asn  Gly  Ile
                    2325                2330                          2335

Ser  Pro  Pro  Asn  Lys  Leu  Ser  Gln  Leu  Pro  Arg  Thr  Ser  Ser  Pro  Ser
         2340                2345                          2350

Thr  Ala  Ser  Thr  Lys  Ser  Ser  Gly  Ser  Gly  Lys  Met  Ser  Tyr  Thr  Ser
         2355                2360                          2365

Pro  Gly  Arg  Gln  Met  Ser  Gln  Gln  Asn  Leu  Thr  Lys  Gln  Thr  Gly  Leu
         2370                2375                          2380

Ser  Lys  Asn  Ala  Ser  Ser  Ile  Pro  Arg  Ser  Glu  Ser  Ala  Ser  Lys  Gly
 385                     2390                2395                          2400

Leu  Asn  Gln  Met  Asn  Asn  Gly  Asn  Gly  Ala  Asn  Lys  Lys  Val  Glu  Leu
                    2405                2410                          2415

Ser  Arg  Met  Ser  Ser  Thr  Lys  Ser  Ser  Gly  Ser  Glu  Ser  Asp  Arg  Ser
         2420                2425                          2430

Glu  Arg  Pro  Val  Leu  Val  Arg  Gln  Ser  Thr  Phe  Ile  Lys  Glu  Ala  Pro
         2435                2440                          2445

Ser  Pro  Thr  Leu  Arg  Arg  Lys  Leu  Glu  Glu  Ser  Ala  Ser  Phe  Glu  Ser
         2450                2455                          2460

Leu  Ser  Pro  Ser  Ser  Arg  Pro  Ala  Ser  Pro  Thr  Arg  Ser  Gln  Ala  Gln
 465                     2470                2475                          2480

Thr  Pro  Val  Leu  Ser  Pro  Ser  Leu  Pro  Asp  Met  Ser  Leu  Ser  Thr  His
                    2485                2490                          2495

Ser  Ser  Val  Gln  Ala  Gly  Gly  Trp  Arg  Lys  Leu  Pro  Pro  Asn  Leu  Ser
         2500                2505                          2510

Pro  Thr  Ile  Glu  Tyr  Asn  Asp  Gly  Arg  Pro  Ala  Lys  Arg  His  Asp  Ile
         2515                2520                          2525

Ala  Arg  Ser  His  Ser  Glu  Ser  Pro  Ser  Arg  Leu  Pro  Ile  Asn  Arg  Ser
         2530                2535                          2540
```

Gly Thr Trp Lys Arg Glu His Ser Lys His Ser Ser Leu Pro Arg
545                 2550            2555                2560

Val Ser Thr Trp Arg Arg Thr Gly Ser Ser Ser Ile Leu Ser Ala
            2565            2570                2575

Ser Ser Glu Ser Ser Glu Lys Ala Lys Ser Glu Asp Glu Lys His Val
        2580            2585            2590

Asn Ser Ile Ser Gly Thr Lys Gln Ser Lys Glu Asn Gln Val Ser Ala
        2595            2600            2605

Lys Gly Thr Trp Arg Lys Ile Lys Glu Asn Glu Phe Ser Pro Thr Asn
    2610            2615            2620

Ser Thr Ser Gln Thr Val Ser Ser Gly Ala Thr Asn Gly Ala Glu Ser
625             2630            2635                2640

Lys Thr Leu Ile Tyr Gln Met Ala Pro Ala Val Ser Lys Thr Glu Asp
            2645            2650            2655

Val Trp Val Arg Ile Glu Asp Cys Pro Ile Asn Asn Pro Arg Ser Gly
            2660            2665            2670

Arg Ser Pro Thr Gly Asn Thr Pro Pro Val Ile Asp Ser Val Ser Glu
        2675            2680            2685

Lys Ala Asn Pro Asn Ile Lys Asp Ser Lys Asp Asn Gln Ala Lys Gln
2690            2695            2700

Asn Val Gly Asn Gly Ser Val Pro Met Arg Thr Val Gly Leu Glu Asn
705             2710            2715                2720

Arg Leu Asn Ser Phe Ile Gln Val Asp Ala Pro Asp Gln Lys Gly Thr
            2725            2730            2735

Glu Ile Lys Pro Gly Gln Asn Asn Pro Val Pro Val Ser Glu Thr Asn
        2740            2745            2750

Glu Ser Ser Ile Val Glu Arg Thr Pro Phe Ser Ser Ser Ser Ser Ser
        2755            2760            2765

Lys His Ser Ser Pro Ser Gly Thr Val Ala Ala Arg Val Thr Pro Phe
    2770            2775            2780

Asn Tyr Asn Pro Ser Pro Arg Lys Ser Ser Ala Asp Ser Thr Ser Ala
785             2790            2795                2800

Arg Pro Ser Gln Ile Pro Thr Pro Val Asn Asn Asn Thr Lys Lys Arg
            2805            2810            2815

Asp Ser Lys Thr Asp Ser Thr Glu Ser Ser Gly Thr Gln Ser Pro Lys
        2820            2825            2830

Arg His Ser Gly Ser Tyr Leu Val Thr Ser Val
        2835            2840

( 2 ) INFORMATION FOR SEQ ID NO:3:

( i ) SEQUENCE CHARACTERISTICS:
      ( A ) LENGTH: 3172 base pairs
      ( B ) TYPE: nucleic acid
      ( C ) STRANDEDNESS: double
      ( D ) TOPOLOGY: linear ( i i ) MOLECULE TYPE: cDNA ( v i ) ORIGINAL SOURCE:
      ( A ) ORGANISM: Homo sapiens ( v i i ) IMMEDIATE SOURCE:
      ( B ) CLONE: DP1(TB2)

( i x ) FEATURE:
      ( A ) NAME/KEY: CDS
      ( B ) LOCATION: 1..630

( x i ) SEQUENCE DESCRIPTION: SEQ ID NO:3:

| | | | | | | | | | | | | | | | | |
|---|---|---|---|---|---|---|---|---|---|---|---|---|---|---|---|---|
|GCA|GTC|GCC|GCT|CCA|GTC|TAT|CCG|GCA|CTA|GGA|ACA|GCC|CCG|GGN|GGC|48|
|Ala|Val|Ala|Ala|Pro|Val|Tyr|Pro|Ala|Leu|Gly|Thr|Ala|Pro|Gly|Gly| |
|1| | | |5| | | |10| | | | | |15| | |
|GAG|ACG|GTC|CCC|GCC|ATG|TCT|GCG|GCC|ATG|AGG|GAG|AGG|TTC|GAC|CGG|96|
|Glu|Thr|Val|Pro|Ala|Met|Ser|Ala|Ala|Met|Arg|Glu|Arg|Phe|Asp|Arg| |
| | | |20| | | | |25| | | | |30| | | |
|TTC|CTG|CAC|GAG|AAG|AAC|TGC|ATG|ACT|GAC|CTT|CTG|GCC|AAG|CTC|GAG|144|
|Phe|Leu|His|Glu|Lys|Asn|Cys|Met|Thr|Asp|Leu|Leu|Ala|Lys|Leu|Glu| |
| | |35| | | | |40| | | | |45| | | | |
|GCC|AAA|ACC|GGC|GTG|AAC|AGG|AGC|TTC|ATC|GCT|CTT|GGT|GTC|ATC|GGA|192|
|Ala|Lys|Thr|Gly|Val|Asn|Arg|Ser|Phe|Ile|Ala|Leu|Gly|Val|Ile|Gly| |
| |50| | | | |55| | | |60| | | | | | |
|CTG|GTG|GCC|TTG|TAC|CTG|GTG|TTC|GGT|TAT|GGA|GCC|TCT|CTC|CTC|TGC|240|
|Leu|Val|Ala|Leu|Tyr|Leu|Val|Phe|Gly|Tyr|Gly|Ala|Ser|Leu|Leu|Cys| |
|65| | | | |70| | | | |75| | | | |80| |
|AAC|CTG|ATA|GGA|TTT|GGC|TAC|CCA|GCC|TAC|ATC|TCA|ATT|AAA|GCT|ATA|288|
|Asn|Leu|Ile|Gly|Phe|Gly|Tyr|Pro|Ala|Tyr|Ile|Ser|Ile|Lys|Ala|Ile| |
| | | | |85| | | | |90| | | | |95| | |
|GAG|AGT|CCC|AAC|AAA|GAA|GAT|GAT|ACC|CAG|TGG|CTG|ACC|TAC|TGG|GTA|336|
|Glu|Ser|Pro|Asn|Lys|Glu|Asp|Asp|Thr|Gln|Trp|Leu|Thr|Tyr|Trp|Val| |
| | | |100| | | | |105| | | | |110| | | |
|GTG|TAT|GGT|GTG|TTC|AGC|ATT|GCT|GAA|TTC|TTC|TCT|GAT|ATC|TTC|CTG|384|
|Val|Tyr|Gly|Val|Phe|Ser|Ile|Ala|Glu|Phe|Phe|Ser|Asp|Ile|Phe|Leu| |
| | |115| | | | |120| | | | |125| | | | |
|TCA|TGG|TTC|CCC|TTC|TAC|TAC|ATG|CTG|AAG|TGT|GGC|TTC|CTG|TTG|TGG|432|
|Ser|Trp|Phe|Pro|Phe|Tyr|Tyr|Met|Leu|Lys|Cys|Gly|Phe|Leu|Leu|Trp| |
| |130| | | | |135| | | | |140| | | | | |
|TGC|ATG|GCC|CCG|AGC|CCT|TCT|AAT|GGG|GCT|GAA|CTG|CTC|TAC|AAG|CGC|480|
|Cys|Met|Ala|Pro|Ser|Pro|Ser|Asn|Gly|Ala|Glu|Leu|Leu|Tyr|Lys|Arg| |
|145| | | | |150| | | | |155| | | | |160| |
|ATC|ATC|CGT|CCT|TTC|TTC|CTG|AAG|CAC|GAG|TCC|CAG|ATG|GAC|AGT|GTG|528|
|Ile|Ile|Arg|Pro|Phe|Phe|Leu|Lys|His|Glu|Ser|Gln|Met|Asp|Ser|Val| |
| | | |165| | | | |170| | | | |175| | | |
|GTC|AAG|GAC|CTT|AAA|GAC|AAG|TCC|AAA|GAG|ACT|GCA|GAT|GCC|ATC|ACT|576|
|Val|Lys|Asp|Leu|Lys|Asp|Lys|Ser|Lys|Glu|Thr|Ala|Asp|Ala|Ile|Thr| |
| | |180| | | | |185| | | | |190| | | | |
|AAA|GAA|GCG|AAG|AAA|GCT|ACC|GTG|AAT|TTA|CTG|GGT|GAA|GAA|AAG|AAG|624|
|Lys|Glu|Ala|Lys|Lys|Ala|Thr|Val|Asn|Leu|Leu|Gly|Glu|Glu|Lys|Lys| |
| |195| | | | |200| | | | |205| | | | | |
|AGC|ACC|TAAACCAGAC|TAAACCAGAC|TGGATGGAAA|CTTCCTGCCC|TCTCTGTACC| | | | | | | | | |680|
|Ser|Thr| | | | | | | | | | | | | | | |
| |210| | | | | | | | | | | | | | | |

| | | | | |
|---|---|---|---|---|
|TTCCTACTGG|AGCTTGATGT|TATATTAGGG|ACTGTGGTAT|AATTATTTTA|ATAATGTTGC|740|
|CTTGGAAACA|TTTTTGAGAT|ATTAAAGATT|GGAATGTGTT|GTAAGTTTCT|TTGCTTACTT|800|
|TTACTGTCTA|TATATATAGG|GAGCACTTTA|AACTTAATGC|AGTGGGCAGT|GTCCACGTTT|860|
|TTGGAAAATG|TATTTTGCCT|CTGGGTAGGA|AAAGATGTAT|GTTGCTATCC|TGCAGGAAAT|920|
|ATAAACTTAA|AATAAAATTA|TATACCCCAC|AGGCTGTGTA|CTTTACTGGG|CTCTCCCTGC|980|
|ACGSATTTTC|TCTGTAGTTA|CATTTAGGRT|AATCTTTATG|GTTCTACTTC|CTRTAATGTA|1040|
|CAATTTTATA|TAATTCNGRA|ATGTTTTAA|TGTATTTGTG|CACATGTACA|TATGGAAATG|1100|
|TTACTGTCTG|ACTACANCAT|GCATCATGCT|CATGGGGAGG|GAGCAGGGGA|AGGTTGTATG|1160|
|TGTCATTTAT|AACTTCTGTA|CAGTAAGACC|ACCTGCCAAA|AGCTGGAGGA|ACCATTGTGC|1220|
|TGGTGTGGTC|TACTAAATAA|TACTTTAGGA|AATACGTGAT|TAATATGCAA|GTGAACAAAG|1280|
|TGAGAAATGA|AATCGAATGG|AGATTGGCCT|GGTTGTTTCC|GTAGTATATG|GCATATGAAT|1340|
|ACCAGGATAG|CTTTATAAAG|CAGTTAGTTA|GTTAGTTACT|CACTCTAGTG|ATAAATCGGG|1400|

| | | | | | | |
|---|---|---|---|---|---|---|
| AAATTTACAC | ACACACACAC | ACACACACAC | ACACACACAC | ACACACACAC | ACACACACAG | 1460 |
| AGTACCCTGT | AACTCTCAAT | TCCCTGAAAA | ACTAGTAATA | CTGTCTTATC | TGCTATAAAC | 1520 |
| TTTACATATT | TGTCTATTGT | CAAGATGCTA | CANTGGAMNC | CATTTCTGGT | TTTATCTTCA | 1580 |
| NAGSGGAGAN | ACATGTTGAT | TTAGTCTTCT | TTCCCAATCT | TCTTTTTAA | MCCAGTTTNA | 1640 |
| GGMNCTTCTG | RAGATTTGYC | CACCTCTGAT | TACATGTATG | TTCTYGTTTG | TATCATKAGC | 1700 |
| AACAACATGC | TAATGRCGAC | ACCTAGCTCT | RAGMGCAATT | CTGGGAGANT | GARAGGNWGT | 1760 |
| ATARAGTMNC | CCATAATCTG | CTTGGCAATA | GTTAAGTCAA | TCTATCTTCA | GTTTTTCTCT | 1820 |
| GGCCTTTAAG | GTCAAACACA | AGAGGCTTCC | CTAGTTTACA | AGTCAGAGTC | ACTTGTAGTC | 1880 |
| CATTTAAATG | CCCTCATCCG | TATTCTTTGT | GTTGATAAGC | TGCACAKGAC | TACATAGTAA | 1940 |
| GTACAGANCA | GTAAAGTTAA | NNCGGATGTC | TCCATTGATC | TGCCAANTCG | NTATAGAGAG | 2000 |
| CAATTGTCT | GGACTAGAAA | ATCTGAGTTT | TACACCATAC | TGTTAAGAGT | CCTTTTGAAT | 2060 |
| TAAACTAGAC | TAAAACAAGT | GTATAACTAA | ACTAACAAGA | TTAAATATCC | AGCCAGTACA | 2120 |
| GTATTTTTA | AGGCAAATAA | AGATGATTAG | CTCACCTTGA | GNTAACAATC | AGGTAAGATC | 2180 |
| ATNACAATGT | CTCATGATGT | NAANAATATT | AAAGATATCA | ATACTAAGTG | ACAGTATCAC | 2240 |
| NNCTAATATA | ATATGGATCA | GAGCATTTAT | TTTGGGGAGG | AAAACAGTGG | TGATTACCGG | 2300 |
| CATTTTATTA | AACTTAAAAC | TTTGTAGAAA | GCAAACAAAA | TTGTTCTTGG | GAGAAAATCA | 2360 |
| ACTTTTAGAT | TAAAAAAATT | TTAAGTAWCT | AGGAGTATTT | AAATCCTTTT | CCCATAAATA | 2420 |
| AAAGTACAGT | TTTCTTGGTG | GCAGAATGAA | AATCAGCAAC | NTCTAGCATA | TAGACTATAT | 2480 |
| AATCAGATTG | ACAGCATATA | GAATATATTA | TCAGACAAGA | TGAGGAGGTA | CAAAAGTTAC | 2540 |
| TATTGCTCAT | AATGACTTAC | AGGCTAAAAN | TAGNTNTAAA | ATACTATATT | AAATTCTGAA | 2600 |
| TGCAATTTTT | TTTTGTTCCC | TTGAGACCAA | AATTTAAGTT | AACTGTTGCT | GGCAGTCTAA | 2660 |
| GTGTAAATGT | TAACAGCAGG | AGAAGTTAAG | AATTGAGCAG | TTCTGTTGCA | TGATTTCCCA | 2720 |
| AATGAAATAC | TGCCTTGGCT | AGAGTTTGAA | AAACTAATTG | AGCCTGTGCC | TGGCTAGAAA | 2780 |
| ACAAGCGTTT | ATTTGAATGT | GAATAGTGTT | TCAAGGTAT | GTAGTTACAG | AATTCCTACC | 2840 |
| AAACAGCTTA | AATTCTTCAA | GAAAGAATTC | CTGCAGCAGT | TATTCCCTTA | CCTGAAGGCT | 2900 |
| TCAATCATTT | GGATCAACAA | CTGCTACTCT | CGGGAAGACT | CCTCTACTCA | CAGCTGAAGA | 2960 |
| AAATGAGCAC | ACCCTTCACA | CTGTTATCAC | CTATCCTGAA | GATGTGATAC | ACTGAATGGA | 3020 |
| AATAAATAGA | TGTAAATAAA | ATTGAGWTCT | CATTTAAAAA | AAACCATGTG | CCCAATGGGA | 3080 |
| AAATGACCTC | ATGTTGTGGT | TTAAACAGCA | ACTGCACCCA | CTAGCACAGC | CCATTGAGCT | 3140 |
| ANCCTATATA | TACATCTCTG | TCAGTGCCCC | TC | | | 3172 |

( 2 ) INFORMATION FOR SEQ ID NO:4:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Val | Ala | Ala | Pro | Val | Tyr | Pro | Ala | Leu | Gly | Thr | Ala | Pro | Gly | Gly |
|---|---|---|---|---|---|---|---|---|---|---|---|---|---|---|---|
| 1 | | | | 5 | | | | | 10 | | | | | 15 | |

| Glu | Thr | Val | Pro | Ala | Met | Ser | Ala | Ala | Met | Arg | Glu | Arg | Phe | Asp | Arg |
|---|---|---|---|---|---|---|---|---|---|---|---|---|---|---|---|
| | | | 20 | | | | | 25 | | | | | 30 | | |

| Phe | Leu | His | Glu | Lys | Asn | Cys | Met | Thr | Asp | Leu | Leu | Ala | Lys | Leu | Glu |
|---|---|---|---|---|---|---|---|---|---|---|---|---|---|---|---|

|       |       |       |       | 35    |       |       |       |       | 40    |       |       |       |       | 45    |       |       |       |
|-------|-------|-------|-------|-------|-------|-------|-------|-------|-------|-------|-------|-------|-------|-------|-------|-------|-------|

Ala Lys Thr Gly Val Asn Arg Ser Phe Ile Ala Leu Gly Val Ile Gly
    50                          55                          60

Leu Val Ala Leu Tyr Leu Val Phe Gly Tyr Gly Ala Ser Leu Leu Cys
65                          70                      75                      80

Asn Leu Ile Gly Phe Gly Tyr Pro Ala Tyr Ile Ser Ile Lys Ala Ile
                85                      90                        95

Glu Ser Pro Asn Lys Glu Asp Thr Gln Trp Leu Thr Tyr Trp Val
            100                  105               110

Val Tyr Gly Val Phe Ser Ile Ala Glu Phe Phe Ser Asp Ile Phe Leu
        115                  120                125

Ser Trp Phe Pro Phe Tyr Tyr Met Leu Lys Cys Gly Phe Leu Leu Trp
    130                     135                 140

Cys Met Ala Pro Ser Pro Ser Asn Gly Ala Glu Leu Leu Tyr Lys Arg
145                        150                   155            160

Ile Ile Arg Pro Phe Phe Leu Lys His Glu Ser Gln Met Asp Ser Val
                165                170               175

Val Lys Asp Leu Lys Asp Lys Ser Lys Glu Thr Ala Asp Ala Ile Thr
            180                  185              190

Lys Glu Ala Lys Lys Ala Thr Val Asn Leu Leu Gly Glu Glu Lys Lys
        195                  200               205

Ser Thr
    210

( 2 ) INFORMATION FOR SEQ ID NO:5:

( i ) SEQUENCE CHARACTERISTICS:
        ( A ) LENGTH: 434 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: TB1

( x i ) SEQUENCE DESCRIPTION: SEQ ID NO:5:

Val Ala Pro Val Val Val Gly Ser Gly Arg Ala Pro Arg His Pro Ala
1                5                      10                   15

Pro Ala Ala Met His Pro Arg Arg Pro Asp Gly Phe Asp Gly Leu Gly
            20                  25                   30

Tyr Arg Gly Gly Ala Arg Asp Glu Gln Gly Phe Gly Gly Ala Phe Pro
        35                  40                45

Ala Arg Ser Phe Ser Thr Gly Ser Asp Leu Gly His Trp Val Thr Thr
    50                      55                    60

Pro Pro Asp Ile Pro Gly Ser Arg Asn Leu His Trp Gly Glu Lys Ser
65                        70                      75                   80

Pro Pro Tyr Gly Val Pro Thr Thr Ser Thr Pro Tyr Glu Gly Pro Thr
                85                      90                     95

Glu Glu Pro Phe Ser Ser Gly Gly Gly Gly Ser Val Gln Gly Gln Ser
            100                  105               110

Ser Glu Gln Leu Asn Arg Phe Ala Gly Phe Gly Ile Gly Leu Ala Ser
        115                  120                125

Leu Phe Thr Glu Asn Val Leu Ala His Pro Cys Ile Val Leu Arg Arg
    130                     135                 140

| Gln | Cys | Gln | Val | Asn | Tyr | His | Ala | Gln | His | Tyr | His | Leu | Thr | Pro | Phe |
| 145 | | | | | 150 | | | | | 155 | | | | | 160 |

Thr Val Ile Asn Ile Met Tyr Ser Phe Asn Lys Thr Gln Gly Pro Arg
                    165                 170                 175

Ala Leu Trp Lys Gly Met Gly Ser Thr Phe Ile Val Gln Gly Val Thr
              180                 185                 190

Leu Gly Ala Glu Gly Ile Ile Ser Glu Phe Thr Pro Leu Pro Arg Glu
          195                 200                 205

Val Leu His Lys Trp Ser Pro Lys Gln Ile Gly Glu His Leu Leu Leu
      210                 215                 220

Lys Ser Leu Thr Tyr Val Ala Met Pro Phe Tyr Ser Ala Ser Leu
225                 230                 235                 240

Ile Glu Thr Val Gln Ser Glu Ile Ile Arg Asp Asn Thr Gly Ile Leu
              245                 250                 255

Glu Cys Val Lys Glu Gly Ile Gly Arg Val Ile Gly Met Gly Val Pro
          260                 265                 270

His Ser Lys Arg Leu Leu Pro Leu Leu Ser Leu Ile Phe Pro Thr Val
      275                 280                 285

Leu His Gly Val Leu His Tyr Ile Ile Ser Ser Val Ile Gln Lys Phe
      290                 295                 300

Val Leu Leu Ile Leu Lys Arg Lys Thr Tyr Asn Ser His Leu Ala Glu
305                 310                 315                 320

Ser Thr Ser Pro Val Gln Ser Met Leu Asp Ala Tyr Phe Pro Glu Leu
              325                 330                 335

Ile Ala Asn Phe Ala Ala Ser Leu Cys Ser Asp Val Ile Leu Tyr Pro
          340                 345                 350

Leu Glu Thr Val Leu His Arg Leu His Ile Gln Gly Thr Arg Thr Ile
          355                 360                 365

Ile Asp Asn Thr Asp Leu Gly Tyr Glu Val Leu Pro Ile Asn Thr Gln
    370                 375                 380

Tyr Glu Gly Met Arg Asp Cys Ile Asn Thr Ile Arg Gln Glu Glu Gly
385                 390                 395                 400

Val Phe Gly Phe Tyr Lys Gly Phe Gly Ala Val Ile Ile Gln Tyr Thr
              405                 410                 415

Leu His Ala Ala Val Leu Gln Ile Thr Lys Ile Ile Tyr Ser Thr Leu
          420                 425                 430

Leu Gln (2) INFORMATION FOR SEQ ID NO:6:

(i) SEQUENCE CHARACTERISTICS:
      (A) LENGTH: 185 amino acids
      (B) TYPE: amino acid
      (C) STRANDEDNESS: single
      (D) TOPOLOGY: linear (ii) MOLECULE TYPE: protein (vi) ORIGINAL SOURCE:
      (A) ORGANISM: Homo sapiens (vii) IMMEDIATE SOURCE:
      (B) CLONE: YS-39(TB2)

(xi) SEQUENCE DESCRIPTION: SEQ ID NO:6:

Glu Leu Arg Arg Phe Asp Arg Phe Leu His Glu Lys Asn Cys Met Thr
1                   5                   10                  15

Asp Leu Leu Ala Lys Leu Glu Ala Lys Thr Gly Val Asn Arg Ser Phe

|   |   |   |   |   | 20 |   |   |   |   | 25 |   |   |   |   | 30 |   |   |
|---|---|---|---|---|---|---|---|---|---|---|---|---|---|---|---|---|---|

Ile Ala Leu Gly Val Ile Gly Leu Val Ala Leu Tyr Leu Val Phe Gly
          35                    40                   45

Tyr Gly Ala Ser Leu Leu Cys Asn Leu Ile Gly Phe Gly Tyr Pro Ala
         50                   55                   60

Tyr Ile Ser Ile Lys Ala Ile Glu Ser Pro Asn Lys Glu Asp Asp Thr
65                       70                  75                  80

Gln Trp Leu Thr Tyr Trp Val Val Tyr Gly Val Phe Ser Ile Ala Glu
                85                   90                   95

Phe Phe Ser Asp Ile Phe Leu Ser Trp Phe Pro Phe Tyr Tyr Ile Leu
                100                  105                 110

Lys Cys Gly Phe Leu Leu Trp Cys Met Ala Pro Ser Pro Ser Asn Gly
            115                  120                  125

Ala Glu Leu Leu Tyr Lys Arg Ile Ile Arg Pro Phe Phe Leu Lys His
    130                      135                 140

Glu Ser Gln Met Asp Ser Val Val Lys Asp Leu Lys Asp Lys Ala Lys
145                     150                  155                 160

Glu Thr Ala Asp Ala Ile Thr Lys Glu Ala Lys Lys Ala Thr Val Asn
                165                  170                 175

Leu Leu Gly Glu Glu Lys Lys Ser Thr
            180                185

(2) INFORMATION FOR SEQ ID NO:7:

(i) SEQUENCE CHARACTERISTICS:
        (A) LENGTH: 2843 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (xi) SEQUENCE DESCRIPTION: SEQ ID NO:7:

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
                100                 105                 110

Val Pro Met Gly Ser Phe Pro Arg Arg Gly Phe Val Asn Gly Ser Arg
            115                 120                 125

Glu Ser Thr Gly Tyr Leu Glu Glu Leu Glu Lys Glu Arg Ser Leu Leu
130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu

-continued

|  |  |  |  | 165 |  |  |  | 170 |  |  |  | 175 |  |  |
|---|---|---|---|---|---|---|---|---|---|---|---|---|---|---|
| Asn | Phe | Ser | Leu 180 | Gln | Thr | Asp | Met | Thr 185 | Arg | Arg | Gln | Leu 190 | Glu | Tyr | Glu |
| Ala | Arg | Gln 195 | Ile | Arg | Val | Ala | Met 200 | Glu | Glu | Gln | Leu 205 | Gly | Thr | Cys | Gln |
| Asp | Met 210 | Glu | Lys | Arg | Ala 215 | Gln | Arg | Arg | Ile | Ala 220 | Arg | Ile | Gln | Gln | Ile |
| Glu 225 | Lys | Asp | Ile | Leu | Arg 230 | Ile | Arg | Gln | Leu | Leu 235 | Gln | Ser | Gln | Ala | Thr 240 |
| Glu | Ala | Glu | Arg | Ser 245 | Ser | Gln | Asn | Lys | His 250 | Glu | Thr | Gly | Ser | His 255 | Asp |
| Ala | Glu | Arg | Gln 260 | Asn | Glu | Gly | Gln | Gly 265 | Val | Gly | Glu | Ile | Asn 270 | Met | Ala |
| Thr | Ser | Gly 275 | Asn | Gly | Gln | Gly | Ser 280 | Thr | Thr | Arg | Met | Asp 285 | His | Glu | Thr |
| Ala | Ser 290 | Val | Leu | Ser | Ser | Ser 295 | Ser | Thr | His | Ser | Ala 300 | Pro | Arg | Arg | Leu |
| Thr 305 | Ser | His | Leu | Gly | Thr 310 | Lys | Val | Glu | Met | Val 315 | Tyr | Ser | Leu | Leu | Ser 320 |
| Met | Leu | Gly | Thr | His 325 | Asp | Lys | Asp | Asp | Met 330 | Ser | Arg | Thr | Leu | Leu 335 | Ala |
| Met | Ser | Ser | Ser 340 | Gln | Asp | Ser | Cys | Ile 345 | Ser | Met | Arg | Gln | Ser 350 | Gly | Cys |
| Leu | Pro | Leu 355 | Leu | Ile | Gln | Leu | Leu 360 | His | Gly | Asn | Asp | Lys 365 | Asp | Ser | Val |
| Leu | Leu 370 | Gly | Asn | Ser | Arg | Gly 375 | Ser | Lys | Glu | Ala | Arg 380 | Ala | Arg | Ala | Ser |
| Ala 385 | Ala | Leu | His | Asn | Ile 390 | Ile | His | Ser | Gln | Pro 395 | Asp | Asp | Lys | Arg | Gly 400 |
| Arg | Arg | Glu | Ile | Arg 405 | Val | Leu | His | Leu | Leu 410 | Glu | Gln | Ile | Arg | Ala 415 | Tyr |
| Cys | Glu | Thr | Cys 420 | Trp | Glu | Trp | Gln | Glu 425 | Ala | His | Glu | Pro | Gly 430 | Met | Asp |
| Gln | Asp | Lys 435 | Asn | Pro | Met | Pro | Ala 440 | Pro | Val | Glu | His | Gln 445 | Ile | Cys | Pro |
| Ala | Val 450 | Cys | Val | Leu | Met | Lys 455 | Leu | Ser | Phe | Asp | Glu 460 | Glu | His | Arg | His |
| Ala | Met 465 | Asn | Glu | Leu | Gly | Gly 470 | Leu | Gln | Ala | Ile | Ala 475 | Glu | Leu | Leu | Gln 480 |
| Val | Asp | Cys | Glu | Met 485 | Tyr | Gly | Leu | Thr | Asn 490 | Asp | His | Tyr | Ser | Ile 495 | Thr |
| Leu | Arg | Arg | Tyr 500 | Ala | Gly | Met | Ala | Leu 505 | Thr | Asn | Leu | Thr | Phe 510 | Gly | Asp |
| Val | Ala | Asn 515 | Lys | Ala | Thr | Leu | Cys 520 | Ser | Met | Lys | Gly | Cys 525 | Met | Arg | Ala |
| Leu | Val 530 | Ala | Gln | Leu | Lys | Ser 535 | Glu | Ser | Glu | Asp | Leu 540 | Gln | Gln | Val | Ile |
| Ala 545 | Ser | Val | Leu | Arg | Asn 550 | Leu | Ser | Trp | Arg | Ala 555 | Asp | Val | Asn | Ser | Lys 560 |
| Lys | Thr | Leu | Arg | Glu 565 | Val | Gly | Ser | Val | Lys 570 | Ala | Leu | Met | Glu | Cys 575 | Ala |
| Leu | Glu | Val | Lys 580 | Lys | Glu | Ser | Thr | Leu 585 | Lys | Ser | Val | Leu | Ser 590 | Ala | Leu |

| | | | | | | | | | | | | |
|---|---|---|---|---|---|---|---|---|---|---|---|---|
| Trp | Asn | Leu | Ser | Ala | His | Cys | Thr | Glu | Asn | Lys | Ala | Asp | Ile | Cys | Ala |
| | | 595 | | | | | 600 | | | | 605 | | | | |
| Val | Asp | Gly | Ala | Leu | Ala | Phe | Leu | Val | Gly | Thr | Leu | Thr | Tyr | Arg | Ser |
| | 610 | | | | | 615 | | | | | 620 | | | | |
| Gln | Thr | Asn | Thr | Leu | Ala | Ile | Ile | Glu | Ser | Gly | Gly | Ile | Leu | Arg |
| 625 | | | | | 630 | | | | | 635 | | | | 640 |
| Asn | Val | Ser | Ser | Leu | Ile | Ala | Thr | Asn | Glu | Asp | His | Arg | Gln | Ile | Leu |
| | | | | 645 | | | | | 650 | | | | | 655 | |
| Arg | Glu | Asn | Asn | Cys | Leu | Gln | Thr | Leu | Leu | Gln | His | Leu | Lys | Ser | His |
| | | | 660 | | | | | 665 | | | | 670 | | | |
| Ser | Leu | Thr | Ile | Val | Ser | Asn | Ala | Cys | Gly | Thr | Leu | Trp | Asn | Leu | Ser |
| | | 675 | | | | | 680 | | | | | 685 | | | |
| Ala | Arg | Asn | Pro | Lys | Asp | Gln | Glu | Ala | Leu | Trp | Asp | Met | Gly | Ala | Val |
| | 690 | | | | | 695 | | | | | 700 | | | | |
| Ser | Met | Leu | Lys | Asn | Leu | Ile | His | Ser | Lys | His | Lys | Met | Ile | Ala | Met |
| 705 | | | | | 710 | | | | | 715 | | | | | 720 |
| Gly | Ser | Ala | Ala | Ala | Leu | Arg | Asn | Leu | Met | Ala | Asn | Arg | Pro | Ala | Lys |
| | | | | 725 | | | | | 730 | | | | | 735 | |
| Tyr | Lys | Asp | Ala | Asn | Ile | Met | Ser | Pro | Gly | Ser | Ser | Leu | Pro | Ser | Leu |
| | | | 740 | | | | | 745 | | | | | 750 | | |
| His | Val | Arg | Lys | Gln | Lys | Ala | Leu | Glu | Ala | Glu | Leu | Asp | Ala | Gln | His |
| | | 755 | | | | | 760 | | | | | 765 | | | |
| Leu | Ser | Glu | Thr | Phe | Asp | Asn | Ile | Asp | Asn | Leu | Ser | Pro | Lys | Ala | Ser |
| | 770 | | | | | 775 | | | | | 780 | | | | |
| His | Arg | Ser | Lys | Gln | Arg | His | Lys | Gln | Ser | Leu | Tyr | Gly | Asp | Tyr | Val |
| 785 | | | | | 790 | | | | | 795 | | | | | 800 |
| Phe | Asp | Thr | Asn | Arg | His | Asp | Asp | Asn | Arg | Ser | Asp | Asn | Phe | Asn | Thr |
| | | | | 805 | | | | | 810 | | | | | 815 | |
| Gly | Asn | Met | Thr | Val | Leu | Ser | Pro | Tyr | Leu | Asn | Thr | Thr | Val | Leu | Pro |
| | | | 820 | | | | | 825 | | | | | 830 | | |
| Ser | Ser | Ser | Ser | Ser | Arg | Gly | Ser | Leu | Asp | Ser | Ser | Arg | Ser | Glu | Lys |
| | | | 835 | | | | | 840 | | | | | 845 | | |
| Asp | Arg | Ser | Leu | Glu | Arg | Glu | Arg | Gly | Ile | Gly | Leu | Gly | Asn | Tyr | His |
| | 850 | | | | | 855 | | | | | 860 | | | | |
| Pro | Ala | Thr | Glu | Asn | Pro | Gly | Thr | Ser | Ser | Lys | Arg | Gly | Leu | Gln | Ile |
| 865 | | | | | 870 | | | | | 875 | | | | | 880 |
| Ser | Thr | Thr | Ala | Ala | Gln | Ile | Ala | Lys | Val | Met | Glu | Glu | Val | Ser | Ala |
| | | | | 885 | | | | | 890 | | | | | 895 | |
| Ile | His | Thr | Ser | Gln | Glu | Asp | Arg | Ser | Ser | Gly | Ser | Thr | Thr | Glu | Leu |
| | | | 900 | | | | | 905 | | | | | 910 | | |
| His | Cys | Val | Thr | Asp | Glu | Arg | Asn | Ala | Leu | Arg | Arg | Ser | Ser | Ala | Ala |
| | | 915 | | | | | 920 | | | | | 925 | | | |
| His | Thr | His | Ser | Asn | Thr | Tyr | Asn | Phe | Thr | Lys | Ser | Glu | Asn | Ser | Asn |
| | 930 | | | | | 935 | | | | | 940 | | | | |
| Arg | Thr | Cys | Ser | Met | Pro | Tyr | Ala | Lys | Leu | Glu | Tyr | Lys | Arg | Ser | Ser |
| 945 | | | | | 950 | | | | | 955 | | | | | 960 |
| Asn | Asp | Ser | Leu | Asn | Ser | Val | Ser | Ser | Ser | Asp | Gly | Tyr | Gly | Lys | Arg |
| | | | | 965 | | | | | 970 | | | | | 975 | |
| Gly | Gln | Met | Lys | Pro | Ser | Ile | Glu | Ser | Tyr | Ser | Glu | Asp | Asp | Glu | Ser |
| | | | 980 | | | | | 985 | | | | | 990 | | |
| Lys | Phe | Cys | Ser | Tyr | Gly | Gln | Tyr | Pro | Ala | Asp | Leu | Ala | His | Lys | Ile |
| | | 995 | | | | | 1000 | | | | | 1005 | | | |
| His | Ser | Ala | Asn | His | Met | Asp | Asp | Asn | Asp | Gly | Glu | Leu | Asp | Thr | Pro |
| | | | | 1010 | | | | | 1015 | | | | | 1020 | |

-continued

```
Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Glu Lys Ile Gly
            1300                1305                1310

Thr Arg Ser Ala Glu Asp Pro Val Ser Glu Val Pro Ala Val Ser Gln
        1315                1320                1325

His Pro Arg Thr Lys Ser Ser Arg Leu Gln Gly Ser Ser Leu Ser Ser
1330                1335                1340

Glu Ser Ala Arg His Lys Ala Val Glu Phe Ser Ser Gly Ala Lys Ser
1345                1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
        1395                1400                1405

Pro Cys Ser Gly Met Val Ser Gly Ile Ile Ser Pro Ser Asp Leu Pro
    1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
```

```
                    1445                      1450                       1455
Ala  Pro  Thr  Ala  Glu  Lys  Arg  Glu  Ser  Gly  Pro  Lys  Gln  Ala  Ala  Val
               1460                      1465                      1470

Asn  Ala  Ala  Val  Gln  Arg  Val  Gln  Val  Leu  Pro  Asp  Ala  Asp  Thr  Leu
          1475                      1480                      1485

Leu  His  Phe  Ala  Thr  Glu  Ser  Thr  Pro  Asp  Gly  Phe  Ser  Cys  Ser  Ser
          1490                      1495                      1500

Ser  Leu  Ser  Ala  Leu  Ser  Leu  Asp  Glu  Pro  Phe  Ile  Gln  Lys  Asp  Val
1505                     1510                      1515                     1520

Glu  Leu  Arg  Ile  Met  Pro  Pro  Val  Gln  Glu  Asn  Asp  Asn  Gly  Asn  Glu
                    1525                     1530                      1535

Thr  Glu  Ser  Glu  Gln  Pro  Lys  Glu  Ser  Asn  Glu  Asn  Gln  Glu  Lys  Glu
               1540                      1545                      1550

Ala  Glu  Lys  Thr  Ile  Asp  Ser  Glu  Lys  Asp  Leu  Leu  Asp  Asp  Ser  Asp
               1555                      1560                      1565

Asp  Asp  Asp  Ile  Glu  Ile  Leu  Glu  Glu  Cys  Ile  Ile  Ser  Ala  Met  Pro
          1570                      1575                      1580

Thr  Lys  Ser  Ser  Arg  Lys  Ala  Lys  Lys  Pro  Ala  Gln  Thr  Ala  Ser  Lys
1585                     1590                      1595                     1600

Leu  Pro  Pro  Pro  Val  Ala  Arg  Lys  Pro  Ser  Gln  Leu  Pro  Val  Tyr  Lys
                    1605                     1610                      1615

Leu  Leu  Pro  Ser  Gln  Asn  Arg  Leu  Gln  Pro  Gln  Lys  His  Val  Ser  Phe
               1620                      1625                      1630

Thr  Pro  Gly  Asp  Asp  Met  Pro  Arg  Val  Tyr  Cys  Val  Glu  Gly  Thr  Pro
               1635                      1640                      1645

Ile  Asn  Phe  Ser  Thr  Ala  Thr  Ser  Leu  Ser  Asp  Leu  Thr  Ile  Glu  Ser
          1650                      1655                      1660

Pro  Pro  Asn  Glu  Leu  Ala  Ala  Gly  Glu  Gly  Val  Arg  Gly  Gly  Ala  Gln
1665                     1670                      1675                     1680

Ser  Gly  Glu  Phe  Glu  Lys  Arg  Asp  Thr  Ile  Pro  Thr  Glu  Gly  Arg  Ser
                    1685                     1690                      1695

Thr  Asp  Glu  Ala  Gln  Gly  Gly  Lys  Thr  Ser  Ser  Val  Thr  Ile  Pro  Glu
               1700                      1705                      1710

Leu  Asp  Asp  Asn  Lys  Ala  Glu  Glu  Gly  Asp  Ile  Leu  Ala  Glu  Cys  Ile
          1715                      1720                      1725

Asn  Ser  Ala  Met  Pro  Lys  Gly  Lys  Ser  His  Lys  Pro  Phe  Arg  Val  Lys
          1730                      1735                      1740

Lys  Ile  Met  Asp  Gln  Val  Gln  Gln  Ala  Ser  Ala  Ser  Ser  Ser  Ala  Pro
1745                     1750                      1755                     1760

Asn  Lys  Asn  Gln  Leu  Asp  Gly  Lys  Lys  Lys  Lys  Pro  Thr  Ser  Pro  Val
                    1765                     1770                      1775

Lys  Pro  Ile  Pro  Gln  Asn  Thr  Glu  Tyr  Arg  Thr  Arg  Val  Arg  Lys  Asn
               1780                      1785                      1790

Ala  Asp  Ser  Lys  Asn  Asn  Leu  Asn  Ala  Glu  Arg  Val  Phe  Ser  Asp  Asn
               1795                      1800                      1805

Lys  Asp  Ser  Lys  Lys  Gln  Asn  Leu  Lys  Asn  Asn  Ser  Lys  Asp  Phe  Asn
          1810                      1815                      1820

Asp  Lys  Leu  Pro  Asn  Asn  Glu  Asp  Arg  Val  Arg  Gly  Ser  Phe  Ala  Phe
1825                     1830                      1835                     1840

Asp  Ser  Pro  His  His  Tyr  Thr  Pro  Ile  Glu  Gly  Thr  Pro  Tyr  Cys  Phe
                    1845                     1850                      1855

Ser  Arg  Asn  Asp  Ser  Leu  Ser  Ser  Leu  Asp  Phe  Asp  Asp  Asp  Asp  Val
               1860                      1865                      1870
```

| | | | | | | | | | | | | | | |
|---|---|---|---|---|---|---|---|---|---|---|---|---|---|---|
|Asp|Leu|Ser|Arg|Glu|Lys|Ala|Glu|Leu|Arg|Lys|Ala|Lys|Glu|Asn|Lys|
| | |1875| | | |1880| | | | |1885| | | |
|Glu|Ser|Glu|Ala|Lys|Val|Thr|Ser|His|Thr|Glu|Leu|Thr|Ser|Asn|Gln|
| |1890| | | | |1895| | | | |1900| | | |
|Gln|Ser|Ala|Asn|Lys|Thr|Gln|Ala|Ile|Ala|Lys|Gln|Pro|Ile|Asn|Arg|
|1905| | | | |1910| | | | |1915| | | | |1920|
|Gly|Gln|Pro|Lys|Pro|Ile|Leu|Gln|Lys|Gln|Ser|Thr|Phe|Pro|Gln|Ser|
| | | | |1925| | | | |1930| | | | |1935| |
|Ser|Lys|Asp|Ile|Pro|Asp|Arg|Gly|Ala|Ala|Thr|Asp|Glu|Lys|Leu|Gln|
| | | |1940| | | | |1945| | | | |1950| | |
|Asn|Phe|Ala|Ile|Glu|Asn|Thr|Pro|Val|Cys|Phe|Ser|His|Asn|Ser|Ser|
| | |1955| | | |1960| | | | |1965| | | | |
|Leu|Ser|Ser|Leu|Ser|Asp|Ile|Asp|Gln|Glu|Asn|Asn|Asn|Lys|Glu|Asn|
| |1970| | | | |1975| | | | |1980| | | | |
|Glu|Pro|Ile|Lys|Glu|Thr|Glu|Pro|Pro|Asp|Ser|Gln|Gly|Glu|Pro|Ser|
|1985| | | | |1990| | | | |1995| | | | |2000|
|Lys|Pro|Gln|Ala|Ser|Gly|Tyr|Ala|Pro|Lys|Ser|Phe|His|Val|Glu|Asp|
| | | | |2005| | | | |2010| | | | |2015| |
|Thr|Pro|Val|Cys|Phe|Ser|Arg|Asn|Ser|Ser|Leu|Ser|Ser|Leu|Ser|Ile|
| | | |2020| | | | |2025| | | | |2030| | |
|Asp|Ser|Glu|Asp|Asp|Leu|Leu|Gln|Glu|Cys|Ile|Ser|Ser|Ala|Met|Pro|
| | |2035| | | |2040| | | | |2045| | | | |
|Lys|Lys|Lys|Lys|Pro|Ser|Arg|Leu|Lys|Gly|Asp|Asn|Glu|Lys|His|Ser|
| |2050| | | | |2055| | | | |2060| | | | |
|Pro|Arg|Asn|Met|Gly|Gly|Ile|Leu|Gly|Glu|Asp|Leu|Thr|Leu|Asp|Leu|
|2065| | | | |2070| | | | |2075| | | | |2080|
|Lys|Asp|Ile|Gln|Arg|Pro|Asp|Ser|Glu|His|Gly|Leu|Ser|Pro|Asp|Ser|
| | | | |2085| | | | |2090| | | | |2095| |
|Glu|Asn|Phe|Asp|Trp|Lys|Ala|Ile|Gln|Glu|Gly|Ala|Asn|Ser|Ile|Val|
| | | |2100| | | | |2105| | | | |2110| | |
|Ser|Ser|Leu|His|Gln|Ala|Ala|Ala|Ala|Cys|Leu|Ser|Arg|Gln|Ala|
| | |2115| | | |2120| | | | |2125| | | |
|Ser|Ser|Asp|Ser|Asp|Ser|Ile|Leu|Ser|Leu|Lys|Ser|Gly|Ile|Ser|Leu|
| |2130| | | | |2135| | | | |2140| | | | |
|Gly|Ser|Pro|Phe|His|Leu|Thr|Pro|Asp|Gln|Glu|Glu|Lys|Pro|Phe|Thr|
|2145| | | | |2150| | | | |2155| | | | |2160|
|Ser|Asn|Lys|Gly|Pro|Arg|Ile|Leu|Lys|Pro|Gly|Glu|Lys|Ser|Thr|Leu|
| | | | |2165| | | | |2170| | | | |2175| |
|Glu|Thr|Lys|Lys|Ile|Glu|Ser|Glu|Ser|Lys|Gly|Ile|Lys|Gly|Gly|Lys|
| | | |2180| | | | |2185| | | | |2190| | |
|Lys|Val|Tyr|Lys|Ser|Leu|Ile|Thr|Gly|Lys|Val|Arg|Ser|Asn|Ser|Glu|
| | |2195| | | |2200| | | | |2205| | | | |
|Ile|Ser|Gly|Gln|Met|Lys|Gln|Pro|Leu|Gln|Ala|Asn|Met|Pro|Ser|Ile|
| |2210| | | | |2215| | | | |2220| | | | |
|Ser|Arg|Gly|Arg|Thr|Met|Ile|His|Ile|Pro|Gly|Val|Arg|Asn|Ser|Ser|
|2225| | | | |2230| | | | |2235| | | | |2240|
|Ser|Ser|Thr|Ser|Pro|Val|Ser|Lys|Lys|Gly|Pro|Pro|Leu|Lys|Thr|Pro|
| | | | |2245| | | | |2250| | | | |2255| |
|Ala|Ser|Lys|Ser|Pro|Ser|Glu|Gly|Gln|Thr|Ala|Thr|Thr|Ser|Pro|Arg|
| | | |2260| | | | |2265| | | | |2270| | |
|Gly|Ala|Lys|Pro|Ser|Val|Lys|Ser|Glu|Leu|Ser|Pro|Val|Ala|Arg|Gln|
| | |2275| | | |2280| | | | |2285| | | | |
|Thr|Ser|Gln|Ile|Gly|Gly|Ser|Ser|Lys|Ala|Pro|Ser|Arg|Ser|Gly|Ser|
| |2290| | | | |2295| | | | |2300| | | | |

```
Arg Asp Ser Thr Pro Ser Arg Pro Ala Gln Gln Pro Leu Ser Arg Pro
305              2310            2315                    2320

Ile Gln Ser Pro Gly Arg Asn Ser Ile Ser Pro Gly Arg Asn Gly Ile
                2325            2330            2335

Ser Pro Pro Asn Lys Leu Ser Gln Leu Pro Arg Thr Ser Ser Pro Ser
                2340            2345                2350

Thr Ala Ser Thr Lys Ser Ser Gly Ser Gly Lys Met Ser Tyr Thr Ser
        2355            2360            2365

Pro Gly Arg Gln Met Ser Gln Gln Asn Leu Thr Lys Gln Thr Gly Leu
        2370            2375            2380

Ser Lys Asn Ala Ser Ser Ile Pro Arg Ser Glu Ser Ala Ser Lys Gly
385             2390            2395                    2400

Leu Asn Gln Met Asn Asn Gly Asn Gly Ala Asn Lys Lys Val Glu Leu
                2405            2410            2415

Ser Arg Met Ser Ser Thr Lys Ser Ser Gly Ser Glu Ser Asp Arg Ser
                2420            2425            2430

Glu Arg Pro Val Leu Val Arg Gln Ser Thr Phe Ile Lys Glu Ala Pro
        2435            2440            2445

Ser Pro Thr Leu Arg Arg Lys Leu Glu Glu Ser Ala Ser Phe Glu Ser
        2450            2455            2460

Leu Ser Pro Ser Ser Arg Pro Ala Ser Pro Thr Arg Ser Gln Ala Gln
465             2470            2475                    2480

Thr Pro Val Leu Ser Pro Ser Leu Pro Asp Met Ser Leu Ser Thr His
                2485            2490            2495

Ser Ser Val Gln Ala Gly Gly Trp Arg Lys Leu Pro Pro Asn Leu Ser
                2500            2505            2510

Pro Thr Ile Glu Tyr Asn Asp Gly Arg Pro Ala Lys Arg His Asp Ile
        2515            2520            2525

Ala Arg Ser His Ser Glu Ser Pro Ser Arg Leu Pro Ile Asn Arg Ser
        2530            2535            2540

Gly Thr Trp Lys Arg Glu His Ser Lys His Ser Ser Ser Leu Pro Arg
545             2550            2555                    2560

Val Ser Thr Trp Arg Arg Thr Gly Ser Ser Ser Ser Ile Leu Ser Ala
                2565            2570            2575

Ser Ser Glu Ser Ser Glu Lys Ala Lys Ser Glu Asp Glu Lys His Val
                2580            2585            2590

Asn Ser Ile Ser Gly Thr Lys Gln Ser Lys Glu Asn Gln Val Ser Ala
        2595            2600            2605

Lys Gly Thr Trp Arg Lys Ile Lys Glu Asn Glu Phe Ser Pro Thr Asn
        2610            2615            2620

Ser Thr Ser Gln Thr Val Ser Ser Gly Ala Thr Asn Gly Ala Glu Ser
625             2630            2635                    2640

Lys Thr Leu Ile Tyr Gln Met Ala Pro Ala Val Ser Lys Thr Glu Asp
                2645            2650            2655

Val Trp Val Arg Ile Glu Asp Cys Pro Ile Asn Asn Pro Arg Ser Gly
                2660            2665            2670

Arg Ser Pro Thr Gly Asn Thr Pro Pro Val Ile Asp Ser Val Ser Glu
        2675            2680            2685

Lys Ala Asn Pro Asn Ile Lys Asp Ser Lys Asp Asn Gln Ala Lys Gln
        2690            2695            2700

Asn Val Gly Asn Gly Ser Val Pro Met Arg Thr Val Gly Leu Glu Asn
705             2710            2715                    2720

Arg Leu Asn Ser Phe Ile Gln Val Asp Ala Pro Asp Gln Lys Gly Thr
```

2725                           2730                           2735

Glu  Ile  Lys  Pro  Gly  Gln  Asn  Asn  Pro  Val  Pro  Val  Ser  Glu  Thr  Asn
                    2740                      2745                 2750

Glu  Ser  Ser  Ile  Val  Glu  Arg  Thr  Pro  Phe  Ser  Ser  Ser  Ser  Ser  Ser
                2755                      2760                 2765

Lys  His  Ser  Ser  Pro  Ser  Gly  Thr  Val  Ala  Ala  Arg  Val  Thr  Pro  Phe
          2770                      2775                 2780

Asn  Tyr  Asn  Pro  Ser  Pro  Arg  Lys  Ser  Ser  Ala  Asp  Ser  Thr  Ser  Ala
785                      2790                      2795                      2800

Arg  Pro  Ser  Gln  Ile  Pro  Thr  Pro  Val  Asn  Asn  Asn  Thr  Lys  Lys  Arg
                    2805                      2810                      2815

Asp  Ser  Lys  Thr  Asp  Ser  Thr  Glu  Ser  Ser  Gly  Thr  Gln  Ser  Pro  Lys
               2820                      2825                      2830

Arg  His  Ser  Gly  Ser  Tyr  Leu  Val  Thr  Ser  Val
          2835                      2840

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: ral2(yeast)

( x i ) SEQUENCE DESCRIPTION: SEQ ID NO:8:

Leu  Thr  Gly  Ala  Lys  Gly  Leu  Gln  Leu  Arg  Ala  Leu  Arg  Arg  Ile  Ala
1                   5                        10                       15

Arg  Ile  Glu  Gln  Gly  Gly  Thr  Ala  Ile  Ser  Pro  Thr  Ser  Pro  Leu
               20                       25                       30

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: m3(mAChR)

( x i ) SEQUENCE DESCRIPTION: SEQ ID NO:9:

Leu  Tyr  Trp  Arg  Ile  Tyr  Lys  Glu  Thr  Glu  Lys  Arg  Thr  Lys  Glu  Leu
1                   5                        10                       15

Ala  Gly  Leu  Gln  Ala  Ser  Gly  Thr  Glu  Ala  Glu  Thr  Glu
               20                       25

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide (vi) ORIGINAL SOURCE:
    (A) ORGANISM: Homo sapiens (vii) IMMEDIATE SOURCE:
    (B) CLONE: MCC (xi) SEQUENCE DESCRIPTION: SEQ ID NO:10:

| Leu | Tyr | Pro | Asn | Leu | Ala | Glu | Glu | Arg | Ser | Arg | Trp | Glu | Lys | Glu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Gly | Leu | Arg | Glu | Glu | Asn | Glu | Ser | Leu | Thr | Ala | Met |
|-----|-----|-----|-----|-----|-----|-----|-----|-----|-----|-----|-----|-----|
|     |     |     | 20  |     |     |     |     | 25  |     |     |     |     |

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:11:

GTATCAAGAC TGTGACTTTT AATTGTAGTT TATCCATTTT          40

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:12:

TTTAGAATTT CATGTTAATA TATTGTGTTC TTTTTAACAG          40

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:13:

GTAGATTTTA AAAGGTGTT TTAAATAAT TTTTAAGCT            40

(2) INFORMATION FOR SEQ ID NO:14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (v i) ORIGINAL SOURCE:
    (A) ORGANISM: Homo sapiens (x i) SEQUENCE DESCRIPTION: SEQ ID NO:14:

AAGCAATTGT TGTATAAAAA CTTGTTTCTA TTTTATTTAG          40

(2) INFORMATION FOR SEQ ID NO:15:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:15:

GTAACTTTTC TTCATATAGT AAACATTGCC TTGTGTACTC          40

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:16:

NNNNNNNNNN NNNGTCCCTT TTTTAAAAA AAAAAAATAG          40

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:17:

GTAAGTAACT TGGCAGTACA ACTTATTTGA AACTTTAATA          40

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:18:

ATACAAGATA TTGATACTTT TTTATTATTT GTGGTTTAG          40

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:19:

```
GTAAGTTACT TGTTTCTAAG TGATAAAACA GYGAAGAGCT                               40
```

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:20:

```
AATAAAAACA TAACTAATTA GGTTTCTTGT TTTATTTTAG                               40
```

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:21:

```
GTTAGTAAAT TSCCTTTTTT GTTTGTGGGT ATAAAAATAG                               40
```

( 2 ) INFORMATION FOR SEQ ID NO:22:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:22:

```
ACCATTTTTG CATGTACTGA TGTTAACTCC ATCTTAACAG                               40
```

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear (i i) MOLECULE TYPE: cDNA (v i) ORIGINAL SOURCE:
    (A) ORGANISM: Homo sapiens (x i) SEQUENCE DESCRIPTION: SEQ ID NO:23:

GTAAATAAAT TATTTTATCA TATTTTTTAA AATTATTTAA                                    40

(2) INFORMATION FOR SEQ ID NO:24:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:24:

CATGATGTTA TCTGTATTTA CCTATAGTCT AAATTATACC ATCTATAATG TGCTTAATTT              60

TTAG                                                                           64

(2) INFORMATION FOR SEQ ID NO:25:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:25:

GTAACAGAAG ATTACAAACC CTGGTCACTA ATGCCATGAC TACTTTGCTA AG                      52

(2) INFORMATION FOR SEQ ID NO:26:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:26:

GGATATTAAA GTCGTAATTT TGTTTCTAAA CTCATTGGC CCACAG                              46

(2) INFORMATION FOR SEQ ID NO:27:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:27:

GTATGTTCTC TATAGTGTAC ATCGTAGTGC ATGTTTCAAA        40

( 2 ) INFORMATION FOR SEQ ID NO:28:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:28:

CATCATTGCT CTTCAAATAA CAAAGCATTA TGGTTTATGT TGATTTTATT TTTCAG        56

( 2 ) INFORMATION FOR SEQ ID NO:29:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:29:

GTAAGACAAA AATGTTTTTT AATGACATAG ACAATTACTG GTG        43

( 2 ) INFORMATION FOR SEQ ID NO:30:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:30:

TTAGATGATT GTCTTTTTCC TCTTGCCCTT TTTAAATTAG        40

( 2 ) INFORMATION FOR SEQ ID NO:31:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:31:

GTATGTTTTT ATAACATGTA TTTCTTAAGA TAGCTCAGGT ATGA        44

( 2 ) INFORMATION FOR SEQ ID NO:32:

( i ) SEQUENCE CHARACTERISTICS:
        ( A ) LENGTH: 54 base pairs ( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:32:

GCTTGGCTTC AAGTTGNCTT TTTAATGATC CTCTATTCTG TATTTAATTT ACAG    54

( 2 ) INFORMATION FOR SEQ ID NO:33:

( i ) SEQUENCE CHARACTERISTICS:
( A ) LENGTH: 65 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:33:

GTACTATTTA GAATTTCACC TGTTTTTCTT TTTTCTCTTT TTCTTTGAGG CAGGGTCTCA    60

CTCTG    65

( 2 ) INFORMATION FOR SEQ ID NO:34:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:34:

GCAACTAGTA TGATTTTATG TATAAATTAA TCTAAAATTG ATTAATTTCC AG    52

( 2 ) INFORMATION FOR SEQ ID NO:35:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:35:

GTACCTTTGA AAACATTTAG TACTATAATA TGAATTTCAT GT    42

( 2 ) INFORMATION FOR SEQ ID NO:36:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: cDNA -continued (vi) ORIGINAL SOURCE:
        (A) ORGANISM: Homo sapiens (xi) SEQUENCE DESCRIPTION: SEQ ID NO:36:

CCAACTCNAA TTAGATGACC CATATTCAGA AACTTACTAG                40

(2) INFORMATION FOR SEQ ID NO:37:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:37:

GTATATATAG AGTTTTATAT TACTTTTAAA GTACAGAATT CATACTCTCA AAAA    54

(2) INFORMATION FOR SEQ ID NO:38:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:38:

ATTGTGACCT TAATTTGTG ATCTCTTGAT TTTTATTTCA G                  41

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:39:

TCCCCGCCTG CCGCTCTC                                           18

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:40:

GCAGCGGCGG CTCCCGTG                                           18

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:41:

```
GTGAACGGCT CTCATGCTGC                                              20
```

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:42:

```
ACGTGCGGGG AGGAATGGA                                               19
```

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:43:

```
ATGATATCTT ACCAAATGAT ATAC                                         24
```

( 2 ) INFORMATION FOR SEQ ID NO:44:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:44:

```
TTATTCCTAC TTCTTCTATA CAG                                          23
```

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:45:

TACCCATGCT GGCTCTTTTT C     21

( 2 ) INFORMATION FOR SEQ ID NO:46:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:46:

TGGGGCCATC TTGTTCCTGA     20

( 2 ) INFORMATION FOR SEQ ID NO:47:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:47:

ACATTAGGCA CAAAGCTTGC AA     22

( 2 ) INFORMATION FOR SEQ ID NO:48:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:48:

ATCAAGCTCC AGTAAGAAGG TA     22

( 2 ) INFORMATION FOR SEQ ID NO:49:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:49:

TGCGGCTCCT GGGTTGTTG     19

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:50:

GCCCCTTCCT TTCTGAGGAC                                              20

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:51:

TTTTCTCCTG CCTCTTACTG C                                          21

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:52:

ATGACACCCC CCATTCCCTC                                              20

( 2 ) INFORMATION FOR SEQ ID NO:53:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:53:

CCACTTAAAG CACATATATT TAGT                                      24

( 2 ) INFORMATION FOR SEQ ID NO:54:

( i ) SEQUENCE CHARACTERISTICS:
        ( A ) LENGTH: 22 base pairs
        ( B ) TYPE: nucleic acid
        ( C ) STRANDEDNESS: single ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:54:

GTATGGAAAA TAGTGAAGAA CC     22

( 2 ) INFORMATION FOR SEQ ID NO:55:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:55:

TTCTTAAGTC CTGTTTTTCT TTTG     24

( 2 ) INFORMATION FOR SEQ ID NO:56:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:56:

TTTAGAACCT TTTTGTGTT GTG     23

( 2 ) INFORMATION FOR SEQ ID NO:57:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:57:

CTCAGATTAT ACACTAAGCC TAAC     24

( 2 ) INFORMATION FOR SEQ ID NO:58:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:58:

```
CATGTCTCTT ACAGTAGTAC CA                                                          22
```

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:59:

```
AGGTCCAAGG GTAGCCAAGG                                                             20
```

( 2 ) INFORMATION FOR SEQ ID NO:60:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:60:

```
TAAAAATGGA TAAACTACAA TTAAAAG                                                     27
```

( 2 ) INFORMATION FOR SEQ ID NO:61:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:61:

```
AAATACAGAA TCATGTCTTG AAGT                                                        24
```

( 2 ) INFORMATION FOR SEQ ID NO:62:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:62:

```
ACACCTAAAG ATGACAATTT GAG                                                         23
```

( 2 ) INFORMATION FOR SEQ ID NO:63:

( i ) SEQUENCE CHARACTERISTICS:
        ( A ) LENGTH: 24 base pairs (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:63:

TAACTTAGAT AGCAGTAATT TCCC 24

(2) INFORMATION FOR SEQ ID NO:64:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:64:

ACAATAAACT GGAGTACACA AGG 23

(2) INFORMATION FOR SEQ ID NO:65:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:65:

ATAGGTCATT GCTTCTTGCT GAT 23

(2) INFORMATION FOR SEQ ID NO:66:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:66:

TGAATTTTAA TGGATTACCT AGGT 24

(2) INFORMATION FOR SEQ ID NO:67:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens ( x i ) SEQUENCE DESCRIPTION: SEQ ID NO:67:

CTTTTTTGC TTTACTGAT TAACG    25

( 2 ) INFORMATION FOR SEQ ID NO:68:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:68:

TGTAATTCAT TTTATTCCTA ATAGCTC    27

( 2 ) INFORMATION FOR SEQ ID NO:69:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:69:

GGTAGCCATA GTATGATTAT TTCT    24

( 2 ) INFORMATION FOR SEQ ID NO:70:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:70:

CTACCTATTT TTATACCCAC AAAC    24

( 2 ) INFORMATION FOR SEQ ID NO:71:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:71:

AAGAAAGCCT ACACCATTTT TGC    23

( 2 ) INFORMATION FOR SEQ ID NO:72:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:72:

GATCATTCTT AGAACCATCT TGC           23

( 2 ) INFORMATION FOR SEQ ID NO:73:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:73:

ACCTATAGTC TAAATTATAC CATC          24

( 2 ) INFORMATION FOR SEQ ID NO:74:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:74:

GTCATGGCAT TAGTGACCAG               20

( 2 ) INFORMATION FOR SEQ ID NO:75:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:75:

AGTCGTAATT TTGTTTCTAA ACTC          24

( 2 ) INFORMATION FOR SEQ ID NO:76:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:76:

TGAAGGACTC GGATTTCACG C                                     21

( 2 ) INFORMATION FOR SEQ ID NO:77:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:77:

TCATTCACTC ACAGCCTGAT GAC                                   23

( 2 ) INFORMATION FOR SEQ ID NO:78:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:78:

GCTTTGAAAC ATGCACTACG AT                                    22

( 2 ) INFORMATION FOR SEQ ID NO:79:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:79:

AAACATCATT GCTCTTCAAA TAAC                                  24

( 2 ) INFORMATION FOR SEQ ID NO:80:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:80:

TACCATGATT TAAAAATCCA CCAG                                  24

( 2 ) INFORMATION FOR SEQ ID NO:81:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:81:

GATGATTGTC TTTTCCTCT TGC    23

( 2 ) INFORMATION FOR SEQ ID NO:82:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:82:

CTGAGCTATC TTAAGAAATA CATG    24

( 2 ) INFORMATION FOR SEQ ID NO:83:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:83:

TTTTAAATGA TCCTCTATTC TGTAT    25

( 2 ) INFORMATION FOR SEQ ID NO:84:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:84:

ACAGAGTCAG ACCCTGCCTC AAAG    24

( 2 ) INFORMATION FOR SEQ ID NO:85:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:85:

TTTCTATTCT TACTGCTAGC ATT          23

(2) INFORMATION FOR SEQ ID NO:86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:86:

ATACACAGGT AAGAAATTAG GA          22

(2) INFORMATION FOR SEQ ID NO:87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:87:

TAGATGACCC ATATTCTGTT TC          22

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:88:

CAATTAGGTC TTTTGAGAG TA          22

(2) INFORMATION FOR SEQ ID NO:89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:89:

GTTACTGCAT ACACATTGTG AC          22

( 2 ) INFORMATION FOR SEQ ID NO:90:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:90:

GCTTTTTGTT TCCTAACATG AAG        23

( 2 ) INFORMATION FOR SEQ ID NO:91:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:91:

TCTCCCACAG GTAATACTCC C        21

( 2 ) INFORMATION FOR SEQ ID NO:92:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:92:

GCTAGAACTG AATGGGGTAC G        21

( 2 ) INFORMATION FOR SEQ ID NO:93:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:93:

CAGGACAAAA TAATCCTGTC CC        22

( 2 ) INFORMATION FOR SEQ ID NO:94:

( i ) SEQUENCE CHARACTERISTICS:
        ( A ) LENGTH: 24 base pairs
        ( B ) TYPE: nucleic acid
        ( C ) STRANDEDNESS: single (D) TOPOLOGY: linear (ii) MOLECULE TYPE: cDNA (vi) ORIGINAL SOURCE:
 (A) ORGANISM: Homo sapiens (xi) SEQUENCE DESCRIPTION: SEQ ID NO:94:

ATTTTCTTAG TTTCATTCTT CCTC                24

(2) INFORMATION FOR SEQ ID NO: 95:

(i) SEQUENCE CHARACTERISTICS:
 (A) LENGTH: 25 base pairs
 (B) TYPE: nucleic acid
 (C) STRANDEDNESS: single
 (D) TOPOLOGY: linear (ii) MOLECULE TYPE: cDNA (vi) ORIGINAL SOURCE:
 (A) ORGANISM: Homo sapiens (xi) SEQUENCE DESCRIPTION: SEQ ID NO:95:

AGAAGGATCC CTTGTGCAGT GTGGA               25

(2) INFORMATION FOR SEQ ID NO: 96:

(i) SEQUENCE CHARACTERISTICS:
 (A) LENGTH: 24 base pairs
 (B) TYPE: nucleic acid
 (C) STRANDEDNESS: single
 (D) TOPOLOGY: linear (ii) MOLECULE TYPE: cDNA (vi) ORIGINAL SOURCE:
 (A) ORGANISM: Homo sapiens (xi) SEQUENCE DESCRIPTION: SEQ ID NO:96:

GACAGGATCC TGAAGCTGAG TTTG                24

(2) INFORMATION FOR SEQ ID NO: 97:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA (vi) ORIGINAL SOURCE:
 (A) ORGANISM: Homo sapiens (xi) SEQUENCE DESCRIPTION: SEQ ID NO:97:

TCAGAAAGTG CTGAAGAG                       18

(2) INFORMATION FOR SEQ ID NO: 98:

(i) SEQUENCE CHARACTERISTICS:
 (A) LENGTH: 19 base pairs
 (B) TYPE: nucleic acid
 (C) STRANDEDNESS: single
 (D) TOPOLOGY: linear (ii) MOLECULE TYPE: cDNA (vi) ORIGINAL SOURCE:
 (A) ORGANISM: Homo sapiens (xi) SEQUENCE DESCRIPTION: SEQ ID NO:98:

GGAATAATTA GGTCTCCAA                                                                                            19

( 2 ) INFORMATION FOR SEQ ID NO: 99:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:99:

GCAAATCCTA AGAGAGAACA A                                                                                         21

( 2 ) INFORMATION FOR SEQ ID NO: 100:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:100:

GATGGCAAGC TTGAGCCAG                                                                                            19

( 2 ) INFORMATION FOR SEQ ID NO: 101:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:101:

GTTCCAGCAG TGTCACAG                                                                                             18

( 2 ) INFORMATION FOR SEQ ID NO: 102:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:102:

GGGAGATTTC GCTCCTGA                                                                                             18